(12) United States Patent  
Yabe et al.

(10) Patent No.: US 8,877,355 B2  
(45) Date of Patent: Nov. 4, 2014

(54) MONOAMINE COMPOUND, CHARGE-TRANSPORTING MATERIAL, AND ORGANIC ELECTROLUMINESCENT DEVICE

(71) Applicant: Mitsubishi Chemical Corporation, Chiyoda-ku (JP)

(72) Inventors: Masayoshi Yabe, Kanagawa (JP); Masayo Fugono, Kanagawa (JP); Koichiro Iida, Kanagawa (JP); Masako Takeuchi, Kanagawa (JP); Tomoyuki Ogata, Kanagawa (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 13/841,378

(22) Filed: Mar. 15, 2013

(65) Prior Publication Data

US 2013/0214263 A1    Aug. 22, 2013

Related U.S. Application Data

(63) Continuation of application No. 11/914,767, filed as application No. PCT/JP2006/309758 on May 16, 2006, now Pat. No. 8,427,046.

(30) Foreign Application Priority Data

May 17, 2005 (JP) ................... 2005-143569  
Apr. 27, 2006 (JP) ................... 2006-124450

(51) Int. Cl.
| | | |
|---|---|---|
| H01L 51/54 | (2006.01) | |
| H01L 51/00 | (2006.01) | |
| C09K 11/06 | (2006.01) | |
| H05B 33/14 | (2006.01) | |
| C07C 211/54 | (2006.01) | |
| H01L 51/50 | (2006.01) | |

(52) U.S. Cl.  
CPC ............ *H01L 51/0059* (2013.01); *C09K 11/06* (2013.01); *H01L 51/0072* (2013.01); *H01L 51/0095* (2013.01); *C09K 2211/1059* (2013.01); *H01L 51/0035* (2013.01); *H01L 51/0052* (2013.01); *C09K 2211/1014* (2013.01); *H01L 51/0071* (2013.01); *H01L 51/5048* (2013.01); *H05B 33/14* (2013.01); *C09K 2211/1007* (2013.01); *H01L 51/0085* (2013.01); *C09K 2211/1092* (2013.01); *C09K 2211/186* (2013.01); *C09K 2211/185* (2013.01); *H01L 51/5016* (2013.01); *C09K 2211/1037* (2013.01); *H01L 2251/308* (2013.01); *C07C 211/54* (2013.01); *H01L 51/0067* (2013.01); *C09K 2211/1029* (2013.01); *C09K 2211/1044* (2013.01); *H01L 51/0081* (2013.01); *H01L 51/006* (2013.01); *H01L 51/008* (2013.01); *Y10S 428/917* (2013.01)  
USPC .......... 428/690; 428/917; 313/504; 313/505; 313/506; 257/40; 257/E51.05; 257/E51.026; 257/E51.032; 564/262; 564/426; 564/430; 564/432; 564/434; 548/304.1; 548/418; 548/440; 548/444

(58) Field of Classification Search  
USPC ............... 428/690, 917; 313/504, 505, 506; 257/40, E51.05, E51.026, E51.032; 564/26, 426, 430, 432, 434; 548/304.1, 548/418, 440, 444  
See application file for complete search history.

(56) References Cited

U.S. PATENT DOCUMENTS

| | | |
|---|---|---|
| 4,869,988 A | 9/1989 | Ong et al. |
| 4,937,165 A | 6/1990 | Ong et al. |
| 5,616,801 A | 4/1997 | Shimada et al. |
| 2001/0008711 A1 | 7/2001 | Igarashi |
| 2004/0058195 A1 | 3/2004 | Kita et al. |
| 2004/0081854 A1 | 4/2004 | Hirose et al. |
| 2004/0086745 A1 | 5/2004 | Iwakuma et al. |
| 2005/0127823 A1 | 6/2005 | Iwakuma et al. |
| 2006/0180806 A1 | 8/2006 | Arakane et al. |
| 2009/0236973 A1 | 9/2009 | Yabe et al. |

FOREIGN PATENT DOCUMENTS

| | | | |
|---|---|---|---|
| JP | 02-178667 | 7/1990 | |
| JP | 03-101739 | 4/1991 | |
| JP | 03-118548 | 5/1991 | |
| JP | 03-249759 | 11/1991 | |
| JP | 6-1972 | 1/1994 | |
| JP | 09-310066 | * 12/1997 | ............ C09K 11/06 |
| JP | 2000-160279 | 4/2000 | |
| JP | 2001-19871 | 1/2001 | |
| JP | 2001-316338 | 11/2001 | |
| JP | 2003-64355 | 3/2003 | |
| JP | 2004-22334 | 1/2004 | |
| WO | WO 03/078541 A1 | 9/2003 | |
| WO | WO 2004/066685 A1 | 8/2004 | |

OTHER PUBLICATIONS

Extended European Search Report issued Jul. 23, 2013 in Patent Application No. 13170091.6.
Office Action issued in corresponding Japanese Patent Application No. 2006-124450 on Dec. 4, 2012 with English translation.
Daisuke Mutaguchi, et al., "Development of a New Claims of Hole-Transporting and Emitting Vinyl Polymers and Their Application in Organic Electroluminescent Devices", Organic Electronics, vol. 4, No. 2-3, pp. 49-59, 2003.
M. A. Baldo, et al., "Very High-Efficiency Green Organic Light-Emitting Devices Based on Electrophosphorescence", Applied Physics Letters, vol. 75, No. 1, pp. 4-6, 1999.
Office Action issued on Oct. 22, 2012 in corresponding Taiwanese patent application No. 095117410 with English translation.
Changqi Ma, et al. "Progress in Hole-Trasnsport Materials for use in Organic Light-Emitting Diodes", Progress in Chemistry, vol. 15, No. 6, Nov. 2003, pp. 495-504.
Turksoy, et al. "Phenylene-2,5-Dimethylpyraxine co-Oligomers: Synthesis by Suzuki Couplings, X-ray Structures of Neutral and Diprotonated Terayl Species and Efficient Blue Emission", Journal of Materials Chemistry, 13, May 21, 2003, pp. 1554-1557.
Extended European Search Report issued Aug. 26, 2010, in European Patent Application No. 06746472.7.
Office Action issued Sep. 14, 2010, in Korean Patent Application No. 2007-7028698 with English translation.
Partial European Search Report issued May 27, 2011, in Patent Application No. 11159565.8.
Taiwanese Letter of Examination Report, with English translation, issued Mar. 7, 2012 in connection with Taiwanese Patent Application No. 095117410, filed Apr. 1, 2007.
Extended European Search Report issued Apr. 25, 2012 in connection with European Application No. 11 15 9565, filed Jun. 29, 2011.
Japanese Office Action issued in JP Application No. 2006-124450 on Dec. 6, 2011 with English translation.
European Office Action issued Jul. 24, 2013, in European Patent Application No. 11159565.8.

Office Action issued Jan. 9, 2014 in co-pending Taiwan Patent Application No. 095117410, with English Translation, 4 pages.

* cited by examiner

*Primary Examiner* — Gregory Clark
(74) *Attorney, Agent, or Firm* — Oblon, Spivak, McClelland, Maier & Neustadt, L.L.P.

(57) ABSTRACT

The present invention provides an organic electroluminescent device exhibiting a long life, a high luminance, and a high efficiency.
An organic electroluminescent device comprising on a substrate an anode, a hole transport layer, an organic light-emitting layer, and a cathode, wherein the organic light-emitting layer contains an organic compound having a pyridine ring, a pyrazine ring, or a triazine ring as a partial structure and the hole transport layer contains a monoamine compound represented by the following formula (I):

[Chem 1]

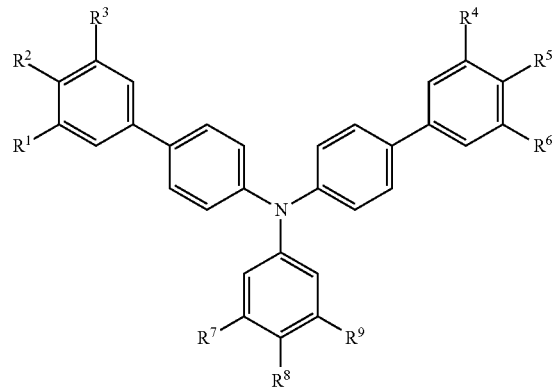

wherein $R^1$ to $R^9$ represent a hydrogen atom, an aryl group, or an alkyl group; $R^1$ to $R^9$ may be the same or different from each other; and $R^1$ to $R^9$ may further have an aryl group or an alkyl group as a substituent in the case where $R^1$ to $R^9$ are an aryl group or an alkyl group.

3 Claims, 2 Drawing Sheets

MONOAMINE COMPOUND, CHARGE-TRANSPORTING MATERIAL, AND ORGANIC ELECTROLUMINESCENT DEVICE

The present application is a continuation application of U.S. application Ser. No. 11/914,767, pending, having a filing date of Feb. 14, 2008 which is a national stage application of PCT/JP 06/309758 having a filing date of May 16, 2006 and claiming priority to Japanese application nos. 2005-143569 and 2006-124450 having filing dates of May 17, 2005 and Apr. 27, 2006, respectively.

TECHNICAL FIELD

The present invention relates to an organic electroluminescent device. More specifically, it relates to a long-life organic electroluminescent device.

BACKGROUND ART

Recently, as a thin-film type electroluminescent device, instead of one using an inorganic material, there has been developed an organic electroluminescent device using an organic thin film. The organic electroluminescent device usually comprises a hole-injection layer, a hole transport layer, an organic light-emitting layer, an electron transport layer, and the like between a cathode and an anode and materials suitable for the individual layers have been developed.

For example, Patent Document 1 proposes an organic electroluminescent device excellent in luminance, luminous efficiency, and heat resistance, wherein an amine compound having a respective specific structure is incorporated into the hole-injection layer and the hole transport layer and tris(8-quinolinolato)aluminum is incorporated into the light-emitting layer.

However, though the device is excellent in luminance, luminous efficiency, and heat resistance to some extent, a further problem is present with regard to a life of the device.

Moreover, since tris(8-quinolinolato)aluminum is insufficient in light emission efficiency, maximum light emission luminance, and color purity, there is a problem that application thereof to a full-color display use is limited.

Furthermore, hitherto, the organic electroluminescent device has utilized fluorescent emission but it is investigated to use not the fluorescent emission but phosphorescent emission during an attempt to enhance light emission efficiency. However, in the case of using the phosphorescent emission, it is present situation that a sufficient luminous efficiency is not yet obtained.

Most of the organic electroluminescent devices using a phosphorescent molecule hitherto are characterized to use a material containing a carbazolyl group as a material for the light-emitting layer (host materials). For example, in Non-Patent Document 1, the following biphenyl derivative shown below is used as a host material.

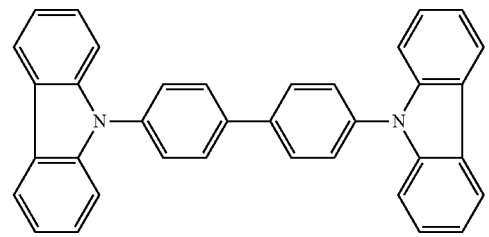

[Chem 1]

However, the organic electroluminescent device using the above biphenyl derivative has problems in electron transporting property and durability against electric reduction.

Thus, recently, for the purpose of concentrating recombination regions in the light-emitting layer, there has been proposed a host material having both of hole transporting property and electron transporting property and, in Patent Document 2, it is described that the following compound is used in the organic electroluminescent device.

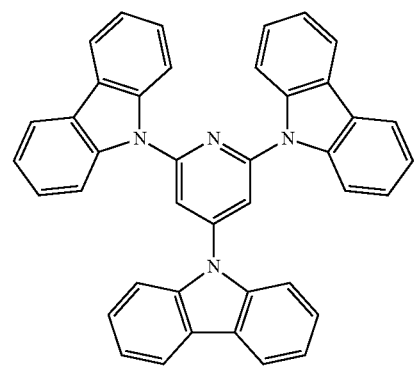

[Chem 2]

However, the organic electroluminescent device using the host material having both of hole transporting property and electron transporting property as above exhibits a tendency to incline the recombination position of charge toward the anode side and, in the case of the device using PPD or NPD as the hole transporting material, a high luminous efficiency, a high luminance, or a long driving life has not been obtained.

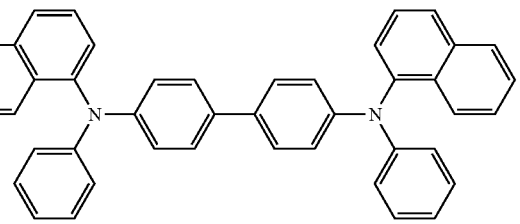

[Chem 3]

NPD

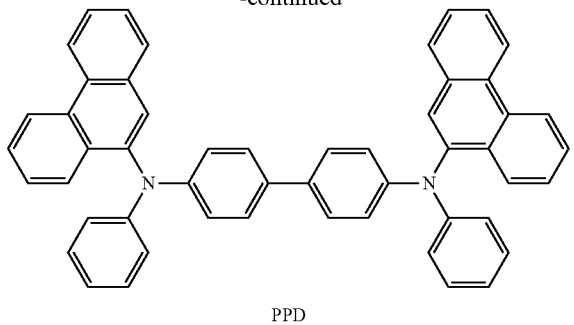

PPD

Patent Document 1: JP-A-2001-316338
Patent Document 2: JP-A-6-1972
Non-Patent Document 1: Appl. Phys. Lett., Vol. 75, p. 4, 1999

DISCLOSURE OF THE INVENTION

Problems that the Invention is to Solve

An object of the invention is to provide an organic electroluminescent device exhibiting a long life, a high luminance, and a high efficiency.

Means for Solving the Problems

As a result of extensive and intensive investigations, the present inventors have found that an organic electroluminescent device exhibiting a long life, a high luminance, and a high efficiency can be provided by specifying a compound to be incorporated in the light-emitting layer and the hole transport layer and thus have accomplished the invention.

Namely, the invention lies in an organic electroluminescent device comprising on a substrate an anode, a hole transport layer, an organic light-emitting layer, and a cathode, wherein the organic light-emitting layer contains an organic compound having a pyridine ring, a pyrazine ring, or a triazine ring as a partial structure and the hole transport layer contains a monoamine compound represented by the following formula (I):

[Chem 4]

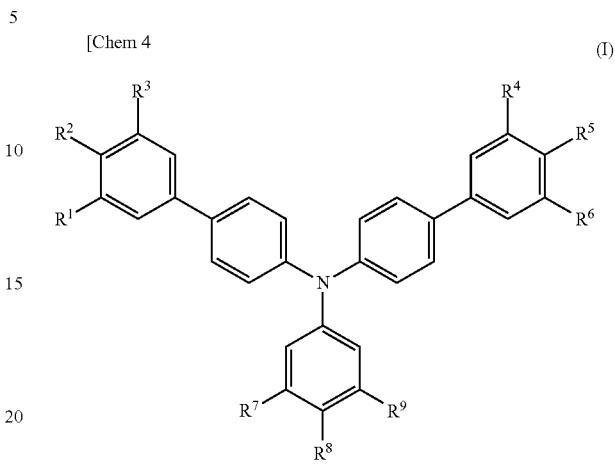

wherein $R^1$ to $R^9$ represent a hydrogen atom, an aryl group, or an alkyl group; $R^1$ to $R^9$ may be the same or different from each other; and $R^1$ to $R^9$ may further have an aryl group or an alkyl group as a substituent in the case where $R^1$ to $R^9$ are an aryl group or an alkyl group.

Moreover, the invention lies in monoamine compounds represented by the following formula (II) and the following formula (III):

[Chem 5]

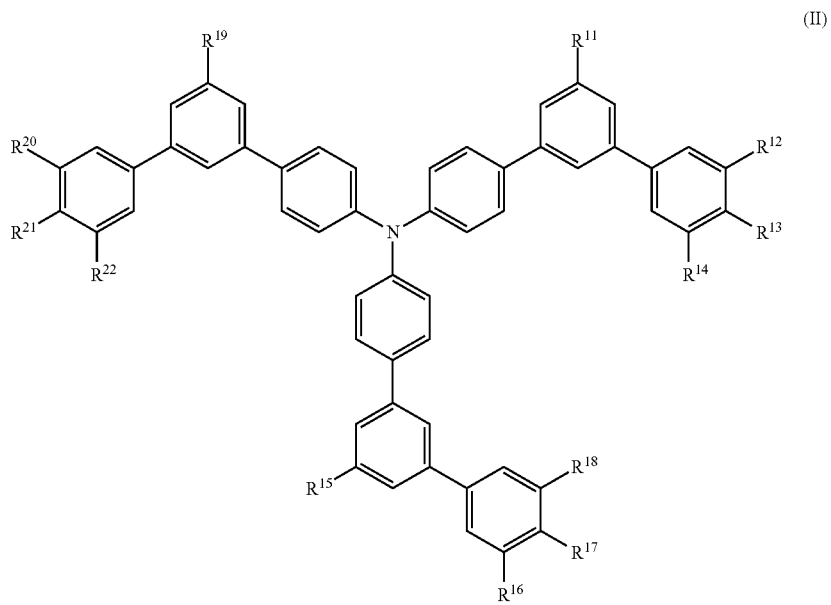

wherein $R^{11}$ to $R^{22}$ represent a hydrogen atom, an aryl group, or an alkyl group; $R^{11}$ to $R^{22}$ may be the same or different from each other; provided that any one of $R^{11}$ to $R^{22}$ is an aryl group or an alkyl group; $R^{11}$ to $R^{22}$ may further have an aryl group or an alkyl group as a substituent in the case where $R^{11}$ to $R^{22}$ are an aryl group or an alkyl group; and to $R^{22}$ may be combined with an adjacent substituent to form a ring;

[Chem 6]

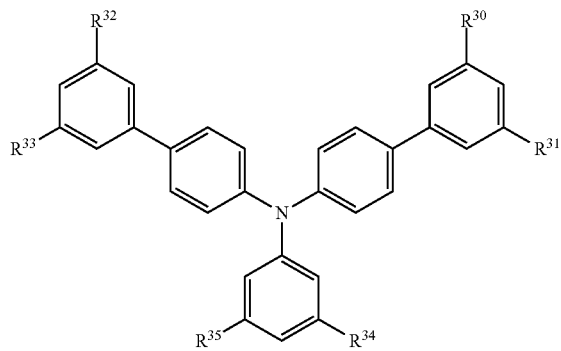

(III)

wherein $R^{30}$ to $R^{35}$ represent a hydrogen atom, an aryl group, or an alkyl group; $R^{30}$ to $R^{35}$ may be the same or different from each other; provided that any one of $R^{30}$ to $R^{35}$ is an aryl group or an alkyl group; $R^{30}$ to $R^{35}$ may further have an aryl group or an alkyl group as a substituent in the case where $R^{30}$ to $R^{35}$ are an aryl group or an alkyl group; and $R^{30}$ to $R^{35}$ may be combined with an adjacent substituent to form a ring.

Advantage of the Invention

According to the invention, an organic electroluminescent device exhibiting a long life, a high luminance, and a high efficiency can be provided. Moreover, since the monoamine compounds of the invention are excellent in electrical durability, they are useful for an organic electroluminescent device. Furthermore, they are also useful for an electrophotographic photoreceptor.

In addition, the monoamine compounds of the invention are useful not only for a charge transporting material but also for various light-emitting materials, for a solar cell, for a battery material, for a medical use, for a paint, for an organic semi-conductor material, for a toiletry material, for an anti-static material, for a thermoelectric element material, and the like.

Figure 1:
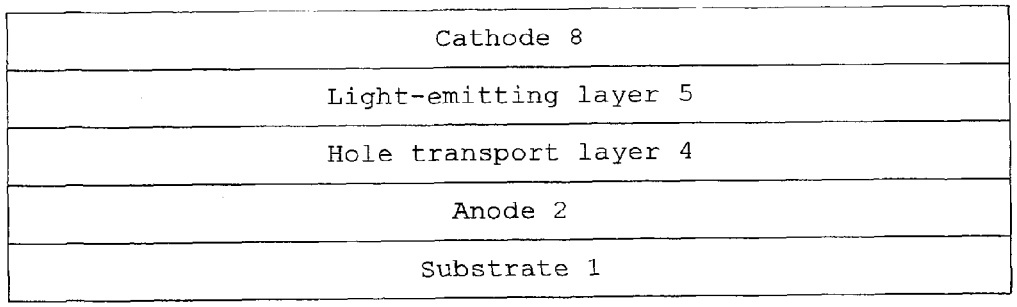
FIG. 1 is a schematic cross-sectional view showing one example of the organic electroluminescent device of the invention.

DESCRIPTION OF REFERENCE NUMERALS AND SIGNS 1 substrate
2 anode
3 hole injection layer
4 hole transport layer
5 light-emitting layer
6 hole blocking layer
7 electron transport layer
8 cathode

BEST MODE FOR CARRYING OUT THE INVENTION

The explanation of constitutional requirements described below is one example (representative example) of embodiments of the invention and the invention is not specified to these contents.

The invention relates to an organic electroluminescent device comprising on a substrate an anode, a hole transport layer, an organic light-emitting layer, and a cathode, wherein the organic light-emitting layer contains an organic compound having a pyridine ring, a pyrazine ring, or a triazine ring as a partial structure and the hole transport layer contains a monoamine compound represented by the following formula (I):

[Chem 7]

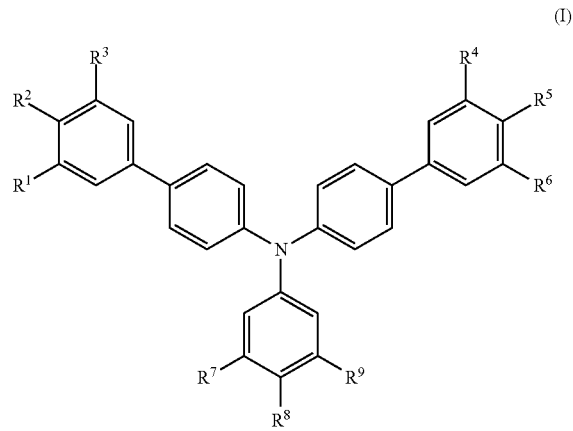

(I)

wherein $R^1$ to $R^9$ represent a hydrogen atom, an aryl group, or an alkyl group; $R^1$ to $R^9$ may be the same or different from each other; and $R^1$ to $R^9$ may further have an aryl group or an alkyl group as a substituent in the case where $R^1$ to $R^9$ are an aryl group or an alkyl group.

1. Organic Compound Having a Pyridine Ring, a Pyrazine Ring, or a Triazine Ring as a Partial Structure The invention has a characteristic that the organic light-emitting layer contains an organic compound having a pyridine ring, a pyrazine ring, or a triazine ring as a partial structure. The pyridine ring, pyrazine ring, or triazine ring may have a substituent and specific examples of the substituent include an alkyl group (preferably a linear or branched alkyl group having 1 to 8 carbon atoms, for example, including methyl, ethyl, n-propyl, 2-propyl, n-butyl, isobutyl, tert-butyl, and the like groups), which optionally has a substituent;

an alkenyl group (preferably an alkenyl group having 2 to 9 carbon atoms, for example, including vinyl, allyl, 1-butenyl, and the like groups), which optionally has a substituent;

an alkynyl group (preferably an alkynyl group having to 9 carbon atoms, for example, including ethynyl, propargyl, and the like groups), which optionally has a substituent;

an aralkyl group (preferably an aralkyl group having to 15 carbon atoms, for example, including benzyl and the like groups), which optionally has a substituent;

an amino group [preferably an alkylamino group which comprises one or more alkyl groups having 1 to 8 carbon atoms and optionally having a substituent (for example, including methylamino, dimethylamino, diethylamino, dibenzylamino, and the like groups), an arylamino group which comprises an aromatic hydrocarbon group having 6 to 12 carbon atoms and optionally having a substituent (for example, including phenylamino, diphenylamino, ditolylamino, and the like groups), a heteroarylamino group which comprises a 5- or 6-membered aromatic heterocyclic ring and optionally has a substituent (for example, including pyridylamino, thienylamino, dithienylamino, and the like groups), and an acylamino group which comprises an acyl group having 2 to 10 carbon atoms and optionally has a substituent (for example, including acetylamino, benzoylamino, and the like groups)];

an alkoxy group (preferably an alkoxy group having 1 to 8 carbon atoms and optionally having a substituent, for example, including methoxy, ethoxy, butoxy, and the like groups), which optionally has a substituent;

an aryloxy group (preferably which comprises an aromatic hydrocarbon group having 6 to 12 carbon atoms, for example, including phenyloxy, 1-naphthyloxy, 2-naphthyloxy, and the like groups), which optionally has a substituent;

a heteroaryloxy groups (preferably which comprises a 5- or 6-membered aromatic heterocyclic ring, for example, including pyridyloxy, thienyloxy, and the like groups), which optionally has a substituent;

an acyl group (preferably an acyl group having 2 to 10 carbon atoms and optionally having a substituent, for example, including formyl, acetyl, benzoyl, and the like groups), which optionally has a substituent;

an alkoxycarbonyl group (preferably an alkoxycarbonyl group having 2 to 10 carbon atoms and optionally having a substituent, for example, including methoxycarbonyl, ethoxycarbonyl, and the like groups), which optionally has a substituent;

an aryloxycarbonyl group (preferably an aryloxycarbonyl group having 7 to 13 carbon atoms and optionally having a substituent, for example, including phenoxycarbonyl and the like groups), which optionally has a substituent;

an alkylcarbonyloxy group (preferably an alkylcarbonyloxy group having 2 to 10 carbon atoms and optionally having a substituent, for example, including acetoxy and the like groups), which optionally has a substituent;

a halogen atom (particularly, a fluorine atom or a chlorine atom);

a carboxy group;

a cyano group;

a hydroxyl group;

a mercapto group;

an alkylthio group (preferably an alkylthio group having 1 to 8 carbon atoms, for example, including methylthio, ethylthio, and the like groups), which optionally has a substituent;

an arylthio group (preferably an arylthio group having 6 to 12 carbon atoms, for example, including phenylthio, 1-naphthylthio, and the like groups), which optionally has a substituent;

a sulfonyl group (for example, including mesyl, tosyl, and the like groups), which optionally has a substituent;

a silyl group (for example, including trimethylsilyl, triphenylsilyl, and the like groups), which optionally has a substituent;

a boryl group (for example, including dimesitylboryl and the like groups), which optionally has a substituent;

a phosphino group (for example, including diphenylphosphino and the like groups), which optionally has a substituent;

an aryl group (for example, including a monovalent group derived from a 5- or 6-membered monocyclic ring or 2 to 5 condensed rings, such as a benzene ring, a naphthalene ring, an anthracene ring, a phenanthrene ring, a perylene ring, a tetracene ring, a pyrene ring, a benzopyrene ring, a chrysene ring, a triphenylene ring or a fluoranthene ring), which optionally has a substituent;

or an aromatic heterocyclic group (for example, including a monovalent group derived from a 5- or 6-membered monocyclic ring or 2 to 4 condensed rings, such as a furan ring, a benzofuran ring, a thiophene ring, a benzothiophene ring, a pyrrole ring, a pyrazole ring, an imidazole ring, an oxadiazole ring, an indole ring, a carbazole ring, a pyrroloimidazole ring, a pyrrolopyrazole ring, a pyrrolopyrrole ring, a thienopyrrole ring, a thienothiophene ring, a furopyrrole ring, a furofuran ring, a thienofuran ring, a benzisoxazole ring, a benzisothiazole ring, a benzimidazole ring, a pyridine ring, a pyrazine ring, a pyridazine ring, a pyrimidine ring, a triazine ring, a quinoline ring, an isoquinoline ring, a cinnoline ring, a quinoxaline ring, a benzimidazole ring, a pyrimidine ring or a quinazoline ring), which optionally has a substituent.

Of these, in view of enhancing durability against electric oxidation and reduction and enhancing heat resistance, the substituent is more preferably an aryl group and preferable examples thereof include a monovalent group derived from a 6-membered monocyclic ring or 2 to 5 condensed rings, such as a benzene ring, a naphthalene ring, an anthracene ring, a phenanthrene ring, a perylene ring, a tetracene ring, a pyrene ring, a benzpyrene ring, a chrysene ring, a triphenylene ring or a fluoranthene ring or a monovalent group formed by combining plurality of them (for example, a biphenyl group, a terphenyl group, and the like). More preferred is a monovalent group formed by combining 1 to 8 benzene rings, such as a phenyl group, a biphenyl group, or a terphenyl group.

Among organic compounds having a pyridine ring, a pyrazine ring, or a triazine ring as a partial structure, an organic compound having a pyridine ring as a partial structure is preferred from the viewpoint of a high triplet excitation level and durability against electric oxidation and reduction.

Moreover, the organic compound having a pyridine ring, a pyrazine ring, or a triazine ring as a partial structure is preferably an organic compound further having an N-carbazole ring as a partial structure and particularly an organic compound further having an N-phenylcarbazole ring as a partial structure in view of enhancing hole injecting and transporting property.

The molecular weight of the organic compound having a pyridine ring, a pyrazine ring, or a triazine ring as a partial structure is usually 5000 or less, preferably 2,000 or less.

In this connection, the phrase "optionally having (have) a substituent" in the invention means a fact of optionally having one or more substituents.

As the compound having a pyridine ring as a partial structure, the compounds exemplified below may be mentioned. In the following compounds, —N-Cz represents an N-carbazolyl group. In addition, Ph represents a phenyl group.

[Chem 8]
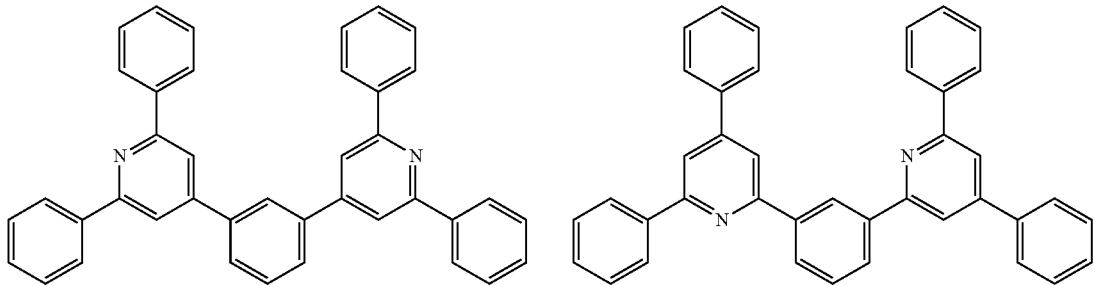
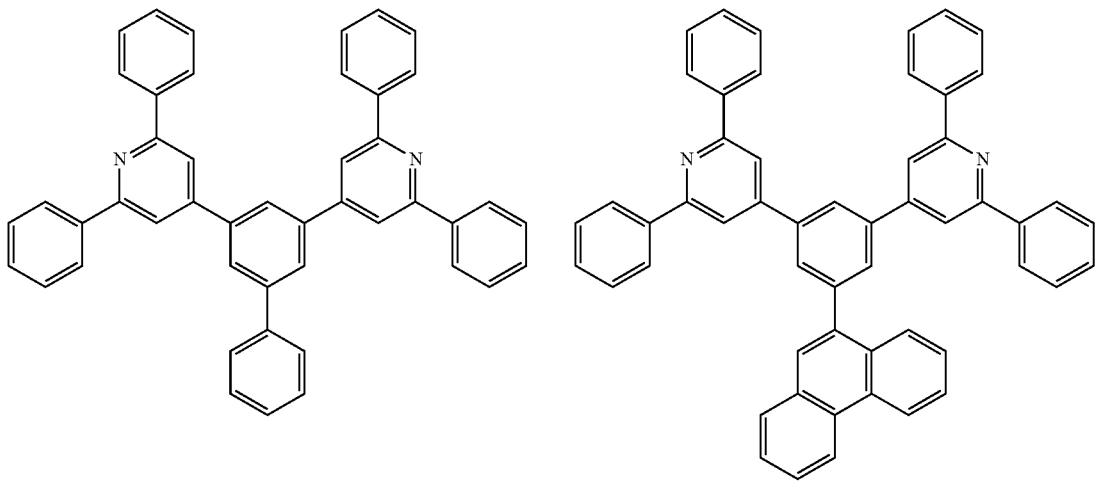
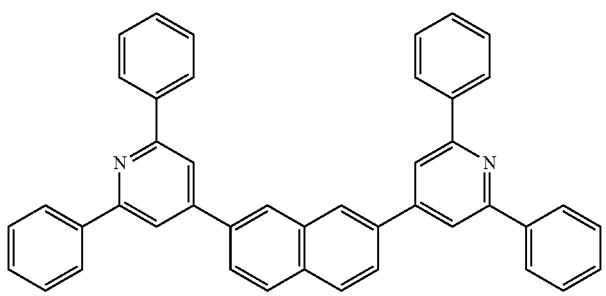
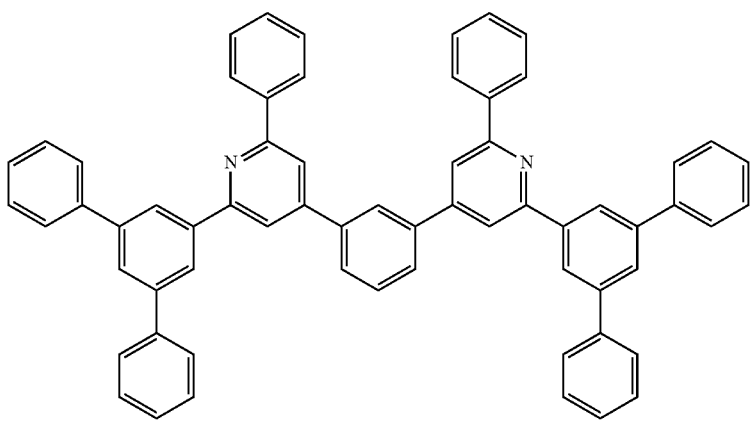

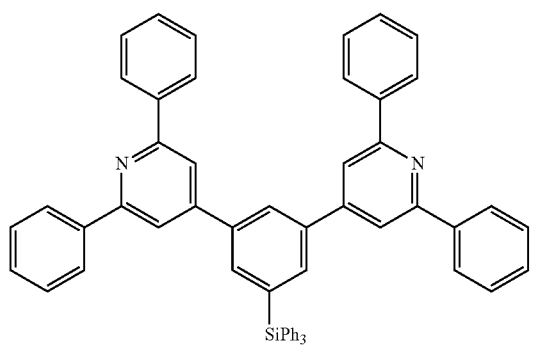
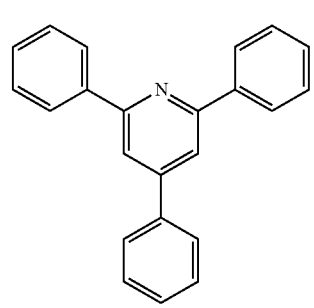
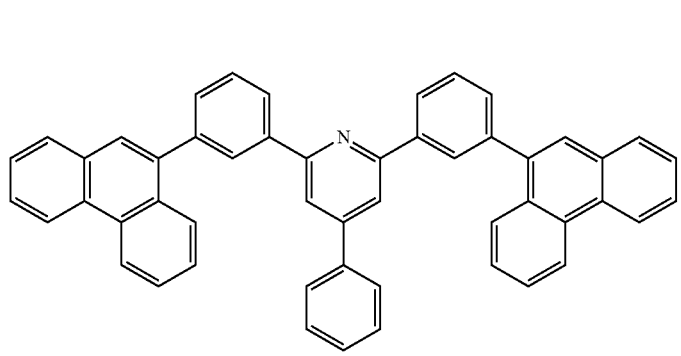
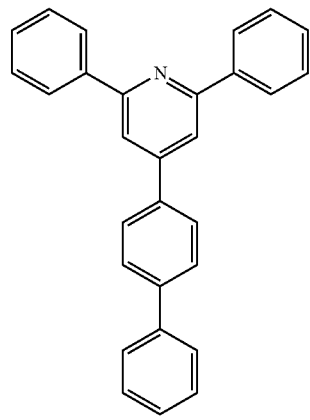
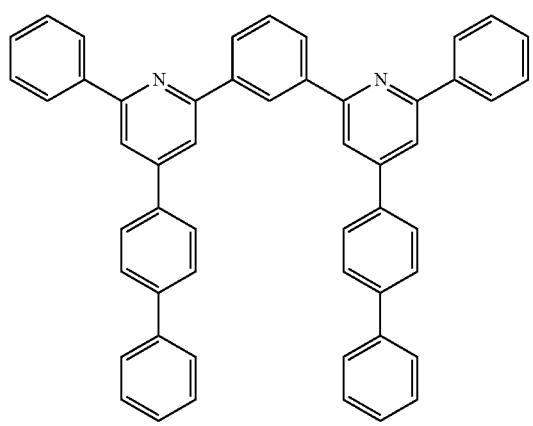
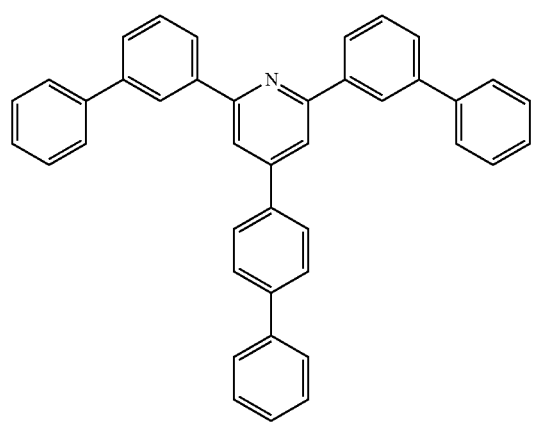

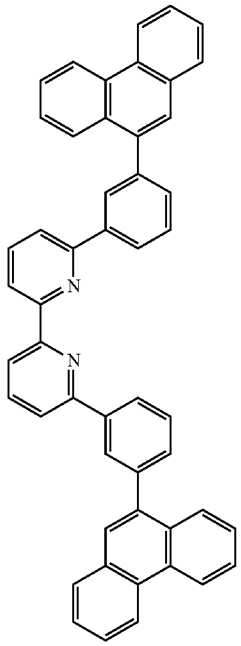
[Chem 9]
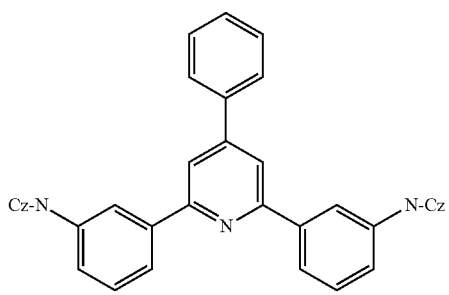 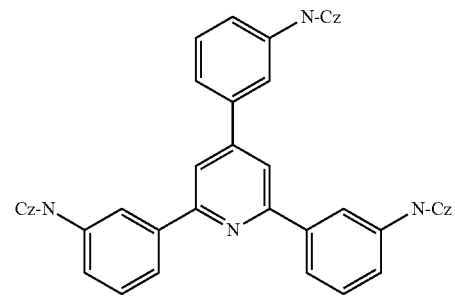
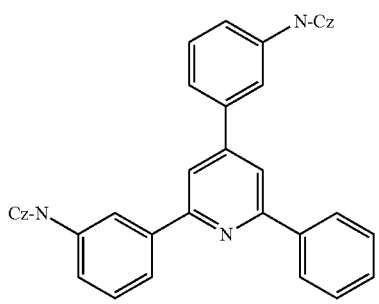 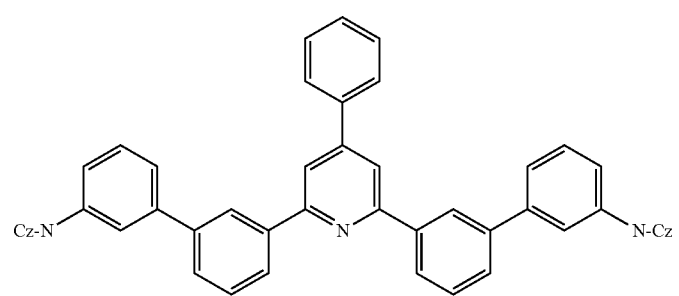
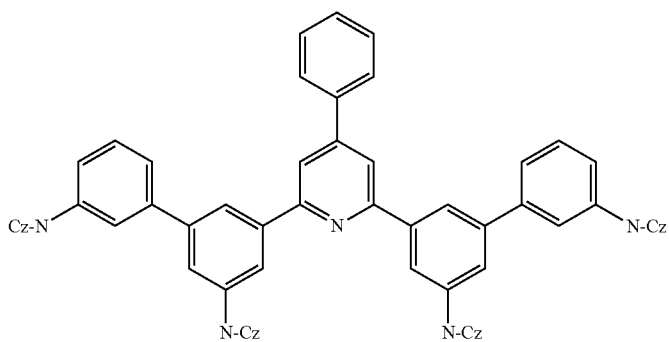

-continued
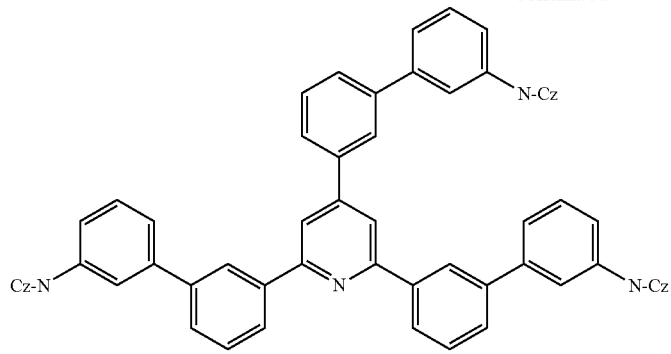
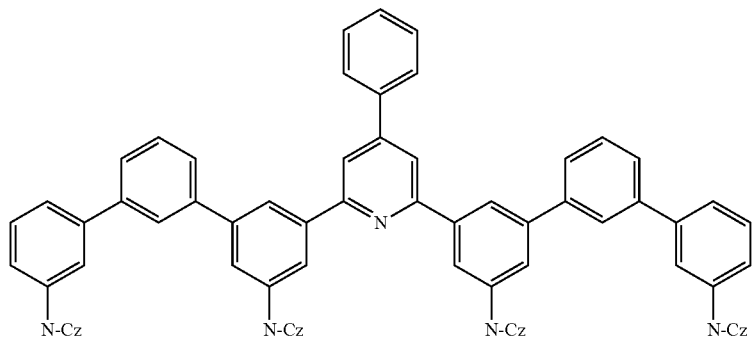
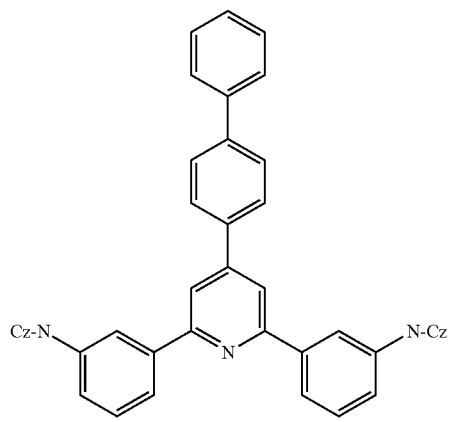
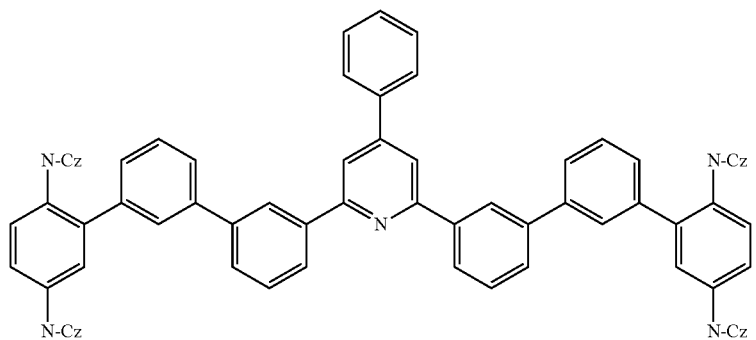

-continued
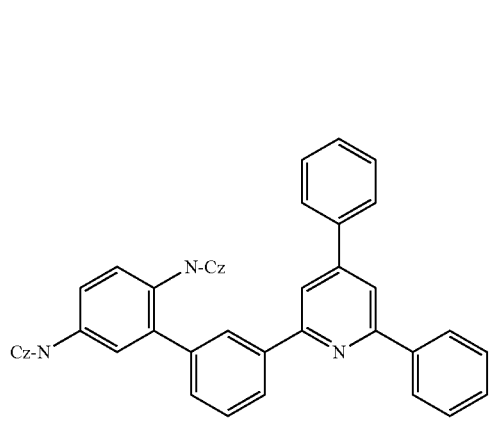
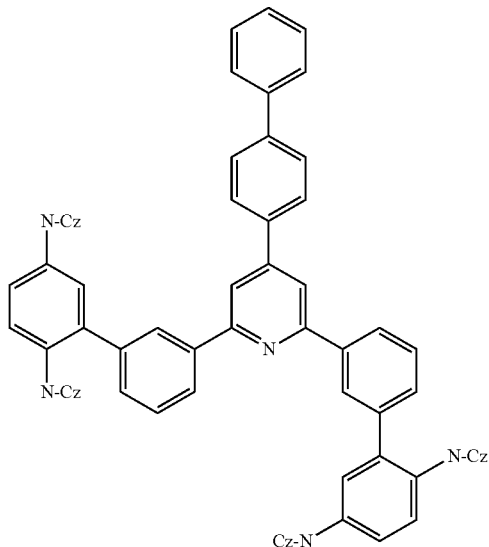
[Chem 10]
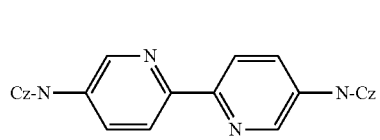 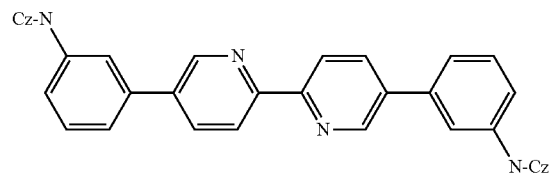
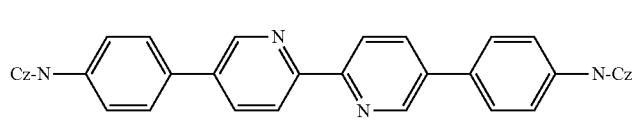 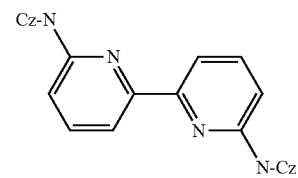
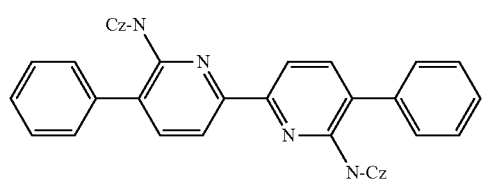 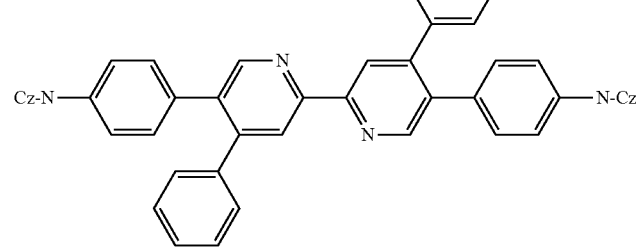
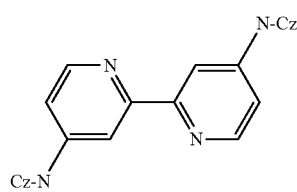 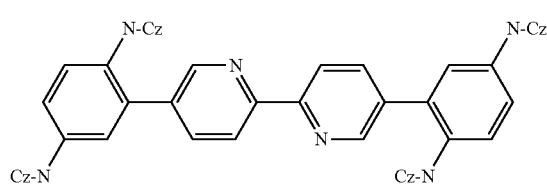
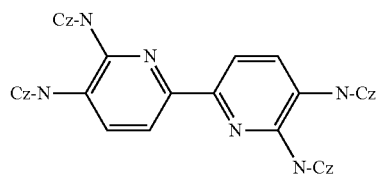 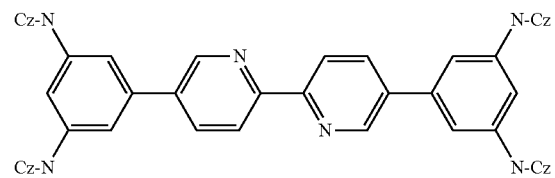

-continued
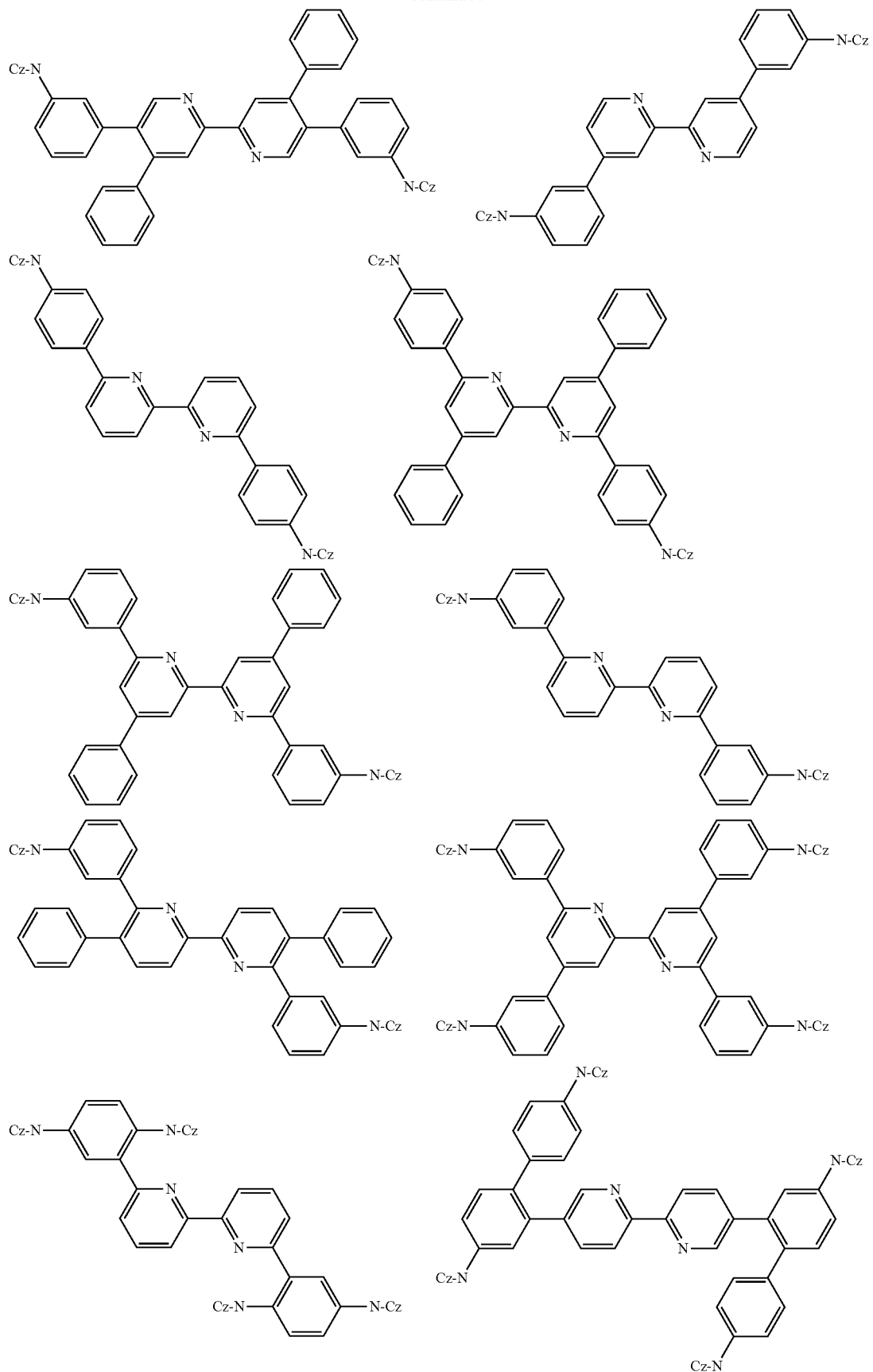

-continued
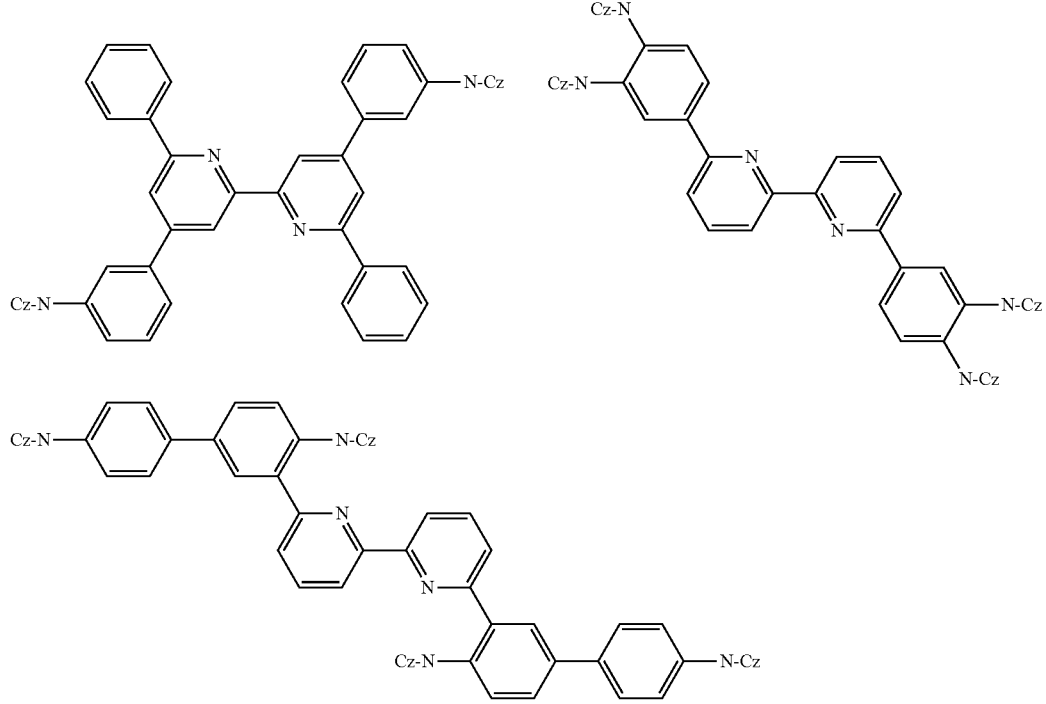
[Chem 11]
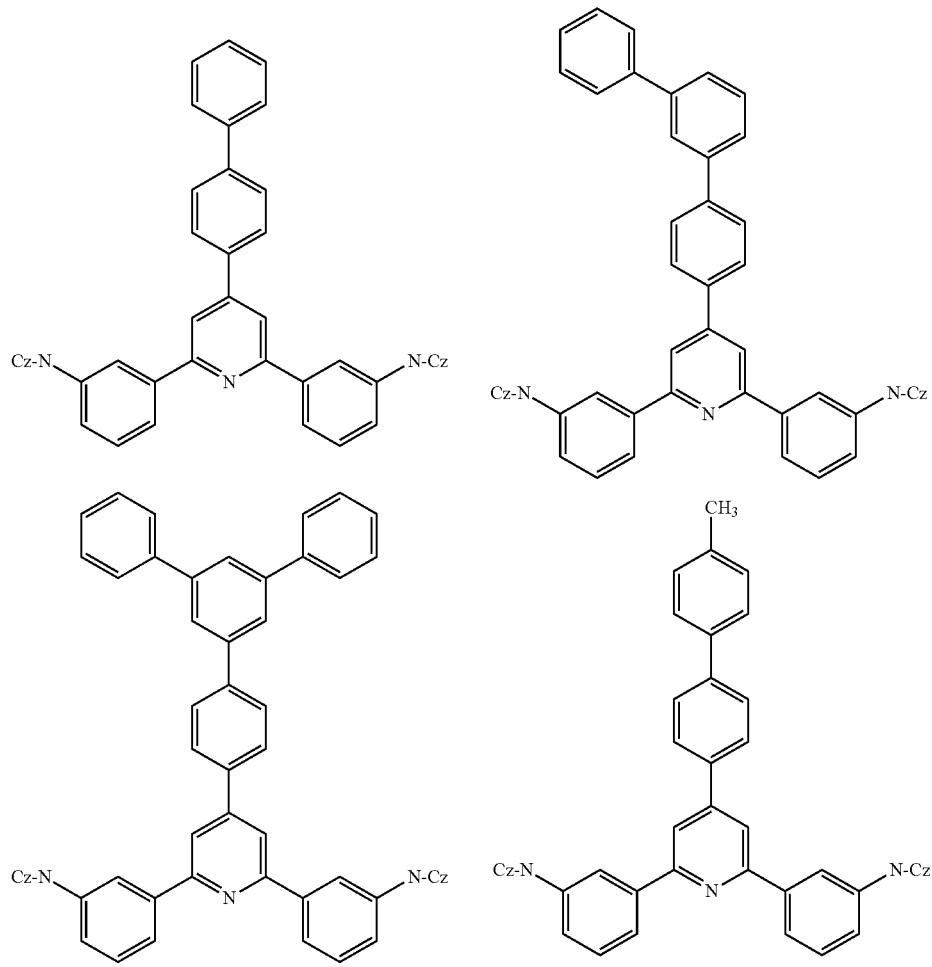

23
-continued
24
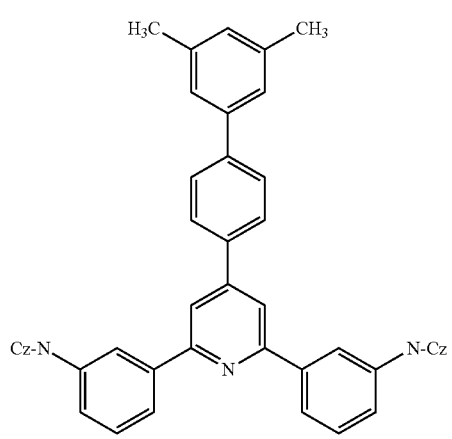
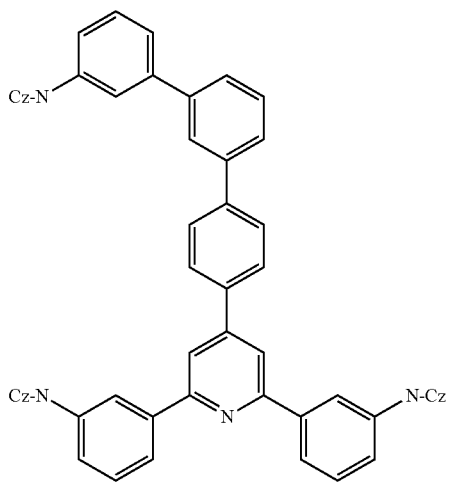
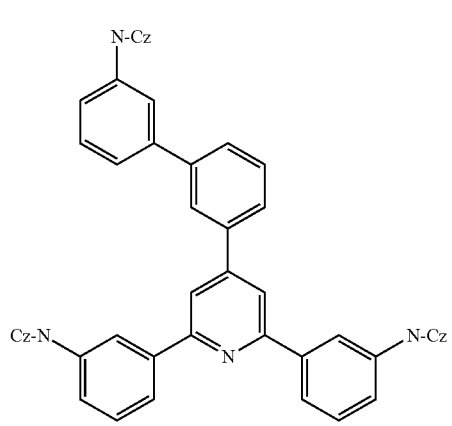
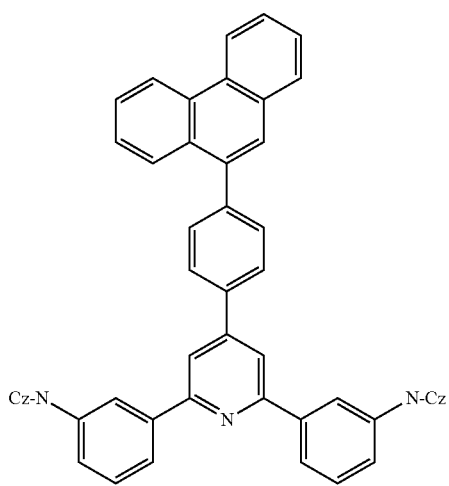
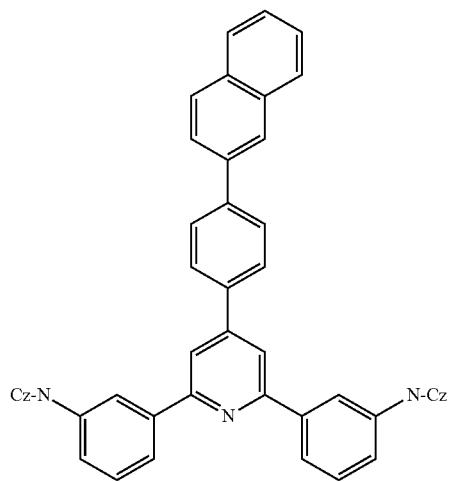

-continued
[Chem 12]
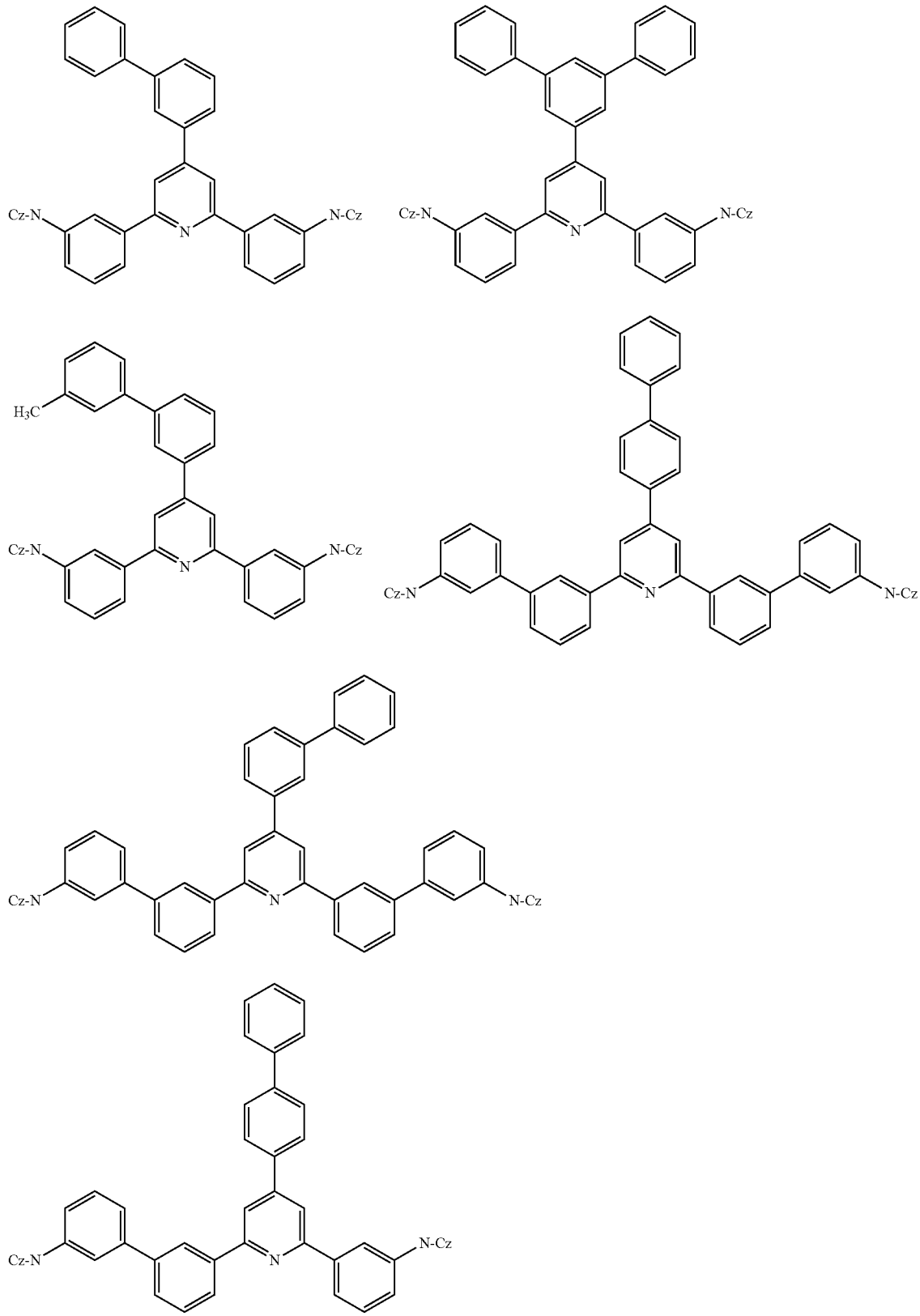

27
28
-continued
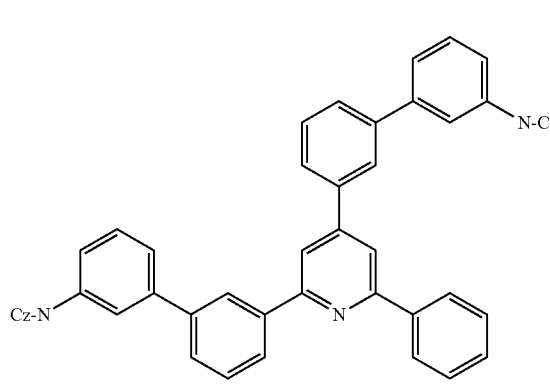
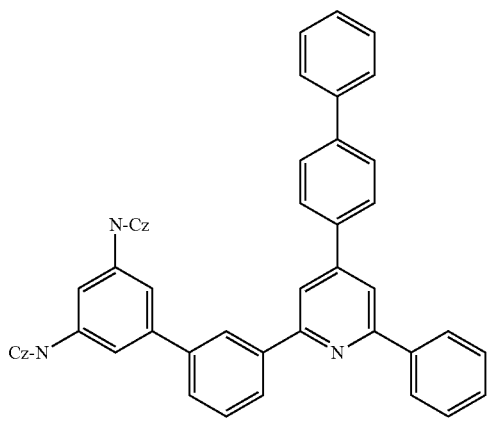
[Chem 13]
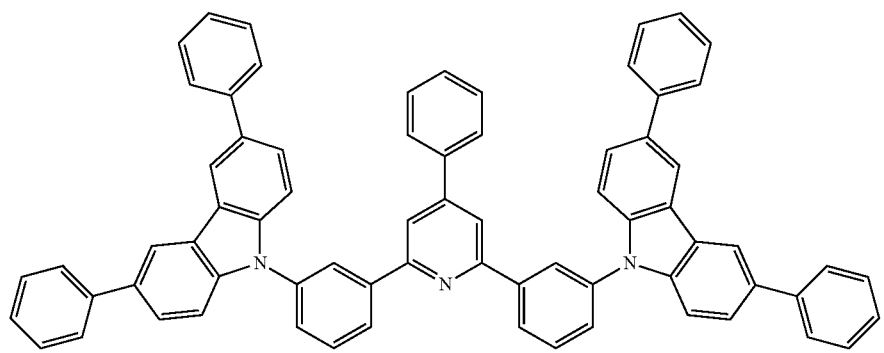
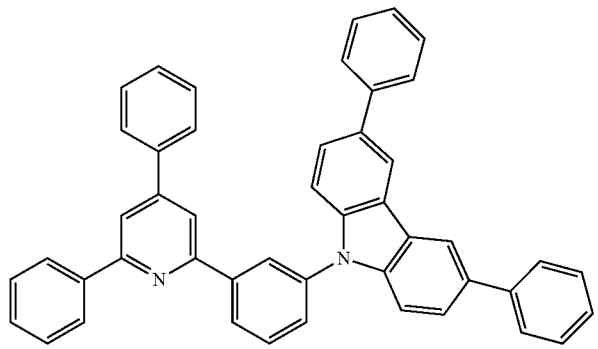
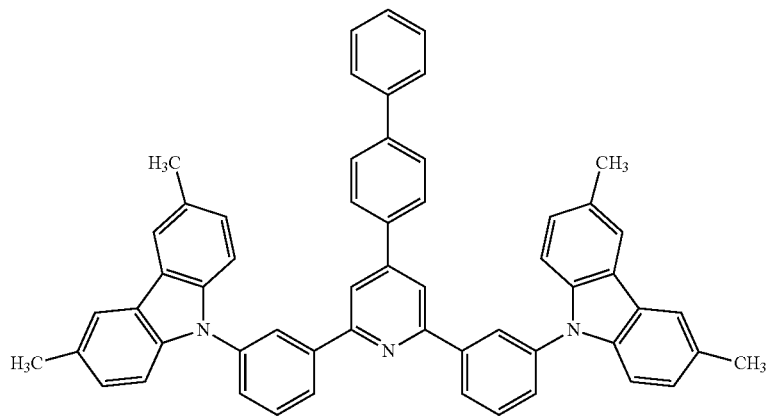

-continued
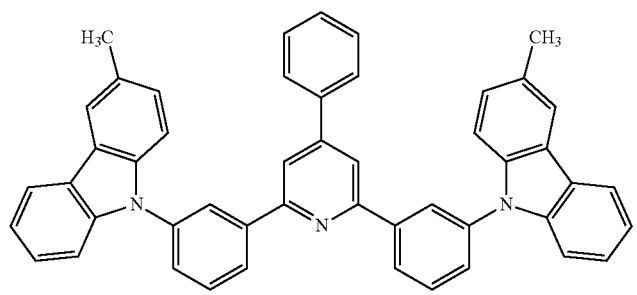
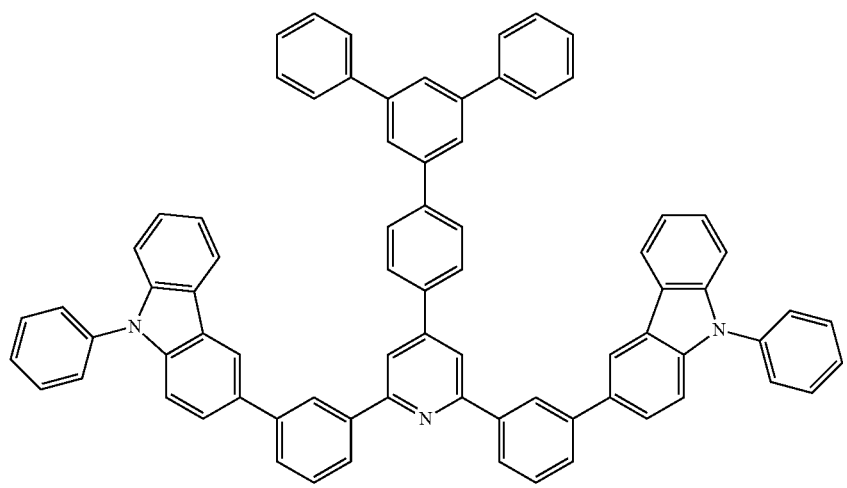
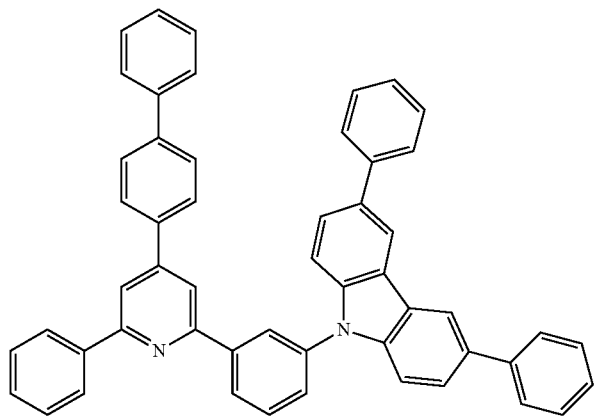
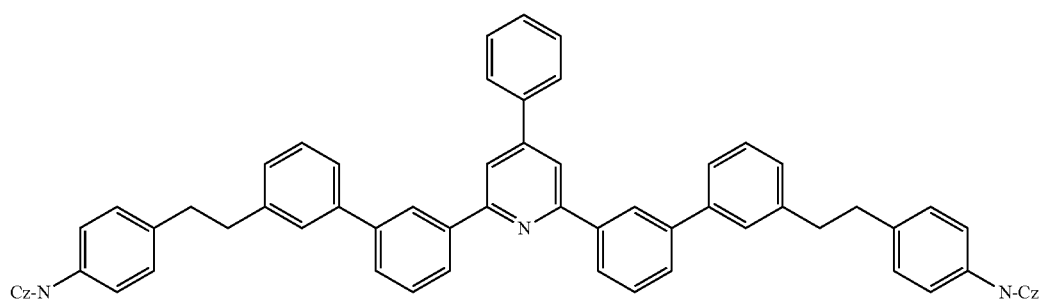

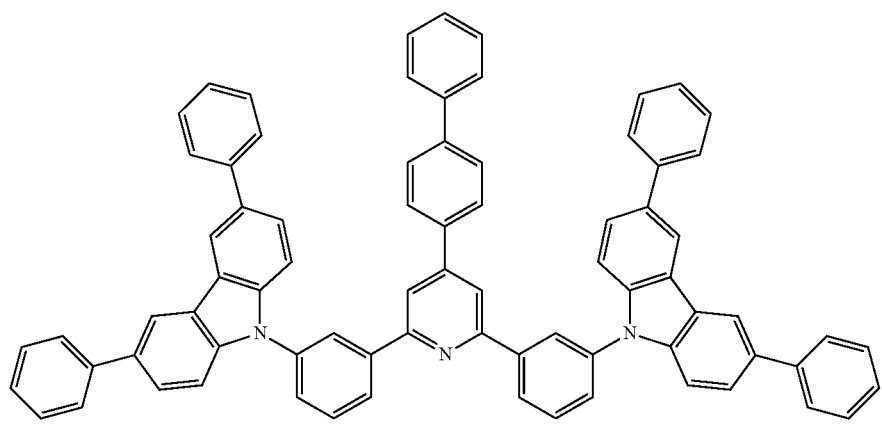
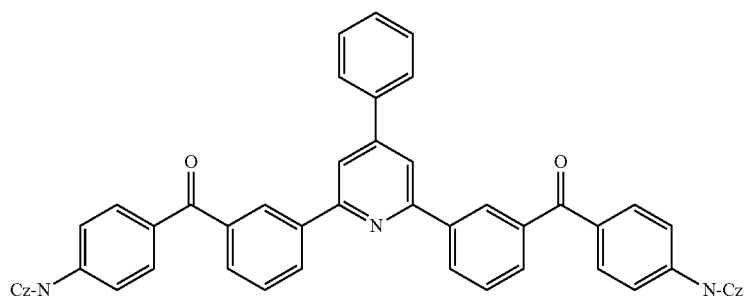
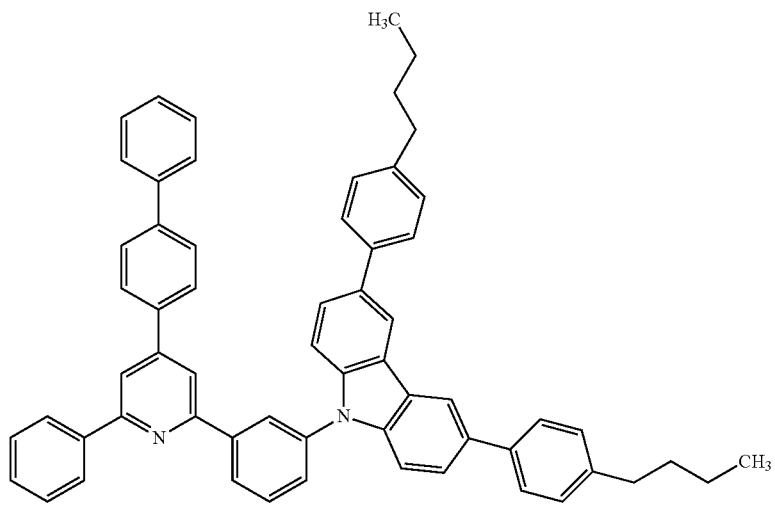

As the compound having a pyrazine ring as a partial structure, the compounds exemplified below may be mentioned. In the following structural formulae, —N-Cz represents an N-carbazolyl group.
[Chem 14]
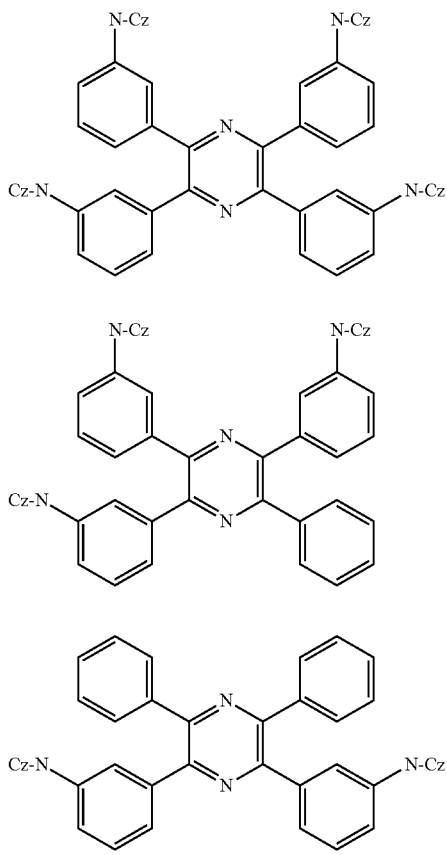
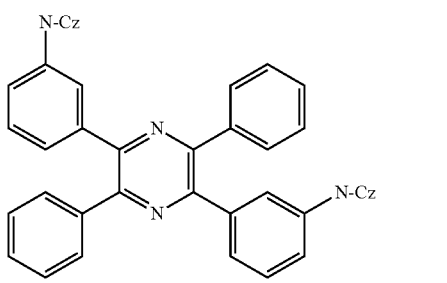
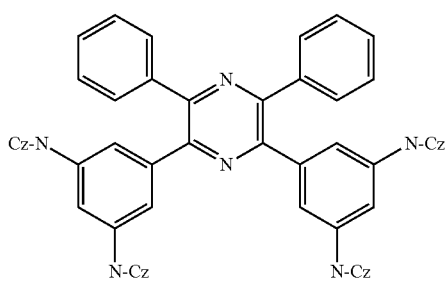
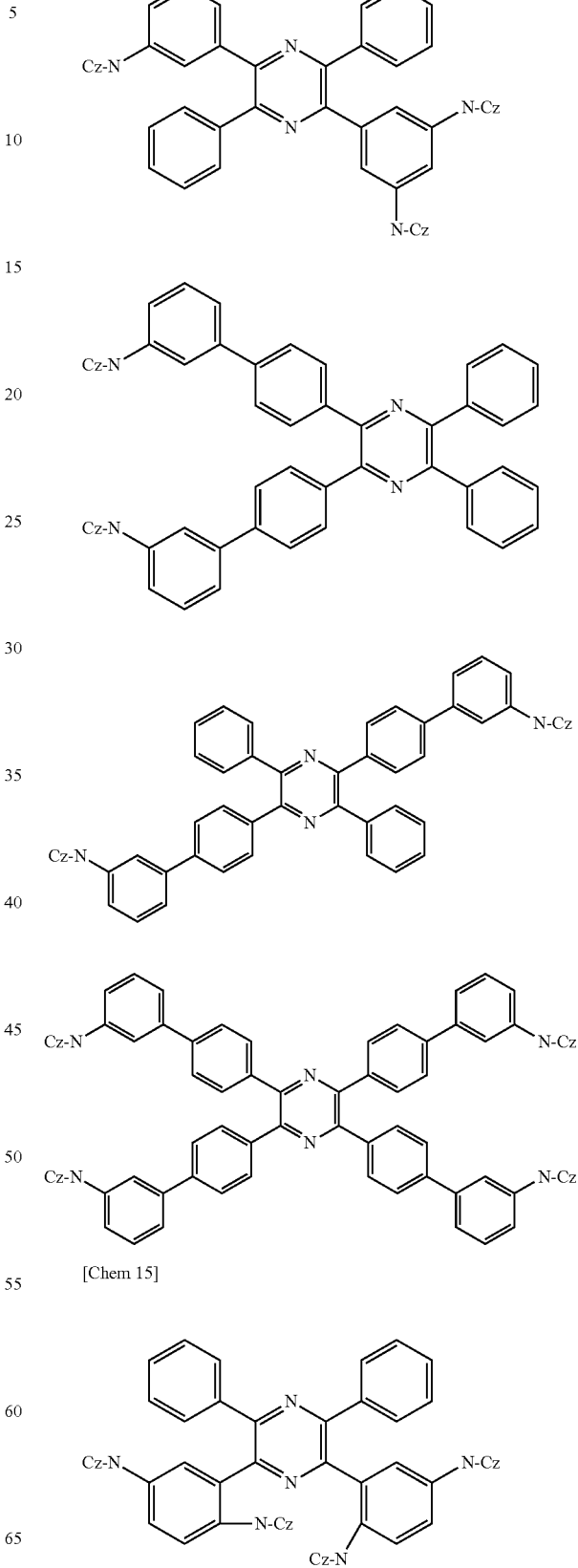
[Chem 15]
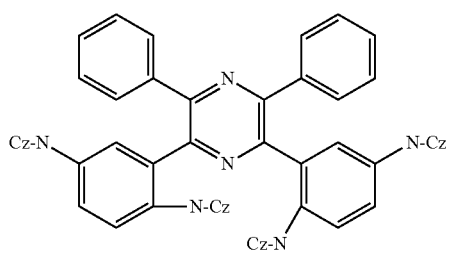

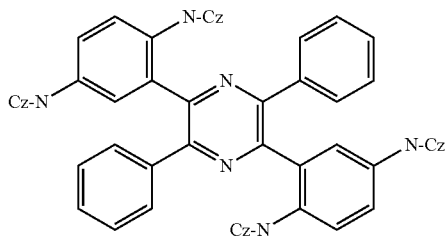
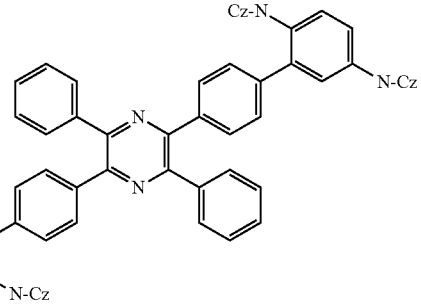
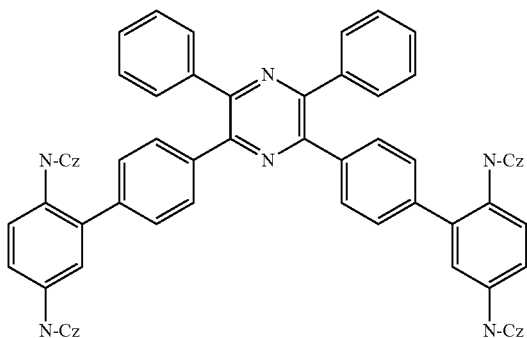
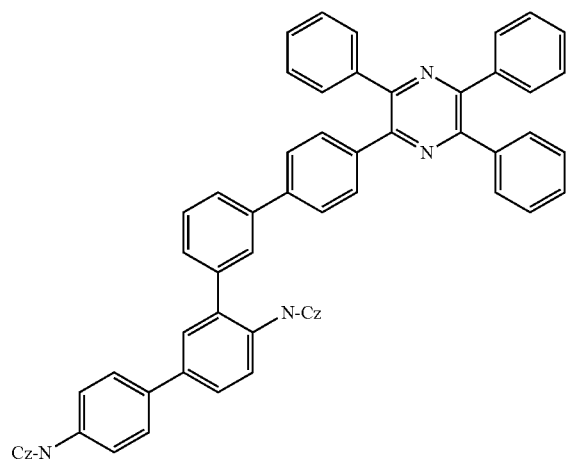
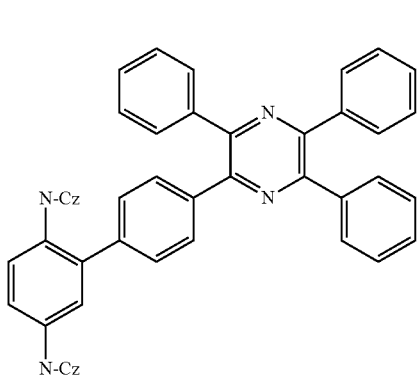
As the compound having a triazine ring as a partial structure, the compounds exemplified below may be mentioned. In the following structural formulae, —N-Cz represents an N-carbazolyl group.
[Chem 16]
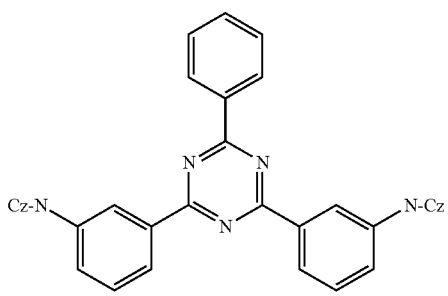
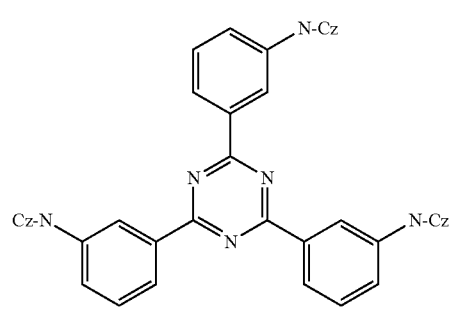

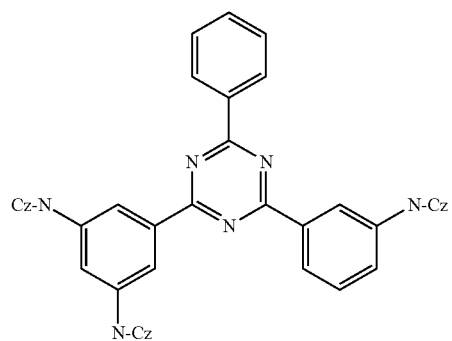
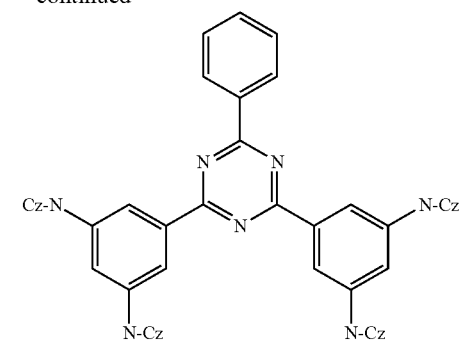
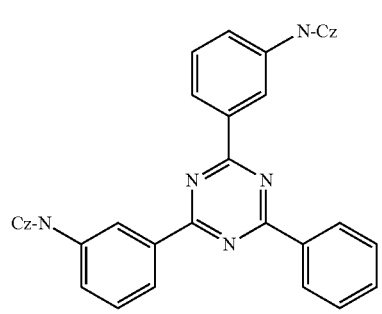
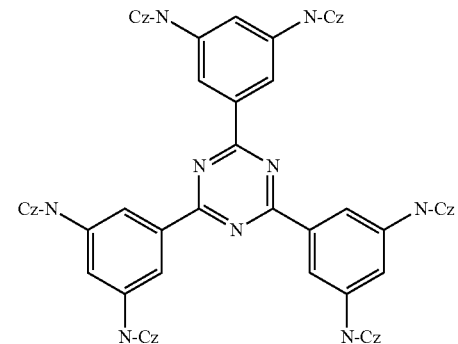
[Chem 17]
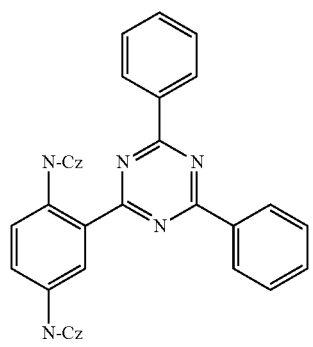
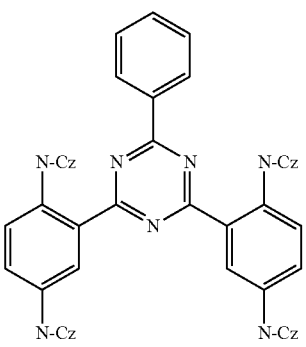
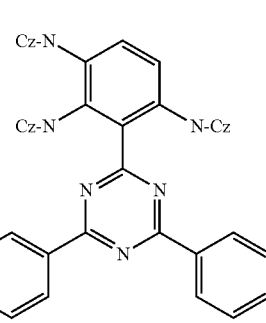
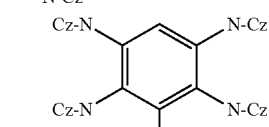
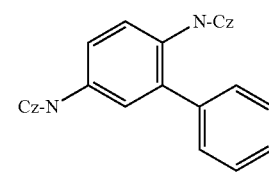
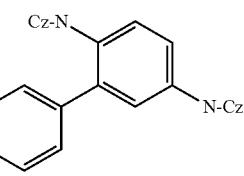
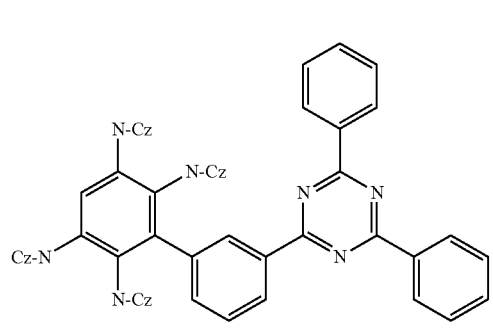
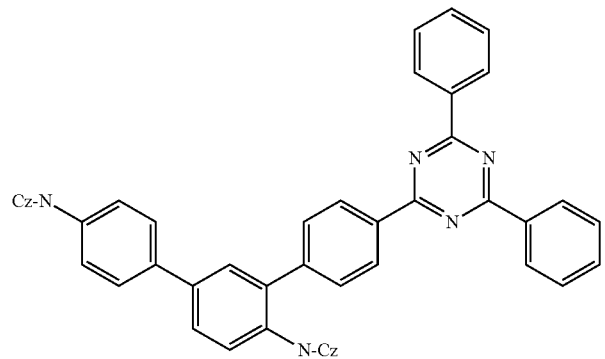

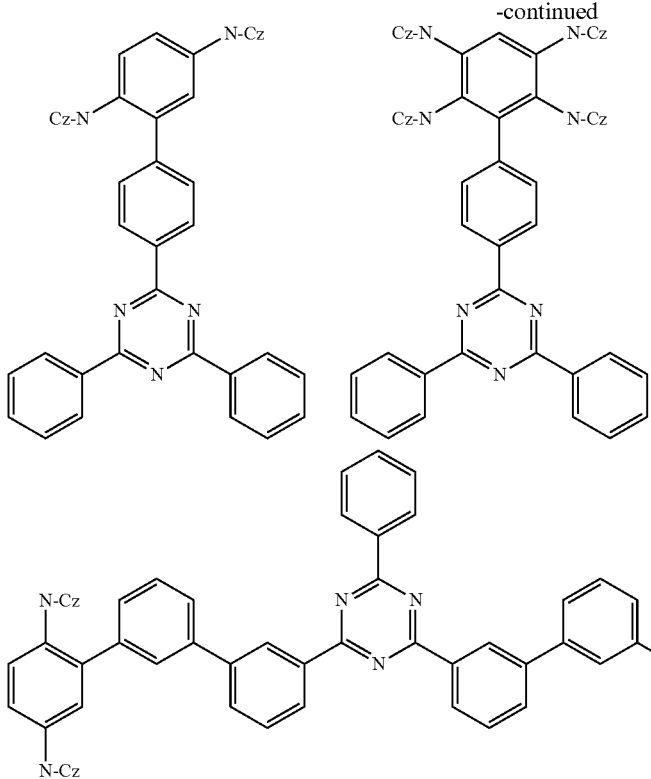
-continued
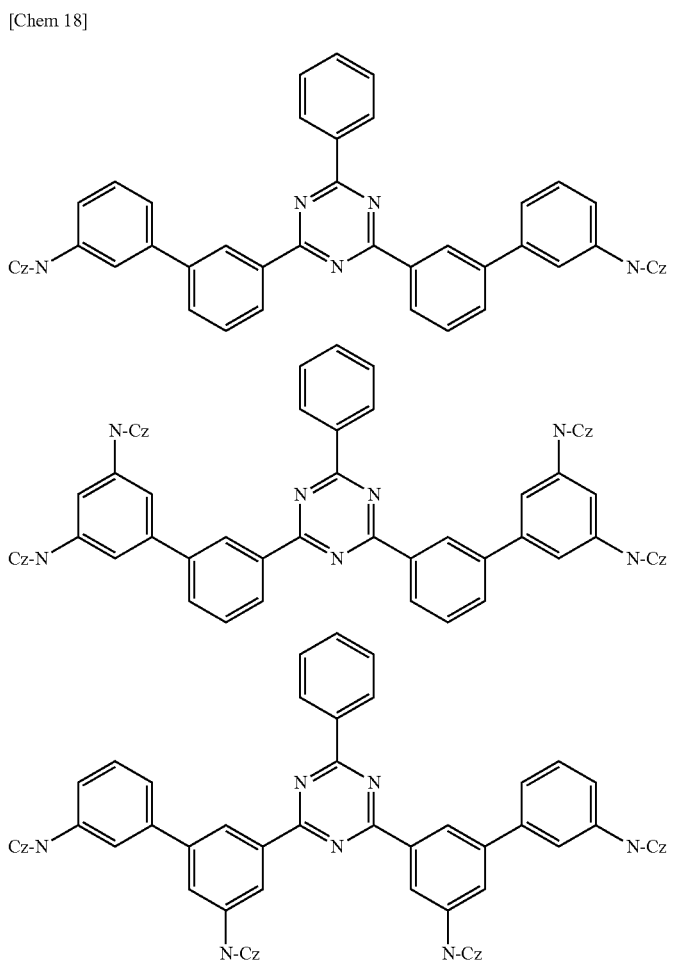

-continued
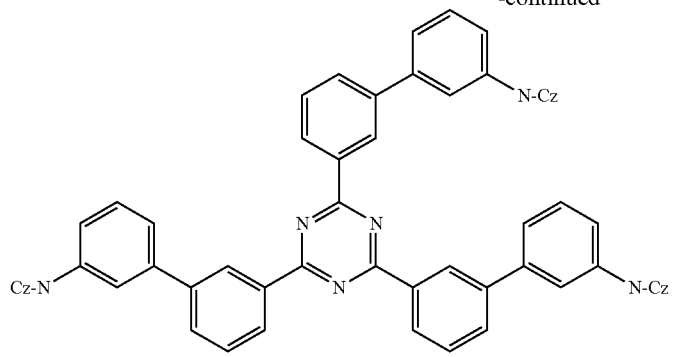
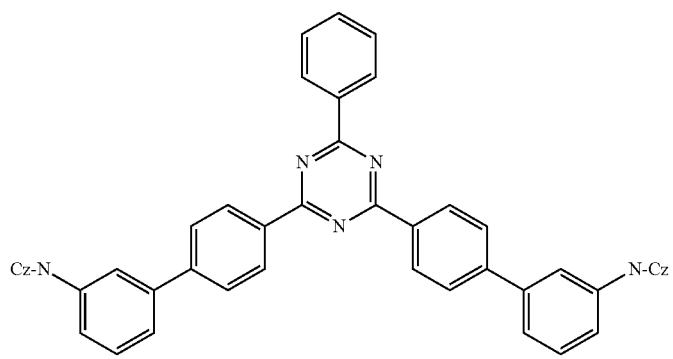
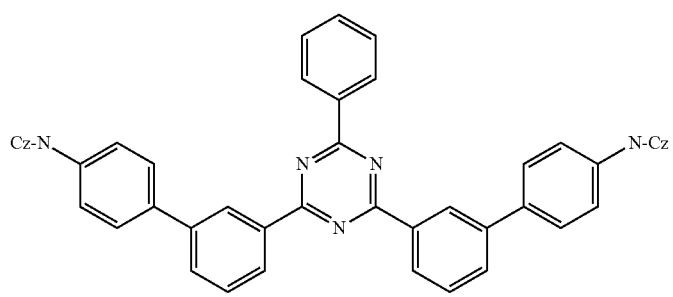
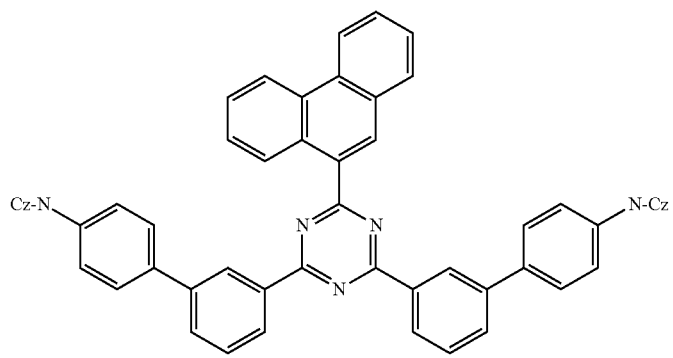

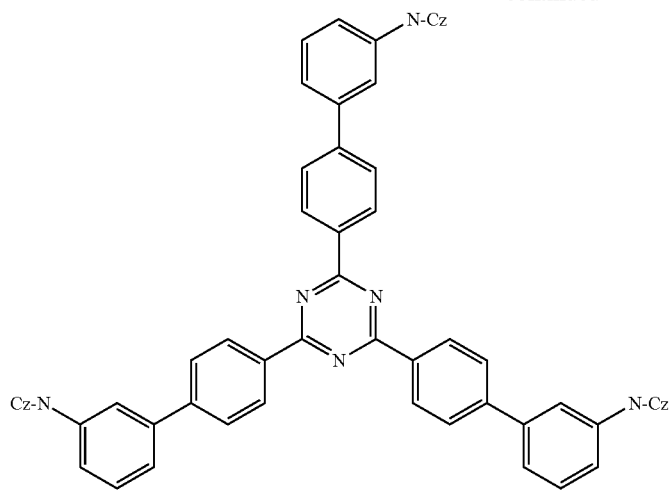
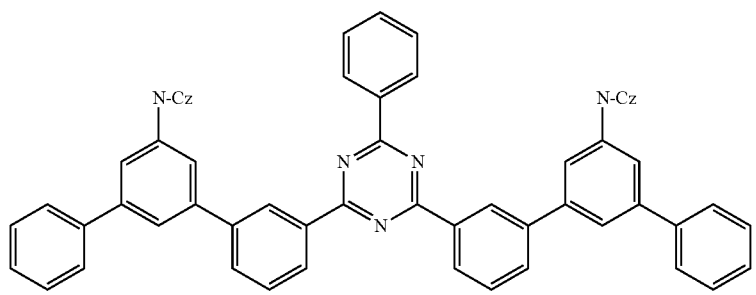
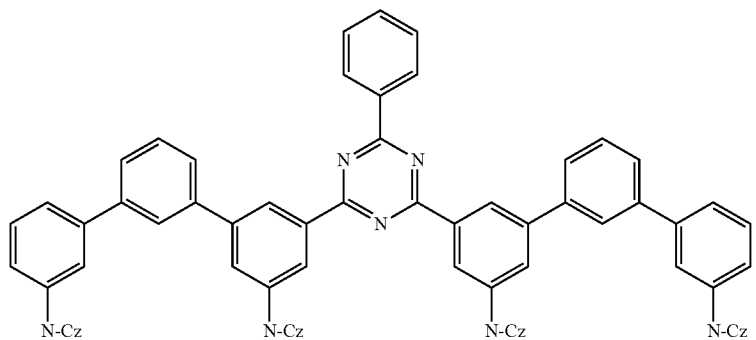
[Chem 19]
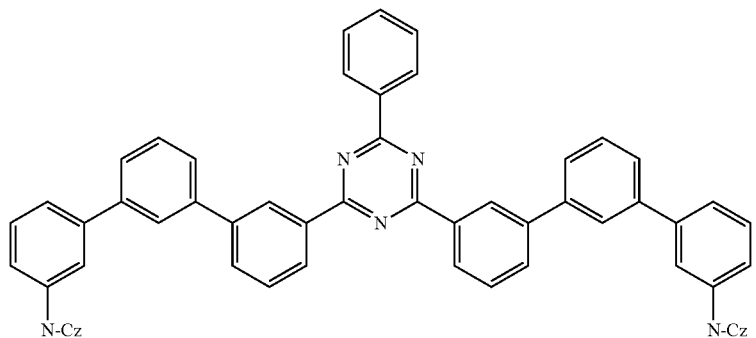

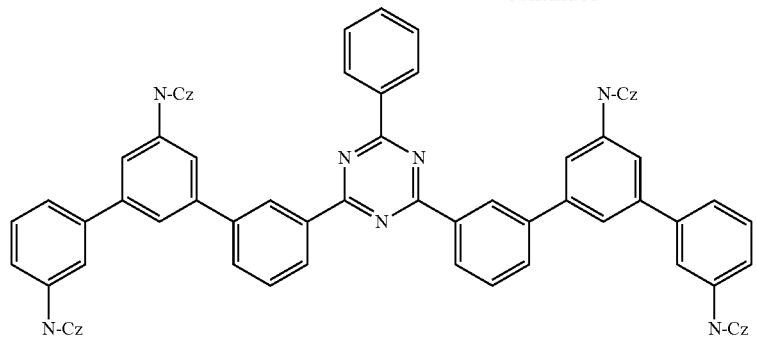
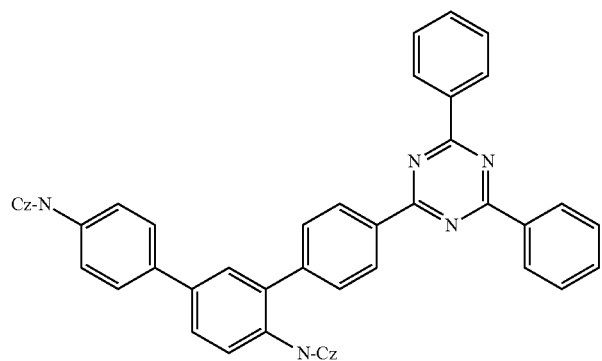
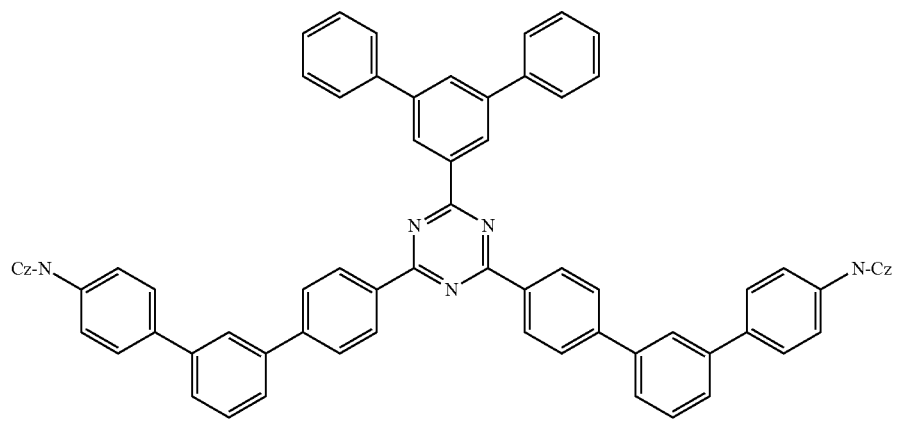
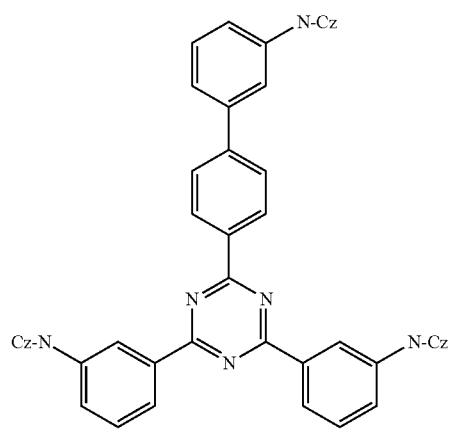

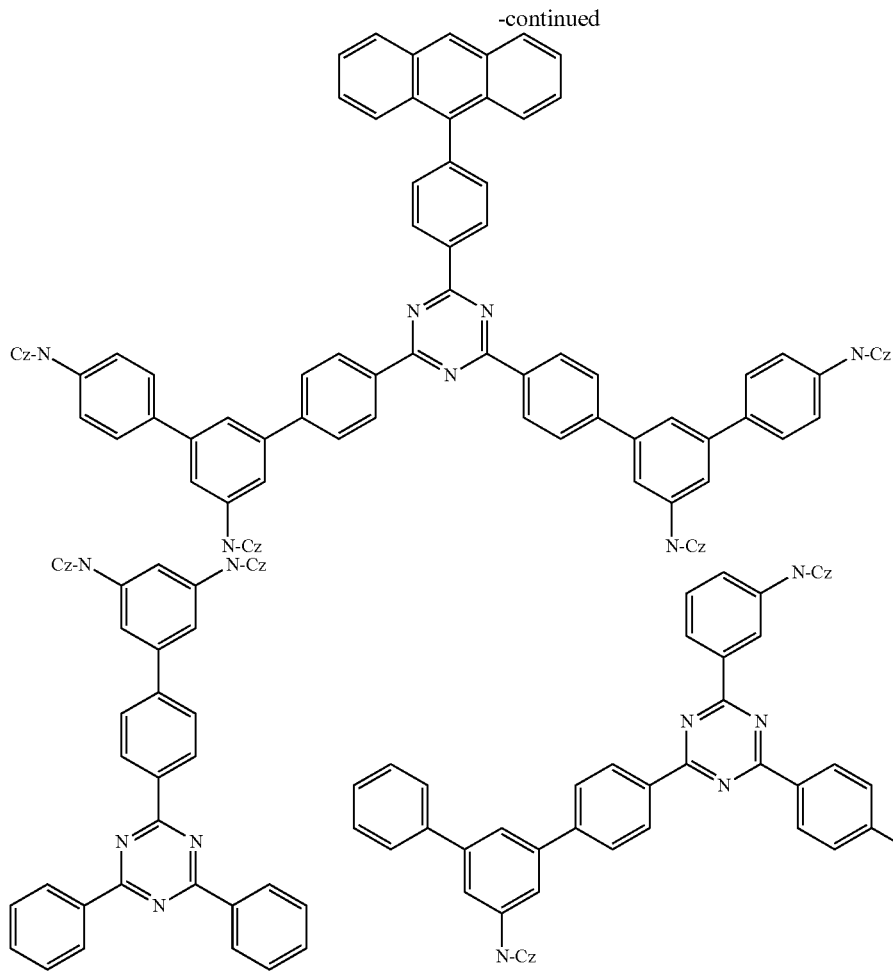

2. Monoamine Compound

In the invention, the hole transport layer contains the monoamine compound represented by the following formula (I).

[Chem 20]

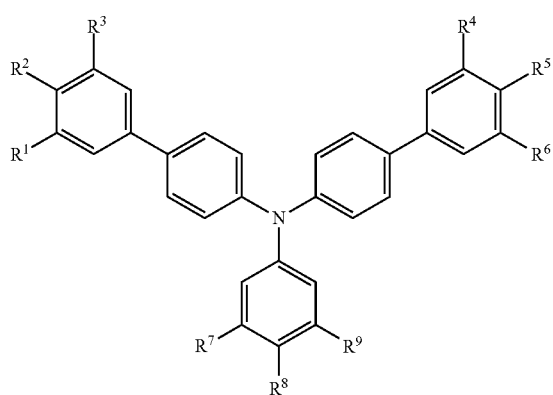

wherein $R^1$ to $R^9$ represent a hydrogen atom, an aryl group, or an alkyl group; and $R^1$ to $R^9$ may be the same or different from each other.

Examples of the aryl group include a monovalent group derived from a 6-membered monocyclic ring or 2 to 5 condensed rings, such as a benzene ring, a naphthalene ring, an anthracene ring, a phenanthrene ring, a perylene ring, a tetracene ring, a pyrene ring, a benzpyrene ring, a chrysene ring, a triphenylene ring or a fluoranthene ring or a monovalent group formed by combining plurality of them (for example, a biphenyl group, a terphenyl group, and the like). More preferred is a monovalent group formed by combining 1 to 10 benzene rings, such as a phenyl group, a biphenyl group, or a terphenyl group.

The alkyl group is a linear or branched alkyl group having preferably 1 or more carbon atoms and 28 or less carbon atoms, more preferably 20 or less carbon atoms, particularly preferably 4 or less carbon atoms and examples thereof include methyl, ethyl, n-propyl, 2-propyl, n-butyl, isobutyl, tert-butyl, and the like groups.

When $R^1$ to $R^9$ are an aryl group or an alkyl group, they may further have an aryl group or an alkyl group as a substituent.

Preferable examples of the aryl group include a monovalent group derived from a 6-membered monocyclic ring or 2 to 5 condensed rings, such as a benzene ring, a naphthalene ring, an anthracene ring, a phenanthrene ring, a perylene ring, a tetracene ring, a pyrene ring, a benzpyrene ring, a chrysene ring, a triphenylene ring or a fluoranthene ring or a monovalent group formed by combining plurality of them (for example, a biphenyl group, a terphenyl group, and the like).

More preferred is a monovalent group formed by combining 1 to 8 benzene rings, such as a phenyl group, a biphenyl group, or a terphenyl group.

The alkyl group is a linear or branched alkyl group having preferably 1 or more carbon atoms and 20 or less carbon atoms and examples thereof include methyl, ethyl, n-propyl, 2-propyl, n-butyl, isobutyl, tert-butyl, and the like groups.

In view of enhancing electric durability and thermal durability, particularly, the compound represented by the formula (I) is preferably a compound comprising an N atom and an aryl group, more preferably a compound comprising an N atom and a phenyl group (a benzene ring).

Moreover, in view of enhancing electric durability, in the compound represented by the formula (I), further, $R^8$ is preferably a phenyl group which optionally has a substituent.

Furthermore, in view of enhancing amorphous property and durability against electric reduction, the compound represented by the formula (I) is preferably has a partial structure represented by the following formula (I-1) in the molecule.

[Chem 21]

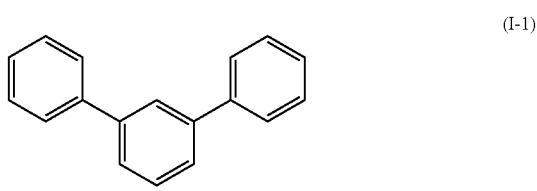

(I-1)

Additionally, in the compound represented by the formula (I), the three groups which are combined with the N atom are preferably the same including their substituents.

As the monoamine compound represented by the formula (I), specifically, the following compounds may be mentioned.

[Chem 22]

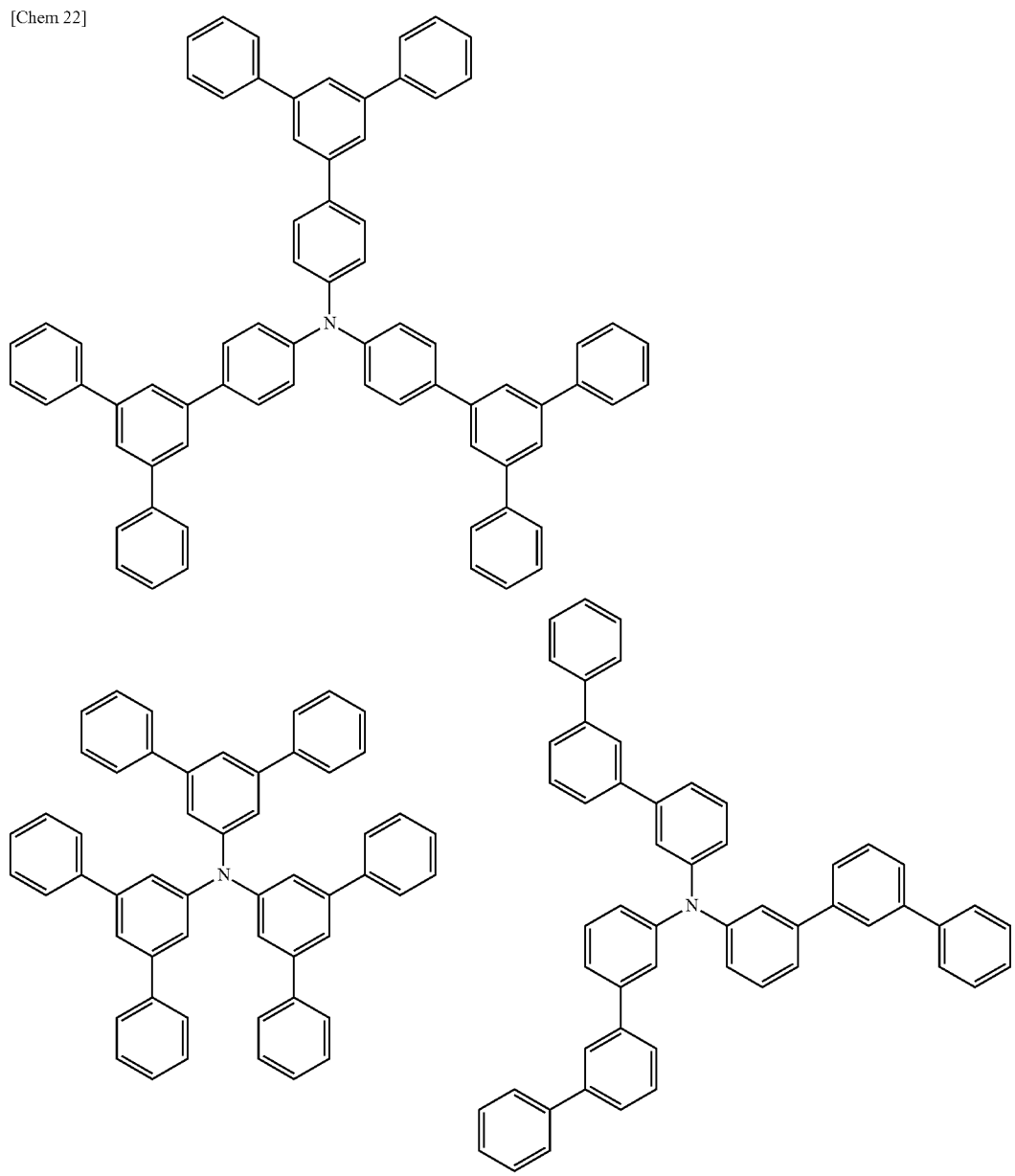

-continued
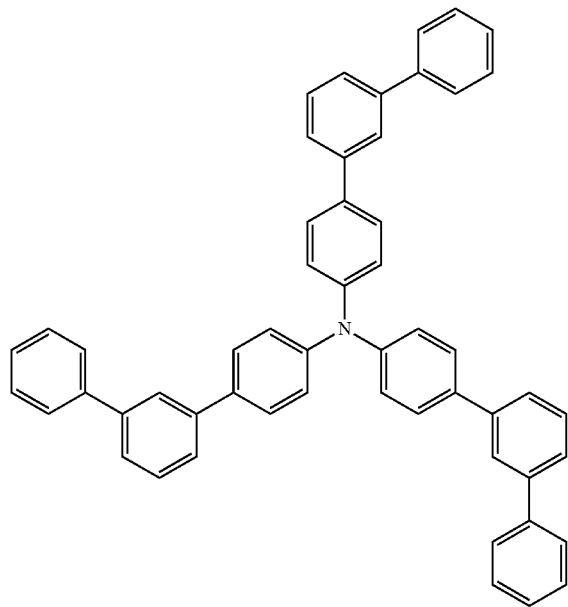
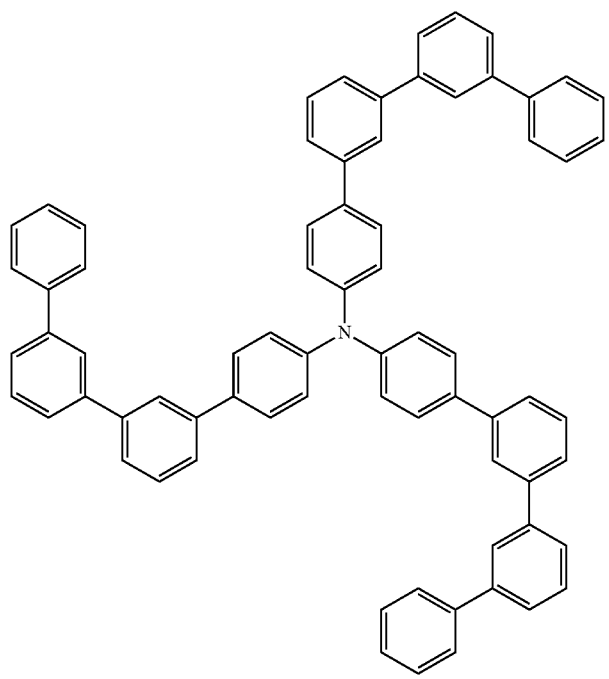

[Chem 23]
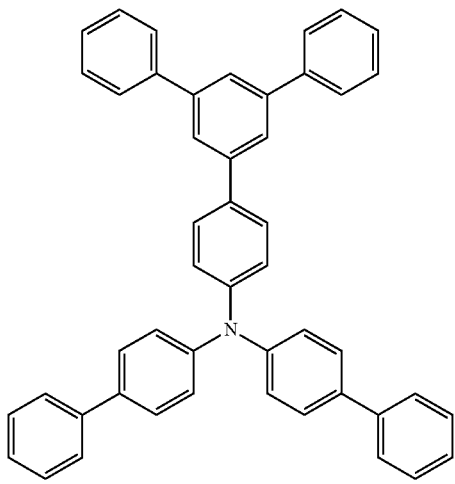 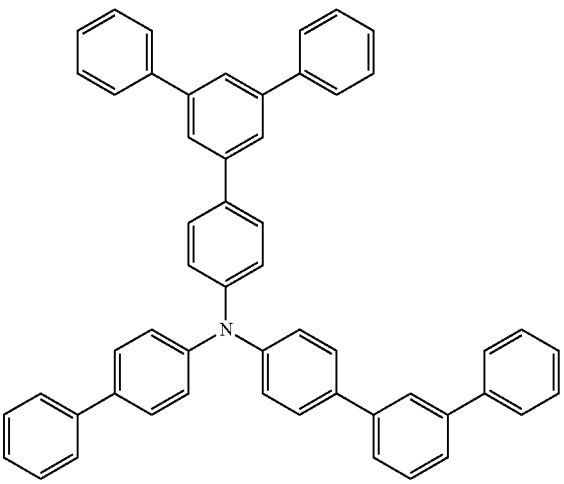
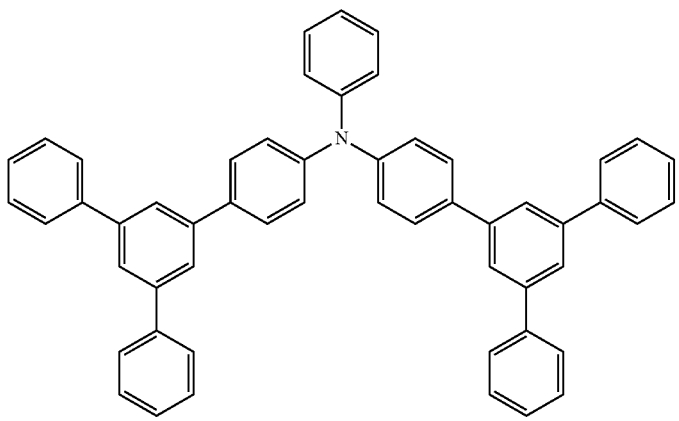
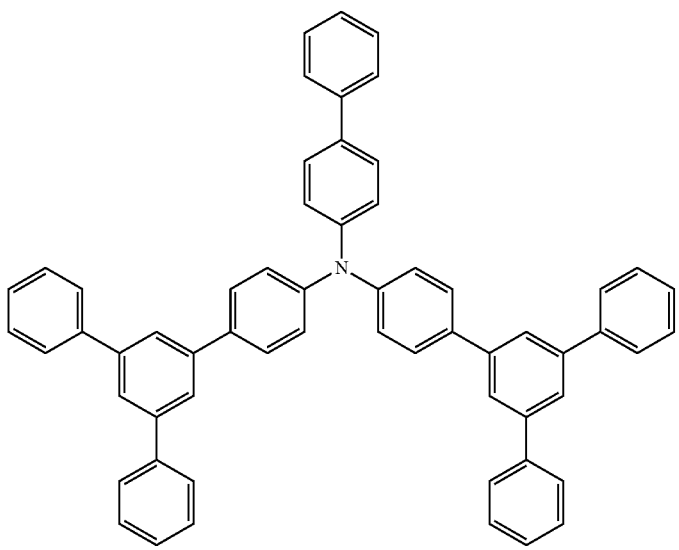

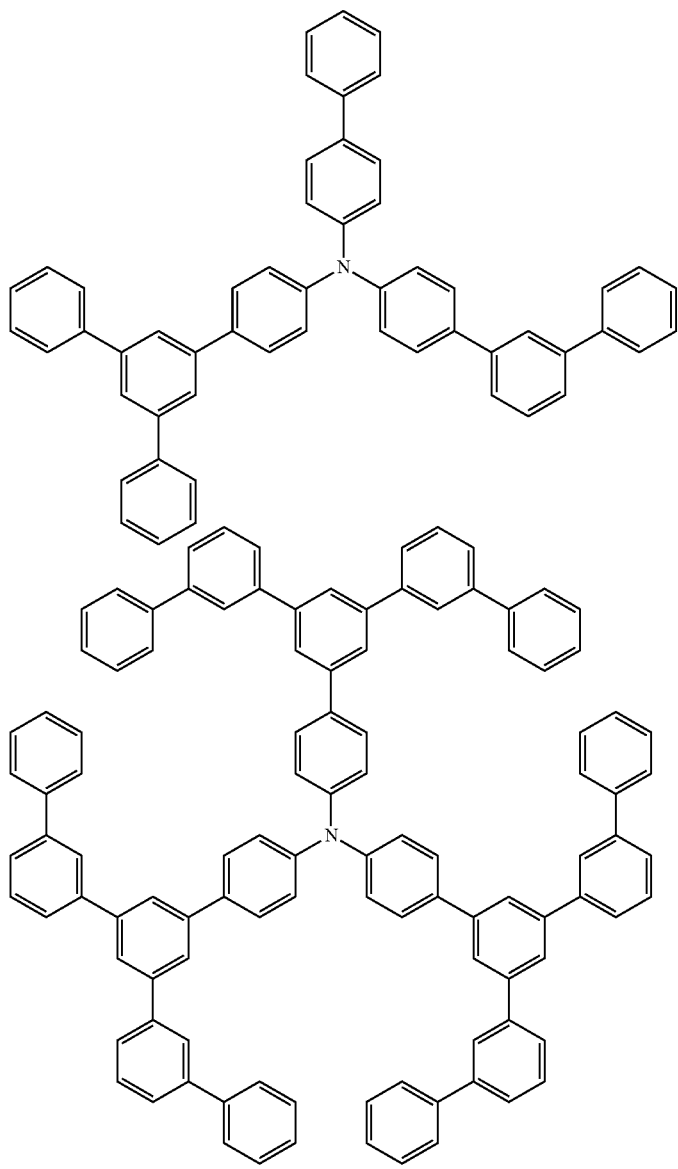
[Chem 24]
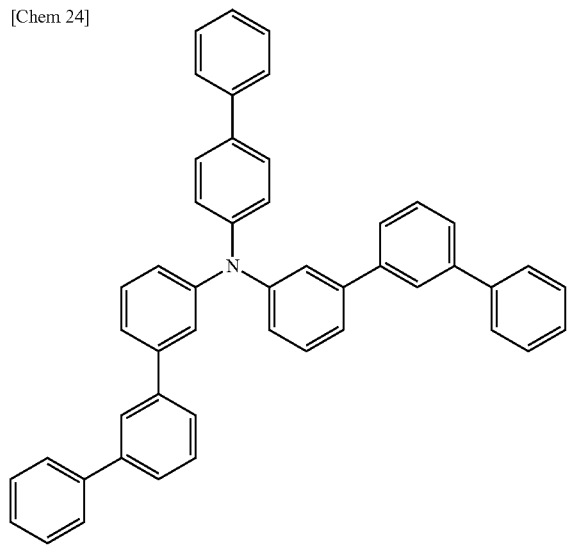

-continued
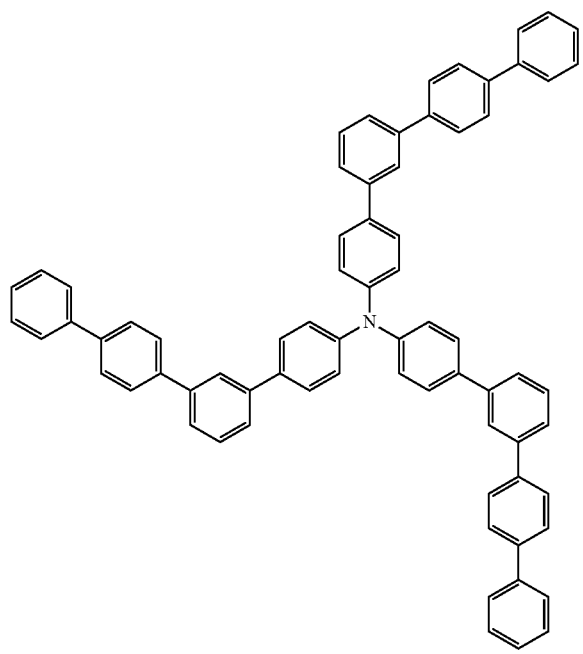
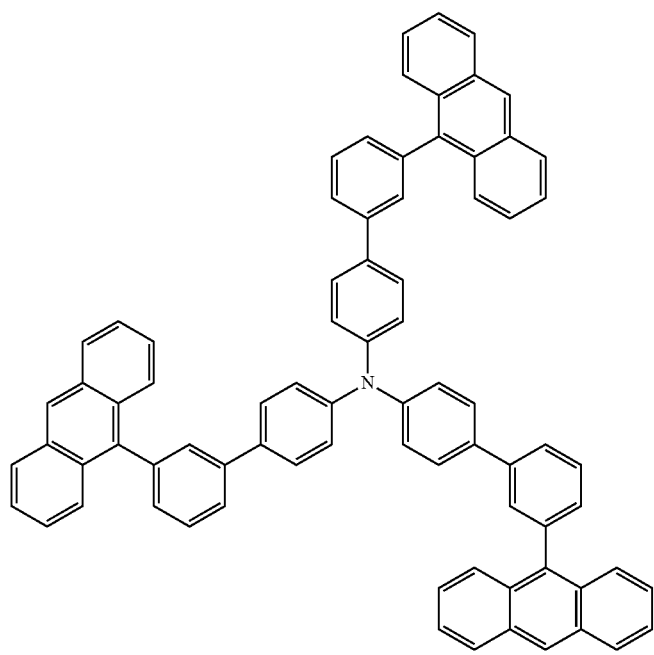

-continued
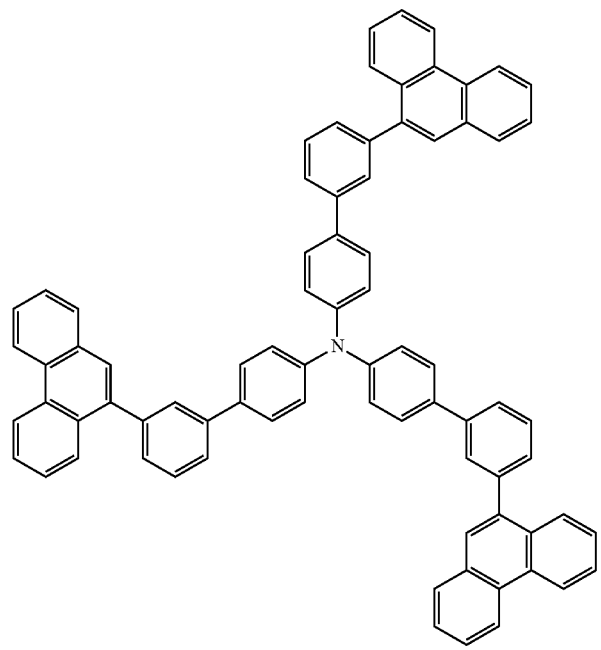
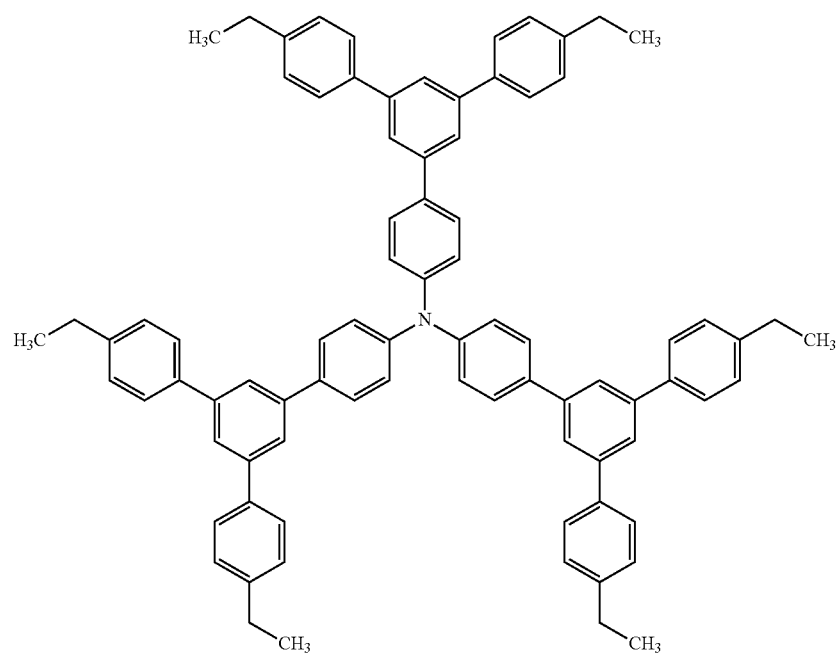

-continued
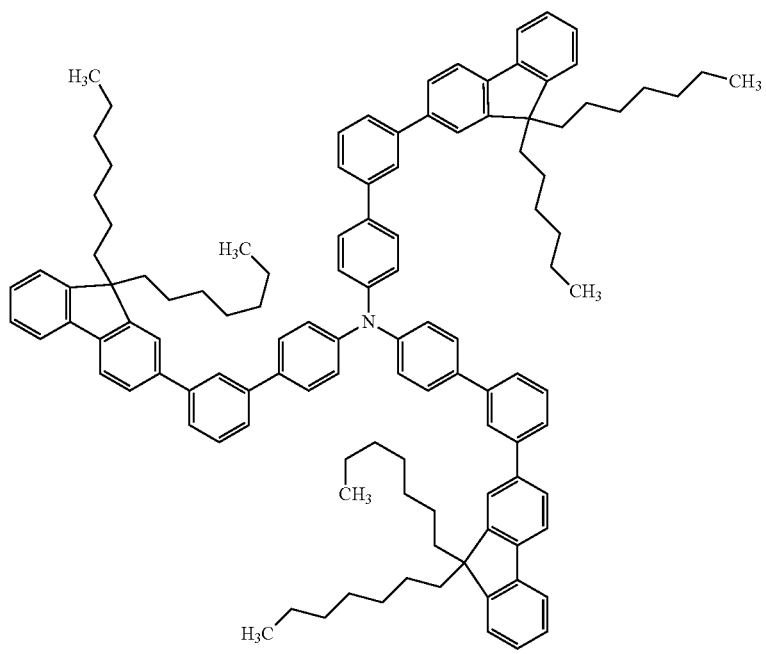
[Chem 25]
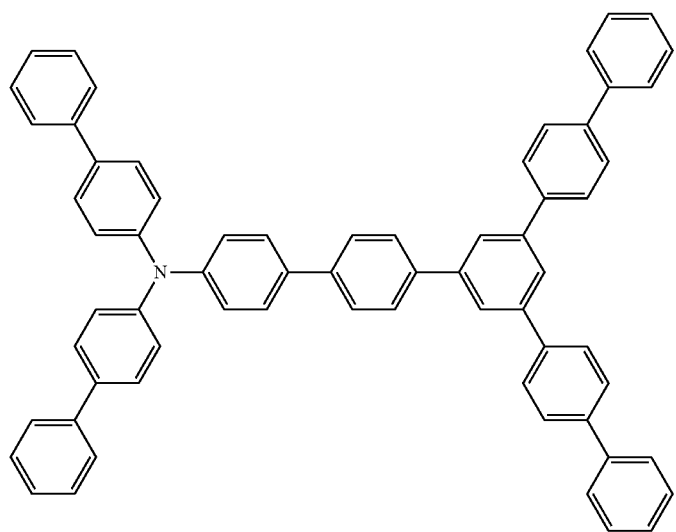

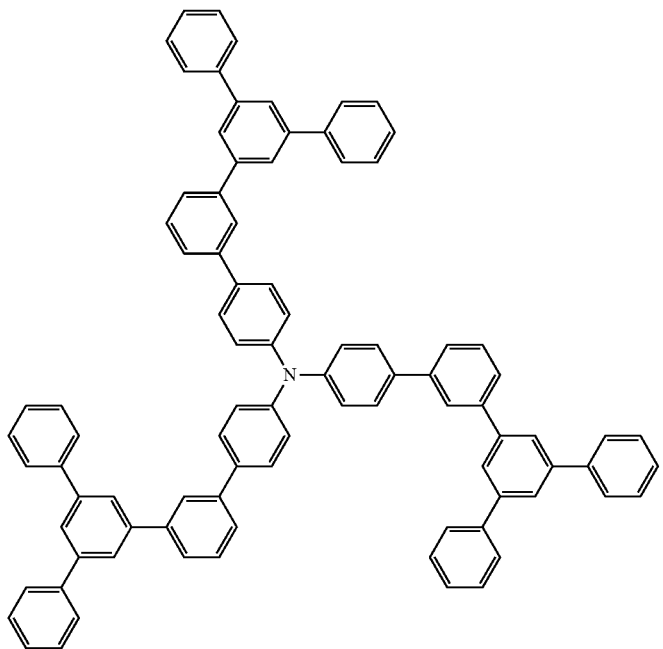
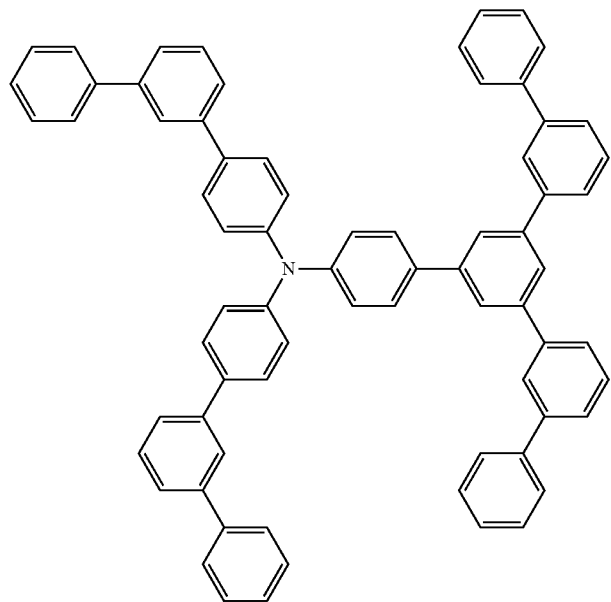

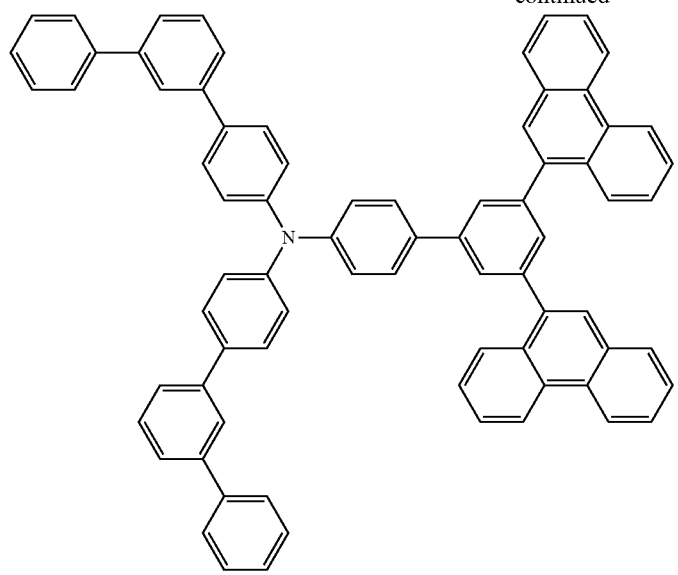
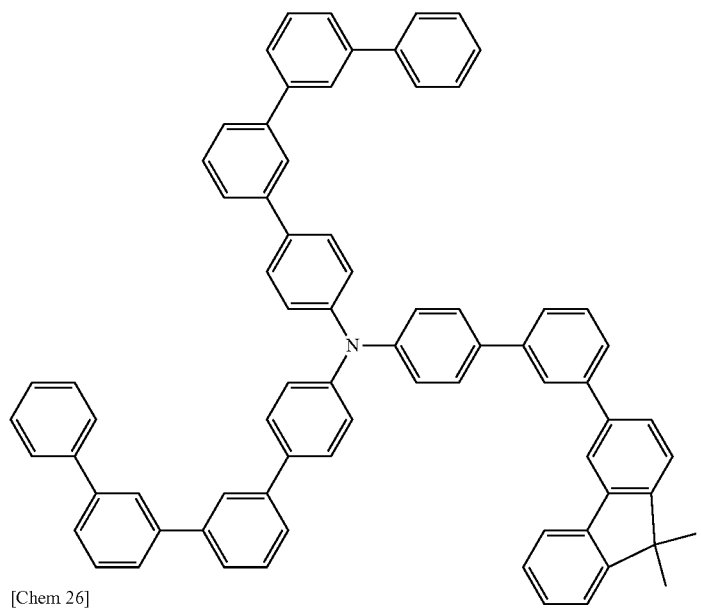
[Chem 26]
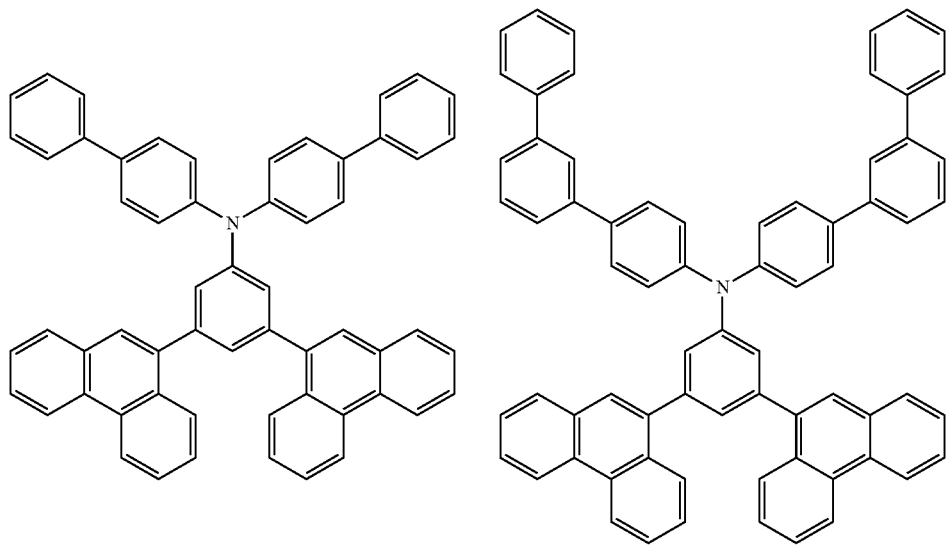

-continued
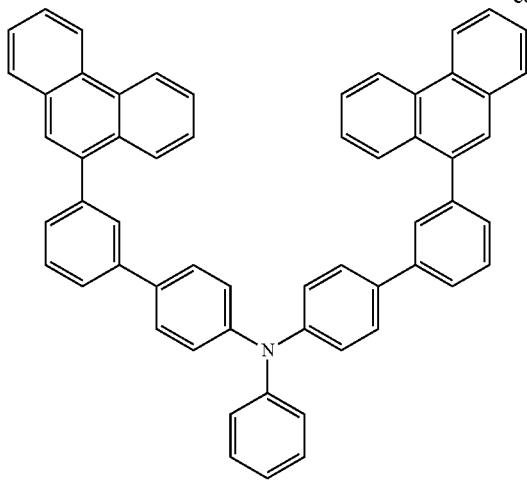
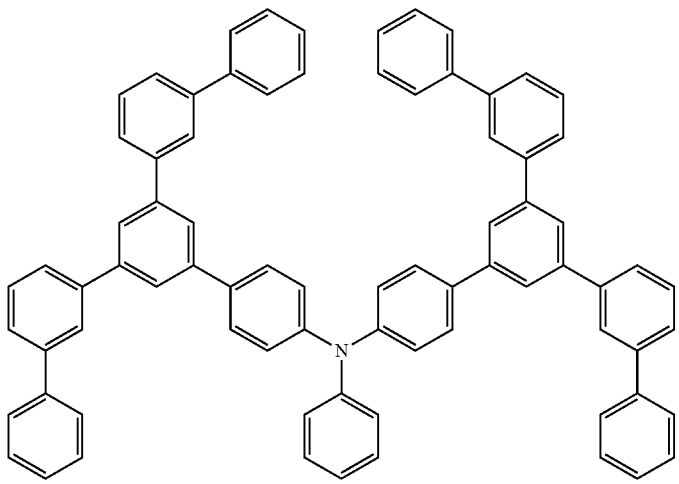
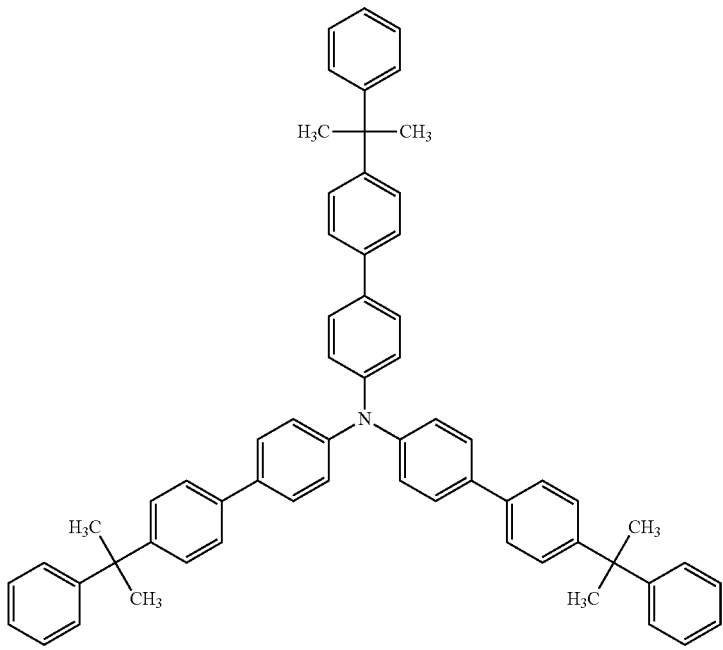

-continued

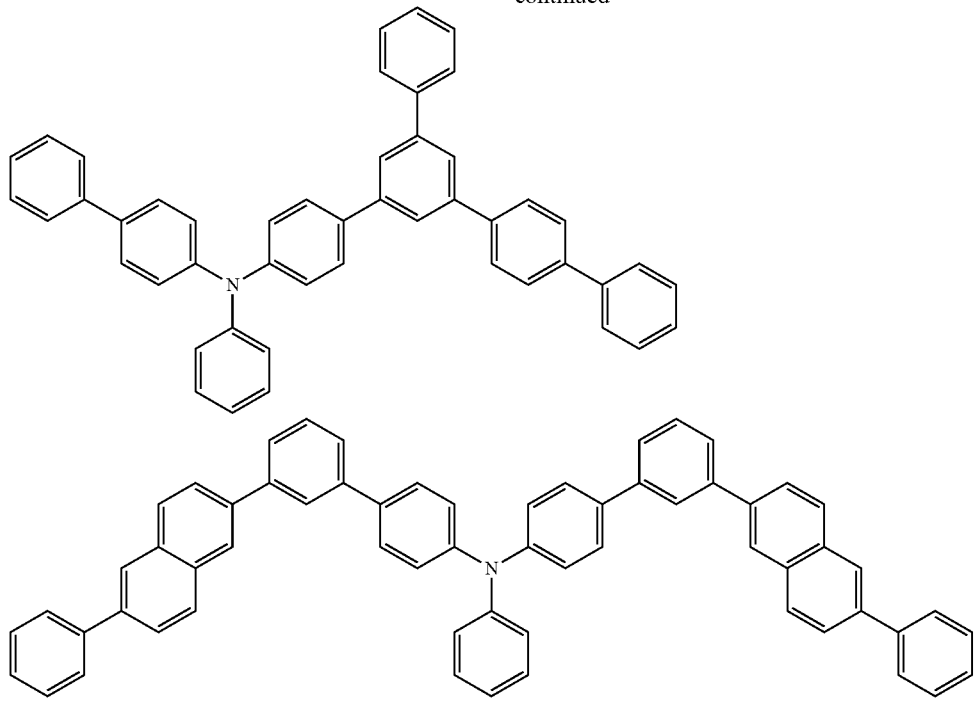

The molecular weight of the monoamine compound represented by the formula (I) is usually 400 or more, preferably 500 or more, and usually 2,500 or less, preferably 1,500 or less. When it exceeds the upper limit, there is a risk of decrease in hole transporting property and thus the case is not preferred. When it is less than the lower limit, there is a risk of decrease in heat resistance and thus the case is not preferred.

Moreover, a glass transition temperature of the monoamine compound represented by the formula (I) is 60° C. or higher and is preferably 90° C. or higher. When it is less than the lower limit, there is a risk of decrease in heat resistance and thus the case is not preferred.

In this connection, among the compounds represented by the formula (I), the compounds represented by the following formula (II) and the following formula (III) are novel compounds. Since the compounds represented by the following formula (II) and the following formula (III) are excellent in electric durability, they are useful as an electron transporting material and especially are preferably used for an organic electroluminescent device.

<Formula II>

[Chem 27]

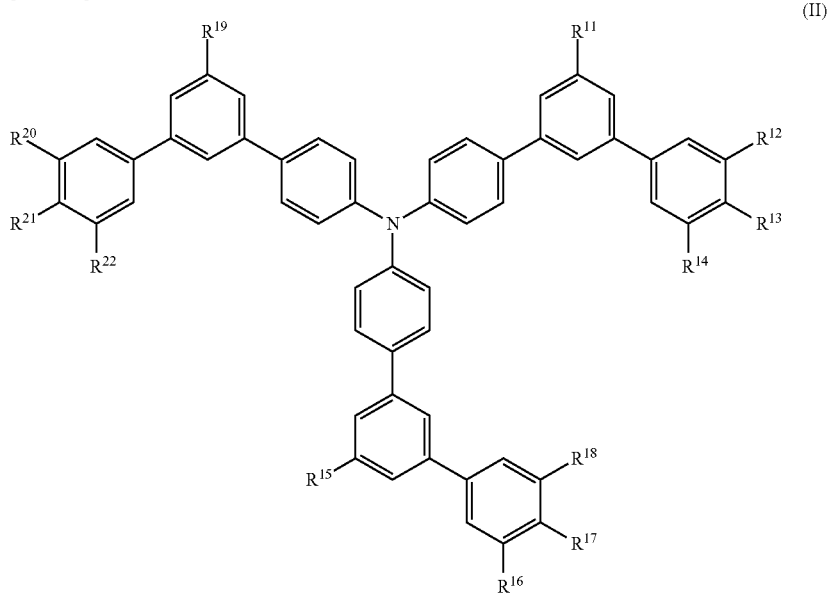

(II)

wherein $R^{11}$ to $R^{22}$ represent a hydrogen atom, an aryl group, or an alkyl group; $R^{11}$ to $R^{22}$ may be the same or different from each other; provided that any one of $R^{11}$ to $R^{22}$ is an aryl group or an alkyl group; $R^{11}$ to $R^{22}$ may further have an aryl group or an alkyl group as a substituent in the case where $R^{11}$ to $R^{22}$ are an aryl group or an alkyl group; and $R^{11}$ to $R^{22}$ may be combined with an adjacent substituent to form a ring.

$R^{11}$ to $R^{22}$ represent a hydrogen atom, an aryl group, or an alkyl group. As the aryl group, aryl groups exemplified as the above $R^1$ to $R^9$ may be mentioned and preferable ones are also the same. Moreover, as the alkyl group, alkyl groups exemplified as the above $R^1$ to $R^9$ may be mentioned and preferable ones are also the same.

Furthermore, in the case where $R^{11}$ to $R^{22}$ have an aryl group or an alkyl group as a substituent, the aryl group and the alkyl group are the same as the aryl group and the alkyl group exemplified as the substituent of $R^1$ to $R^9$.

As the ring formed by combining any of $R^{11}$ to $R^{22}$ with an adjacent substituent, a benzene ring, a naphthalene ring, a triphenylene ring, a phenanthrene ring, a pyrene ring, and the like may be mentioned.

Preferable molecular weight and glass transition temperature of the compound represented by the formula (II) are the same as those described in the case of the formula (I).

Among the compounds represented by the formula (II), the compound represented by the following formula (II-1) is preferred.

[Chem 28]

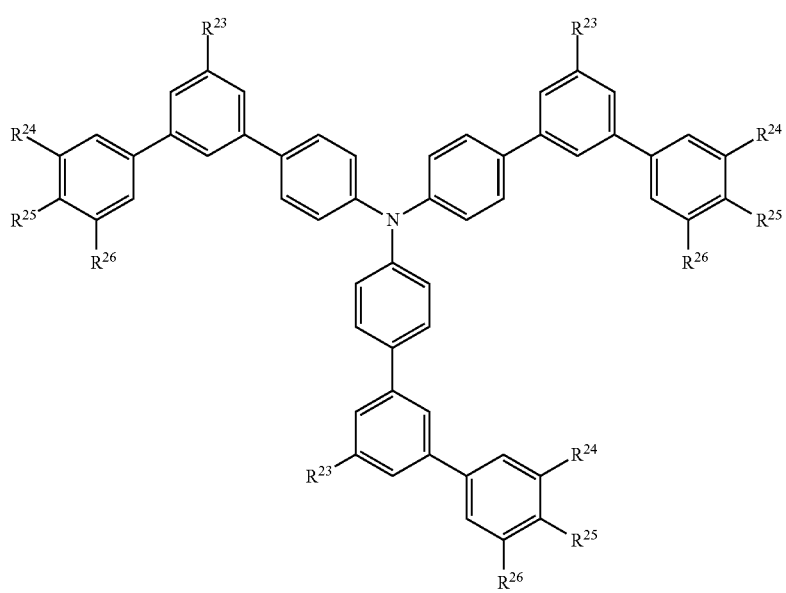

(II-1)

wherein $R^{23}$ to $R^{26}$ represent a hydrogen atom, an aryl group, or an alkyl group; $R^{23}$ to $R^{26}$ may be the same or different from each other; provided that any one of $R^{23}$ to $R^{26}$ is an aryl group or an alkyl group; $R^{23}$ to $R^{26}$ may further have an aryl group or an alkyl group as a substituent in the case where $R^{23}$ to $R^{26}$ are an aryl group or an alkyl group; and $R^{23}$ to $R^{26}$ may be combined with an adjacent substituent to form a ring.

$R^{23}$ to $R^{26}$ have the same meanings as the above $R^{11}$ to $R^{22}$ have. The substituents of $R^{23}$ to $R^{26}$ have the same as the substituents of the above $R^{11}$ to $R^{22}$.

<Formula III>

[Chem 29]

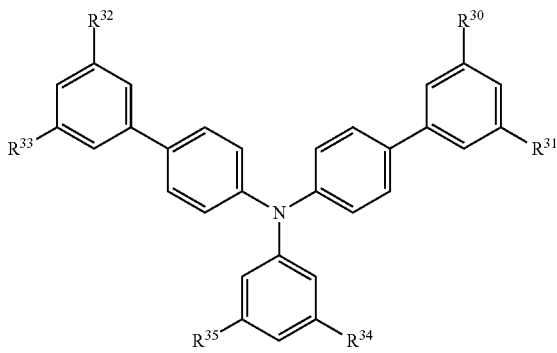

(III)

wherein $R^{30}$ to $R^{35}$ represent a hydrogen atom, an aryl group, or an alkyl group; $R^{30}$ to $R^{35}$ may be the same or different from each other; provided that any one of $R^{30}$ to $R^{35}$ is an aryl group or an alkyl group; $R^{30}$ to $R^{35}$ may further have an aryl group or an alkyl group as a substituent in the case where $R^{30}$ to $R^{35}$ are an aryl group or an alkyl group; and $R^{30}$ to $R^{35}$ may be combined with an adjacent substituent to form a ring.

$R^{30}$ to $R^{35}$ represent a hydrogen atom, an aryl group, or an alkyl group. As the aryl group, aryl groups exemplified as the above $R^1$ to $R^9$ may be mentioned and preferable ones are also the same. Moreover, as the alkyl group, alkyl groups exemplified as the above $R^1$ to $R^9$ may be mentioned and preferable ones are also the same.

Furthermore, the aryl group and the alkyl group in the case where $R^{30}$ to $R^{35}$ have an aryl group or an alkyl group as a substituent are the same as the aryl group and the alkyl group exemplified as the substituent of $R^1$ to $R^9$.

As the ring formed by combining any of $R^{30}$ to $R^{35}$ with an adjacent substituent, those exemplified as the ring formed by combining any of $R^{11}$ to $R^{22}$ of the compound represented by the above formula (II) with an adjacent substituent may be mentioned.

Preferable molecular weight and glass transition temperature of the compound represented by the formula (III) are the same as those described in the case of the formula (I).

Among the compounds represented by the formula (III), the compound represented by the following formula (III-1) is preferred.

[Chem 30]

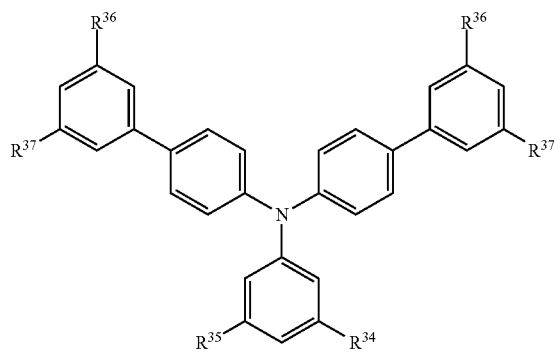

(III-1)

wherein $R^{34}$ to $R^{37}$ represent a hydrogen atom, an aryl group, or an alkyl group; $R^{34}$ to $R^{37}$ may be the same or different from each other; provided that any one of $R^{34}$ to $R^{37}$ is an aryl group or an alkyl group; $R^{34}$ to $R^{37}$ may further have an aryl group or an alkyl group as a substituent in the case where $R^{34}$ to $R^{37}$ are an aryl group or an alkyl group; and $R^{34}$ to $R^{37}$ may be combined with an adjacent substituent to form a ring.

$R^{34}$ to $R^{37}$ have the same meanings as the above $R^{30}$ to $R^{35}$ have. The substituents of $R^{34}$ to $R^{37}$ have the same meanings as the substituents of the above $R^{30}$ to $R^{35}$ have.

The following will exemplify the synthetic processes for the monoamine compounds represented by the formulae (I) to (III) in detail.

In the figures, SM-1 to 3 represent a starting material and TM-1 to 11 represent a synthetic intermediate or a final objective compound.

$Ar^a$ to $Ar^j$ represent a substituted or unsubstituted phenyl group.

$R^a$ to $R^c$ represent a hydrogen atom, an aryl group, or an alkyl group, provided that any two of $R^a$ to $R^c$ are substituted or unsubstituted phenyl groups.

$X^1$ to $X^5$ represent a group capable of substitution or conversion into a hydrogen atom, an aryl group, or an alkyl group (a hydrogen atom; a halogen atom such as a chlorine, bromine, or iodine atom; —$OSO_2R$ group (R is an arbitrary substituent) such as —$OSO_2CF_3$ group or —$OSO_2C_6H_4CH_3$ group; a substituted boron atom such as —$B(OH)_2$ group or —$B(OR)_2$ group; a halogenated metal element such as —MgX group, —ZnX group, or —SnX2 group; an alkyl carbonyl group such as an acetyl group or an ethylcarbonyl group; —CHO group; and the like).

[Chem 31]

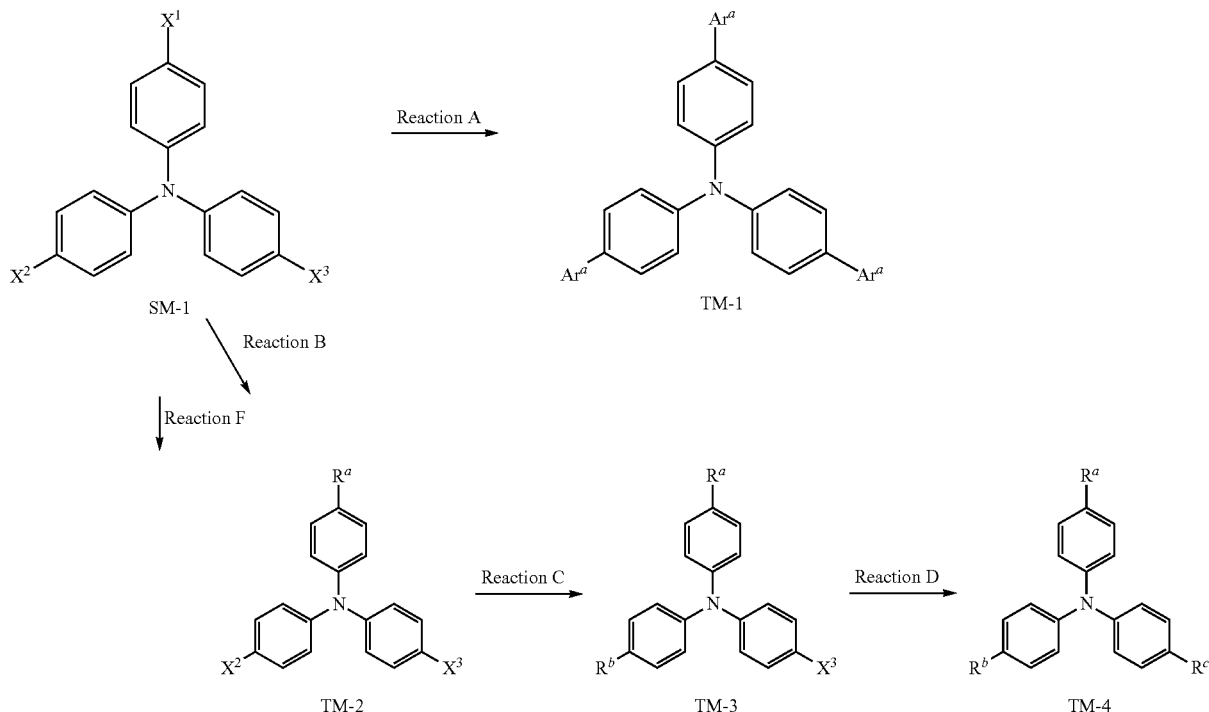

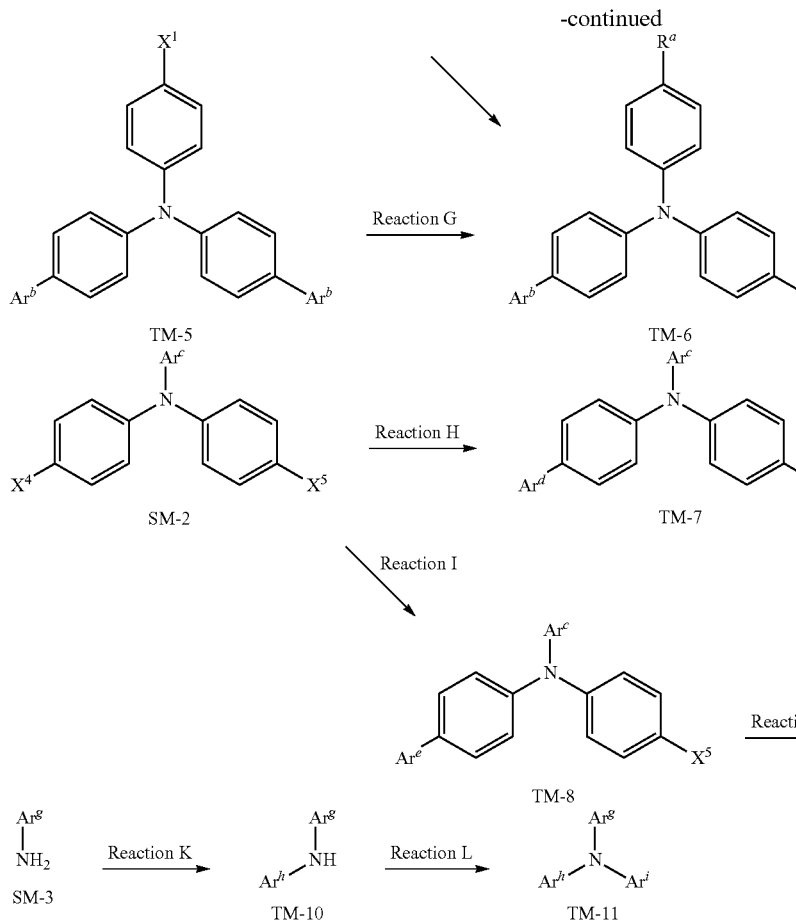

The following will describe specific reaction procedures but the procedures are not limited thereto. Reaction of combining aromatic rings each other (Reactions A to J)

There may be mentioned a process wherein an objective compound is obtained by stirring an aryl halide with an arylboronic acid, an arylboronic acid ester, an aryltin chloride, an arylzinc chloride, an arylmagnesium bromide, an arylmagnesium iodide, or the like (1.0 to 3.0 equivalents with respect to X), a zerovalent palladium catalyst such as tetrakis(triphenylphosphine)palladium (0.0001 to 0.2 equivalent with respect to X), a base such as sodium tert-butoxide, potassium tert-butoxide, cesium carbonate, sodium carbonate, potassium carbonate, tripotassium phosphate, triethylamine, potassium hydroxide, or sodium hydroxide (2 to 10 equivalents with respect to X), and a solvent such as water, methanol, ethanol, n-hexanol, ethylene glycol, ethylene glycol monoethyl ether, diethyl ether, dimethoxyethane, tetrahydrofuran, 1,4-dioxane, benzene, toluene, xylene, chlorobenzene, dichlorobenzene, dichloromethane, N,N-dimethylformamide, cyclohexane, cyclohexanone, ethyl benzoate, or ethyl acetate (about 0.01 to 100 L/mol with respect to X) under an inert gas atmosphere under a temperature condition of −40 to 150° C. for about 1 to 60 hours.

In addition, synthesis using a known coupling reaction is possible. As the known coupling methods, specifically, a coupling reaction of rings each other, such as a coupling reaction of an aryl halide with an aryl borate, can be used, which are described or cited in "Palladium in Heterocyclic Chemistry: A guide for the Synthetic Chemist" (second edition, 2002, Jie Jack Li and Gordon W. Gribble, Pergamon), "Sen-1-kinzoku ga Hiraku Yuki Gosei, Sono Tasaina Hannou Keishiki to Saishin no Seika" (1997, Jiro Tsuji, Kagaku Dojin), "Vollhardt Shore Gendai Yuki Kagaku, the second volume" (2004, K. P. C. Vollhardt, Kagaku Dojin), and the like.

Reaction of Introducing Alkyl Group into Aromatic Ring (Reactions B to D, G)

A known reaction is applicable. For example, there may be mentioned a method of reacting an aryl halide with an alkylboronic acid or an alkylmagnesium halide under an inert gas atmosphere and the like (see Tetrahedron (1998), 54, 12707-14 and the like).

Moreover, there may be mentioned a method of introducing an alkylcarbonyl group by reacting an arylene with an alkanoyl chloride under an inert gas atmosphere in the presence of a Lewis acid catalyst such as an aluminum chloride and then reducing it using a hydrazine, palladium-carbon, or the like.

In addition, an alkylating agent such as a dialkyl sulfate can be also used.

Moreover, in the introduction of a quaternary alkyl group, there may be mentioned a method of reacting an arylene with an alkyl halide in the presence of a Lewis acid such as an aluminum chloride.

Reaction of Introducing Eliminating Group Capable of Substitution into Hydrogen Atom, Aryl Group, or Alkyl Group A known halogenation method, substituted sulfonylation method, substituted boration method, or the like is arbitrarily applicable. As an examples of the halogenation methods, there may be mentioned a method of halogenation by mixing aniline in the presence of excess amount of chlorine, bromine, iodine, N-bromosuccinimide, N-chlorosuccinimide, or the like, in a solvent such as dichloromethane, N,N-dimethylformamide, chlorobenzene, toluene, or diethyl ether, under an inert gas atmosphere under a temperature condition of −20 to +80° C. for about 1 to 24 hours.

Reactions of Introducing Substituted or Unsubstituted Amino Group into Aromatic Ring (Reactions K, L)

It can be obtained by a method of mixing a primary amine or a secondary amine and an aryl halide (Ar—X, preferably X=Br, I) in an amount of 2 to 100 equivalents with respect to the primary amine or secondary amine in the presence of a copper catalyst such as a copper powder, a copper wire, a copper halide (CuX (X=Cl, Br, I)), or a copper oxide (CuO) (about 0.1 to 5 equivalents with respect to X), and a basic substance such as triethylamine, triethanolamine, potassium carbonate, calcium carbonate, potassium phosphate, cesium carbonate, or sodium tert-butoxide (about 1 to 100 equivalents with respect to halogen atom) under an inert gas stream without any solvent or in an aromatic solvent such as nitrobenzene or an alcoholic solvent such as tetraglyme or polyethylene glycol (usually, 0.1 to 100 L relative to 1 mol of the primary amine or secondary amine) in the temperature range of 20 to 300° C. for 1 to 60 hours;

or a method of stirring in the presence of a catalyst such as a zerovalent palladium complex such as a combination of a bivalent palladium catalyst such as $Pd_2(dba)_3$ (Pd=Palladium, dba=divenzylideneacetone), $Pd(dba)_2$, or palladium acetate, and a ligand such as BINAP (=2,2'-bis(diphenylphosphino-1,1'-binaphthyl), tri(tert-butyl)phosphine, triphenylphosphine, 1,2-bis(diphenylphosphino)ethane, 1,3-bis(diphenylphosphino)propane, 1,3-bis(diphenylphosphino)butane, or dppf (=1,1'-bis(diphenylphosphino)ferrocene), or a palladium chloride complex such as $PdCl_2(dppf)_2$ (about 0.001 to 1 equivalent with respect to X), and a basic substance such as potassium tert-butoxide, sodium tert-butoxide, potassium carbonate, cesium carbonate, or triethylamine (usually, 2 to 100 equivalents with respect to X), in a solvent such as tetrahydrofuran, dioxane, dimethoxyethane, N,N-dimethylformamide, dimethyl sulfoxide, xylene, toluene, triethylamine, or pyridine (usually, 0.1 to 100 L relative to 1 mol of the primary amine or secondary amine) at 0 to 200° C. for 1 to 60 hours;

or a method of stirring a primary amine or a secondary amine and an arylboronic acid or an arylboronic acid ester in an amount of 2 to 100 equivalents with respect to the primary amine or secondary amine together with a monovalent copper catalyst such as CuCl, CuBr, or CuI (usually, 0.001 to 5 equivalents with respect to objective compound 2) (if necessary, a ligand such as N,N'-dimethylethylene-1,2-diamine, 1,2-cyclohexanediamine, phenanthroline, salicylaldoxime (about 0.01 to 100 equivalents with respect to halogen atom) or a basic substance such as triethylamine, triethanolamine, potassium carbonate, calcium carbonate, potassium phosphate, cesium carbonate, or sodium tert-butoxide (about 1 to 100 equivalents with respect to halogen atom)) in the presence of oxygen in a solvent such as methanol, ethanol, n-butanol, ethylene glycol, ethylene glycol monoethyl ether (usually, 0.1 to 100 L relative to 1 mol of objective compound 2) in the temperature range of −10 to 200° C. for 1 to 60 hours.

In addition, for introduction of an amino group into an aromatic ring, methods described in J. Am. Chem. Soc. (2001), 123, 7727-9, Angew. Chem. Int. Ed. (2003), 42, 5400-49, Coordination Chemistry Reviews (2004), 248, 2337-64, and "Jikken Kagaku Koza 20 fourth edition" (edited by Chemical Society of Japan, Maruzen), Article of Chapter 6 (Amines) are applicable.

As purification methods for the compounds, methods described in "Bunri Seisei Gijutsu Handbook" (1993, edited by Chemical Society of Japan), "Kagaku Henkan Hou niyoru Biryou Seibun oyobi Nan-seisei Bussitsu no Koudo Bunri" (1988, published by K.K. IPC), and "Jikken Kagaku Koza 20 (fourth edition) 1" (1990, edited by Chemical Society of Japan), Article of "Bunri to Seisei" as well as a known technology can be utilized.

Specifically, there may be mentioned extraction (including suspension washing, boiling washing, ultrasonic washing, acid-base washing), adsorption, occlusion, melting, crystallization (including recrystallization from solvent, reprecipitation), distillation (distillation under normal pressure, distillation under reduced pressure), evaporation, sublimation (sublimation under normal pressure, sublimation under reduced pressure), ion-exchange, dialysis, filtration, ultrafiltration, reverse osmosis, pressure osmosis, band dissolution, electrophoresis, centrifugation, floatation, precipitation separation, magnetic separation, various kinds of chromatography (form classification: column, paper, thin-layer, capillary; mobile phase classification: gas, liquid, micelle, supercritical fluid; separation mechanism: adsorption, partition, ion-exchange, molecular sieve, chelate, gel filtration, exclusion, affinity), and the like.

As methods for identifying a product and analyzing purity, a gas chromatograph (GC), a high performance liquid chromatograph (HPLC), a high-speed amino acid analyzer (AAA), a capillary electrophoretic measurement (CE), a size-exclusion chromatograph (SEC), a gel permeation chromatograph (GPC), a cross-fractionation chromatograph (CFC), a mass spectroscopy (MS, LC/MS, GC/MS, MS/MS), a nuclear magnetic resonance apparatus (NMR ($^1$HNMR, $^{13}$CNMR)), a Fourier transform infrared spectrophotometer (FT-IR), a ultraviolet visible near-infrared spectrophotometer (UV.VIS,NIR), an electron spin resonance apparatus (ESR), a transmission electron microscope (TEM-EDX), an electron probe microanalyzer (EPMA), a metal element analysis (an ion chromatograph, an inductively-coupled plasma-emission spectrometry (ICP-AES), an atomic absorption spectrometry (AAS), a fluorescent X-ray analysis apparatus (XRF)), a non-metal element analysis, a trace analysis (ICP-MS, GF-AAS, GD-MS), and the like are applicable according to needs.

3. Organic Electroluminescent Device

The organic electroluminescent device of the invention relates to an organic electroluminescent device comprising on a substrate a cathode, an anode, and a hole transport layer and an organic light-emitting layer provided between these both electrodes.

Hereinafter, one example of structures of the organic electroluminescent device of the invention is described with reference to the drawings but the structures of the organic electroluminescent device of the invention is not limited to those shown in the following drawings.

FIG. 1 to FIG. 5 are a cross-sectional view schematically showing an example of the structure of an organic electroluminescent device of the invention, and 1 represents a substrate, 2 represents an anode, 3 represents a hole injection layer (anode buffer layer), 4 represents a hole transport layer, 5 represents a light-emitting layer, 6 represents a hole blocking layer, 7 represents an electron transport layer, and 8 represents a cathode. In the invention, the organic light-emitting layer may be referred to as a light-emitting layer.

(Substrate)

The substrate 1 functions as a support in the organic electroluminescent device, and a plate of quartz or glass, a metal plate, a metal foil, a plastic film, a sheet, or the like is used. In particular, a glass plate and a plate or film of a transparent synthetic resin such as polyester, polymethacrylate, polycarbonate or polysulfone are preferred. In the case of using the synthetic resin substrate, care must be taken with respect to gas barrier property. In case where the gas barrier property of the substrate is too small, the organic electroluminescent device might be deteriorated due to the air outside having passed through the substrate, thus the case not being preferred. Therefore, it is one preferred method to provide a dense silicon oxide film on at least one side of the synthetic resin substrate to thereby ensure sufficient gas barrier property.

(Cathode)

An anode 2 is provided on the substrate 1. The anode 2 functions to inject a hole into a hole transport layer 4. The anode 2 is usually constituted by a metal such as aluminum, gold, silver, nickel, palladium or platinum, a metal oxide such as indium oxide and/or tin oxide, a metal halide such as copper iodide, carbon black, or a conductive polymer such as poly(3-methylthiophene), polypyrrole or polyaniline. The anode 2 is usually formed by a sputtering method or a vacuum deposition method. In the case of forming the anode 2 from a fine particle of a metal such as silver, a fine particle of copper iodide, a carbon black, a fine particle of a conductive metal oxide or a fine particle of a conductive polymer, it can also be formed by dispersing in a suitable binder resin solution and coating the dispersion on the substrate 1. Further, in the case of forming the anode 2 from the conductive polymer, it is also possible to directly form a polymerized thin film on the substrate 1 through electrolytic polymerization, or form the anode 2 by coating a conductive polymer on the substrate 1 (App. Phys. Lett., vol. 60, p. 2711, 1992).

The anode 2 is usually of a single-layer structure but, as needed, it may be of a laminated structure formed of a plurality of materials.

The thickness of the anode 2 varies depending upon required transparency. In the case of transparency being required, the transmittance for visible light is desirably adjusted to be usually 60% or more, preferably 80% or more. In this case, the thickness of the anode is usually 5 nm or more, preferably 10 nm or more, and is usually 1,000 nm or less, preferably 500 nm or less. In the case where the anode may be opaque, the thickness of the anode 2 is arbitrary, and may be formed by a metal, as needed, so as to also function as the substrate 1.

(Hole Transport Layer)

Usually, a hole transport layer 4 is provided on the anode 2. The material for use in the hole transport layer is the monoamine compound represented by the above formula (1). The monoamine compound preferably has a glass transition temperature of 90° C. or higher in view of heat resistance.

The hole transport layer 4 can be formed by a wet coating method such as a common coating method (e.g., a spray coating method, a printing method, a spin coating method, a dip coating method or a die coating method) or a various printing methods (e.g., an ink jet method or a screen printing method), or a dry coating method such as a vacuum deposition method.

In the case of the coating method, only one or, two or more kinds of the hole transporting materials or, as needed, a binder resin or an additive such as a coating property-improving agent which does not function as a trap of a hole are dissolved in a proper solvent to prepare a coating solution, and the solution is coated on the anode 2 according to the spin coating method or the like, followed by drying to form the hole transport layer 4. Examples of the binder resin include polycarbonate, polyarylate, polyester, and the like. When the binder is in a large amount, it would reduce the hole mobility, and hence the amount is preferably small, with 50% by weight or less being usually preferred as a content in the hole transport layer.

In the case of vacuum deposition method, the hole transporting material is placed in a crucible installed within a vacuum chamber and, after evacuating the vacuum chamber by means of a proper vacuum pump to about $10^{-4}$ Pa, the crucible is heated to evaporate the hole transporting material and form the hole transport layer 4 on the substrate 1 on which the anode 2 has been formed and which is placed facing the crucible.

The thickness of the hole transport layer 4 is usually 5 nm or more, preferably 10 nm or more, and is usually 300 nm or less, preferably 100 nm or less. In order to uniformly form such a thin film, the vacuum deposition method is generally often employed.

(Light-Emitting Layer)

Usually, a light-emitting layer 5 is provided on the hole transport layer 4. In the invention, the organic light-emitting layer contains an organic compound having a pyridine ring, a pyrazine ring, or a triazine ring is contained as the aforementioned partial structure.

The light-emitting layer 5 is usually formed by a light-emitting material which can emit a strong light when excited in a space between energized electrodes by recombination of a hole injected from the anode 2 and having migrated through the hole transport layer 4 and an electron injected from the cathode and having migrated. Usually, a light-emitting material and a host material are contained in the light-emitting layer 5. The organic compound having a pyridine ring, a pyrazine ring, or a triazine ring as a partial structure is preferably used as the host material.

In the invention, an organometallic complex is preferably mentioned as a light-emitting material for use in the light-emitting layer. Particularly, an organometallic complex containing a metal selected from Groups 7 to 11 of the periodic table is mentioned.

Preferred examples of the metal in the phosphorescent organometallic complex containing a metal selected from Groups 7 to 11 of the periodic table include ruthenium, rhodium, palladium, silver, rhenium, osmium, iridium, platinum and gold. As these organometallic complexes, there are preferably mentioned compounds exemplified below.

As these organometallic complexes, there are preferably mentioned compounds represented by the following formula (9) or (10):

$$ML_{(q-j)}L'_j \qquad (9)$$

wherein M represents a metal, q represents a number of valence of the metal, L and L' represent a bidentate ligand, and j represents 0, 1 or 2 in the formula (9);

[Chem 32]

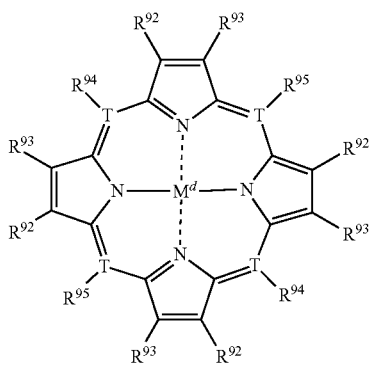

(10)

wherein $M^d$ represents a metal, T represents carbon or nitrogen, $R^{92}$ to $R^{95}$ each independently represents a substituent and, when T represents nitrogen, $R^{94}$ and $R^{95}$ are absent in the formula (10).

Hereinafter, the compound represented by the formula (9) is first explained.

In the formula (9), M represents an arbitrary metal and specific preferable examples include metals described above as the metals selected from Groups 7 to group 11 of the periodic table.

Moreover, the bidentate ligands L and L' in the formula (9) each represents a ligand having the following partial structure:

[Chem 33]

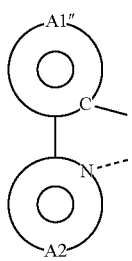

L

[Chem 34]

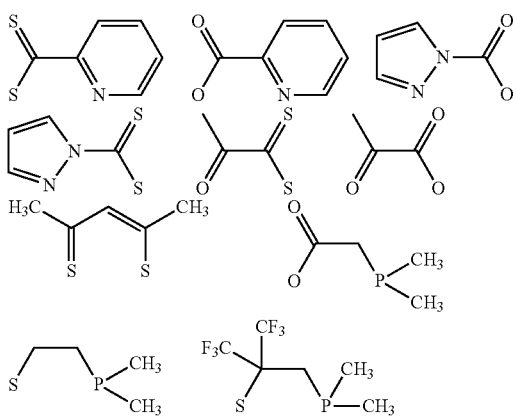

L'

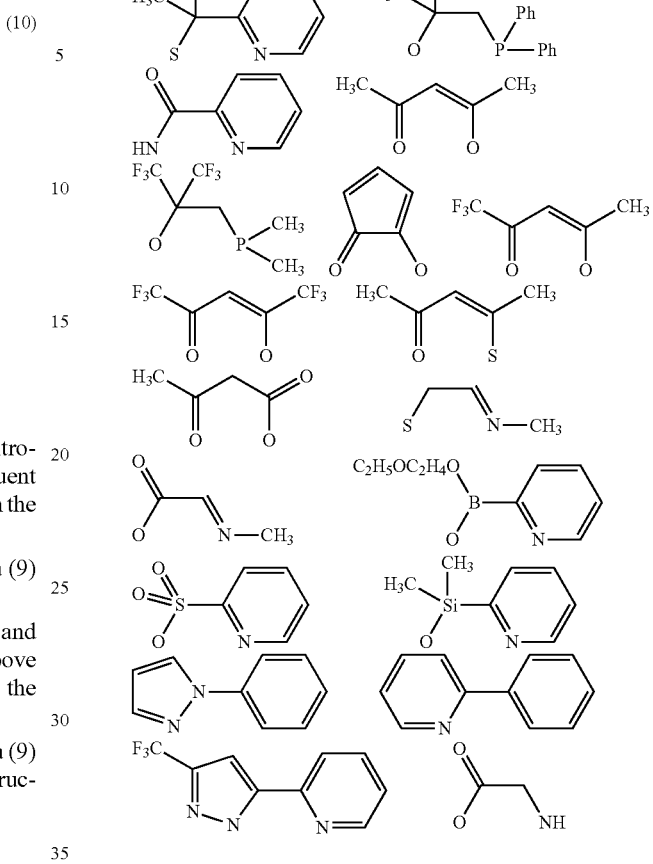

As L', from the viewpoint of the stability of the complex, particularly preferred are the following:

[Chem 35]

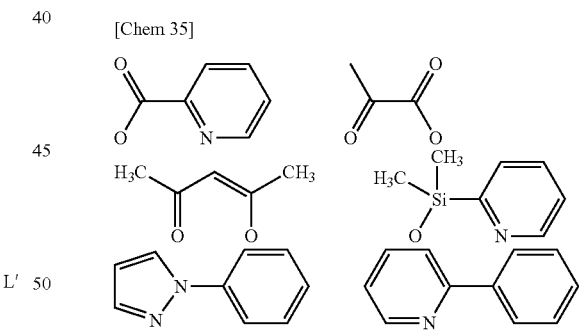

In the above partial structures of L and L', the ring A1" represents an aromatic hydrocarbon group or an aromatic heterocycle group, which optionally has a substituent. Moreover, the ring A2 represents a nitrogen-containing aromatic heterocycle group, which optionally has a substituent. Preferable substituent includes a halogen atom such as a fluorine atom; an alkyl group such as a methyl group or an ethyl group; an alkenyl group such as a vinyl group; an alkoxycarbonyl group such as a methoxycarbonyl group or an ethoxycarbonyl group; an alkoxy group such as a methoxy group or an ethoxy group; an aryloxy group such as a phenoxy group or a benzyloxy group; a dialkylamino group such as a dimethylamino group or a diethylamino group; a diarylamino group such as a diphenylamino group; a carbazolyl group; an acyl group such as an acetyl group; a haloalkyl group such as a trifluoromethyl group; a cyano group; an aromatic hydrocarbon group such as a phenyl group, a naphthyl group, or a phenanthryl group; and the like.

As more preferred compounds represented by the formula (9), there are mentioned compounds represented by the following formulae (9a), (9b) and (9c):

[Chem 36]

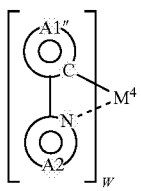

(9a)

wherein $M^4$ represents a metal the same as M, w represents a valence of the above metal, ring A1" represents an aromatic hydrocarbon group which optionally has a substituent, and ring A2 represents a nitrogen-containing aromatic heterocycle group which optionally has a substituent in the formula (9a);

[Chem 37]

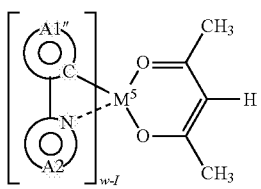

(9b)

wherein $M^5$ represents a metal the same as M, w represents a valence of the above metal, ring A1" represents an aromatic hydrocarbon group or an aromatic heterocycle group, which optionally has a substituent, and ring A2 represents a nitrogen-containing aromatic heterocycle group which optionally has a substituent in the formula (9b);

[Chem 38]

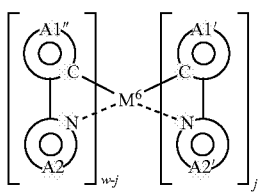

(9c)

wherein $M^6$ represents a metal the same as M, w represents a valence of the metal, j represents 0, 1 or 2, ring A1" and ring A1' each independently represents an aromatic hydrocarbon group or an aromatic heterocycle group, which optionally has a substituent, and ring A2 and ring A2' each independently represents a nitrogen-containing aromatic heterocycle group which optionally has a substituent in the formula (9b).

Preferred examples of the ring A1" and ring A1' in the above formulae (9a), (9b) and (9c) include a phenyl group, a biphenyl group, a naphthyl group, an anthryl group, a thienyl group, a furyl group, a benzothienyl group, a benzofuryl group, a pyridyl group, a quinolyl group, an isoquinolyl group and a carbazolyl group.

Preferred examples of ring A2 and ring A2' include a pyridyl group, a pyrimidyl group, a pyrazyl group, a triazyl group, a benzothiazole group, a benzoxazole group, a benzimidazole group, a quinolyl group, an isoquinolyl group, a quinoxalyl group and a phenanthridyl group.

Furthermore, examples of the substituent, which the compounds represented by the formulae (9a), (9b) and (9c) optionally have, include a halogen atom such as a fluorine atom; an alkyl group such as a methyl group or an ethyl group; an alkenyl group such as a vinyl group; an alkoxycarbonyl group such as a methoxycarbonyl group or an ethoxycarbonyl group; an alkoxy group such as a methoxy group or an ethoxy group; an aryloxy group such as a phenoxy group or a benzyloxy group; a dialkylamino group such as a dimethylamino group or a diethylamino group; a diarylamino group such as a diphenylamino group; a carbazolyl group; an acyl group such as an acetyl group; a haloalkyl group such as a trifluoromethyl group; a cyano group; and the like.

Moreover, in the case where the substituent is an alkyl group, the carbon number is usually 1 or more and 6 or less. Furthermore, in the case where the substituent is an alkenyl group, the carbon number is usually 2 or more and 6 or less. Moreover, in the case where the substituent is an alkoxycarbonyl group, the carbon number is usually 2 or more and 6 or less. Furthermore, in the case where the substituent is an alkoxy group, the carbon number is usually 1 or more and 6 or less. Moreover, in the case where the substituent is an aryloxy group, the carbon number is usually 6 or more and 14 or less. Furthermore, in the case where the substituent is a dialkylamino group, the carbon number is usually 2 or more and 24 or less. Moreover, in the case where the substituent is a diarylamino group, the carbon number is usually 12 or more and 28 or less. Furthermore, in the case where the substituent is an acyl group, the carbon number is usually 1 or more and 14 or less. Moreover, in the case where the substituent is a haloalkyl group, the carbon number is usually 1 or more and 12 or less.

In this connection, these substituents may be connected to each other to form a ring. As a specific example, the substituent which ring A1" has and the substituent which ring A2 has may be connected to each other to form one condensed ring, or the substituent which ring A1' has and the substituent which ring A2' has may be connected to each other to form one condensed ring. An example of such condensed ring is a 7,8-benzoquinoline group or the like.

Of these, more preferred examples of the substituent in ring A1", ring A1', ring A2 and ring A2' include an alkyl group, an alkoxy group, an aromatic hydrocarbon group, a cyano group, a halogen atom, a haloalkyl group, a diarylamino group and a carbazolyl group.

Moreover, preferred examples of $M^4$ and $M^5$ in the formulae (9a), (9b) and (9c) include ruthenium, rhodium, palladium, silver, rhenium, osmium, iridium, platinum and gold.

Specific examples of the organometallic complexes represented by the above formulae (9), (9a), (9b) and (9c) are shown below. However, the complexes are not limited to the following compounds.

[Chem 39]
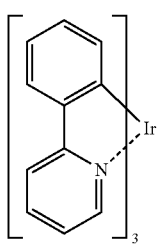 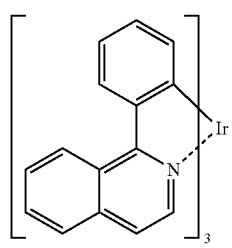
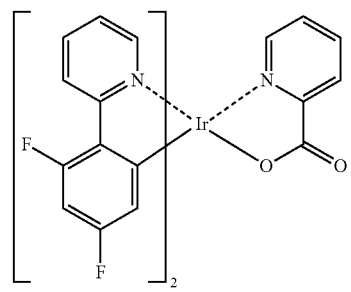
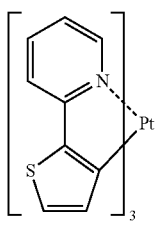 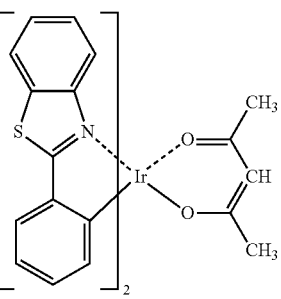
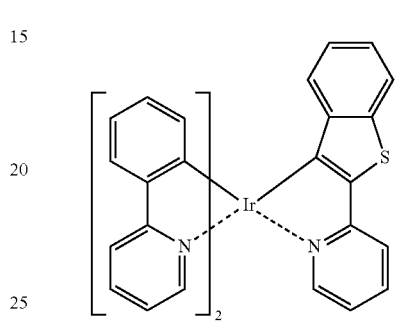
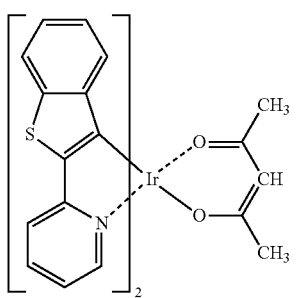
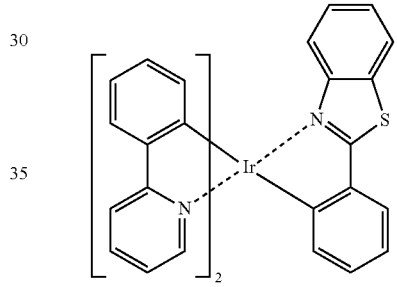
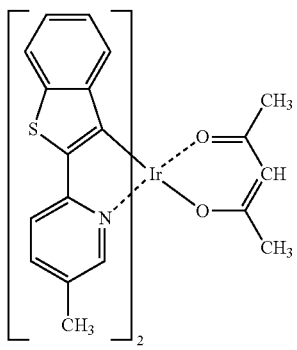
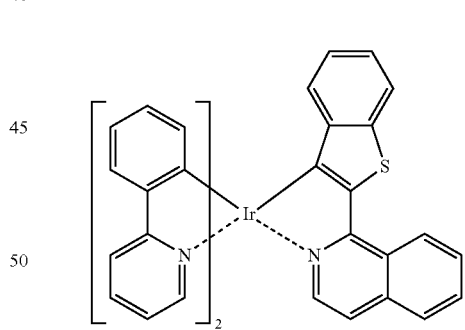
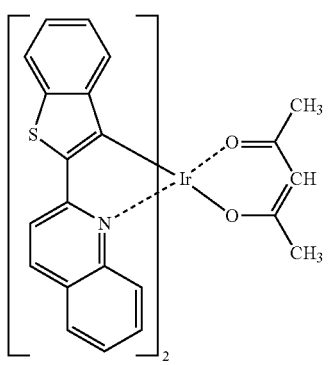
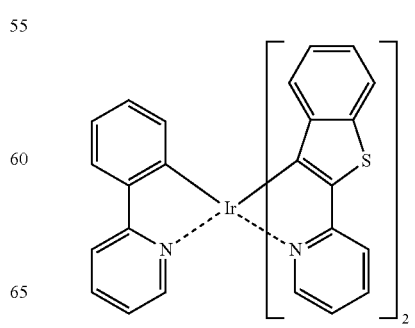

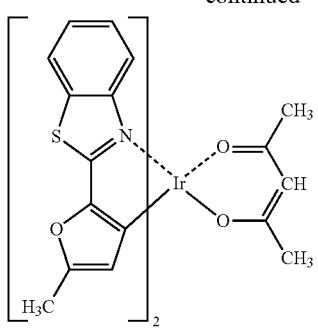
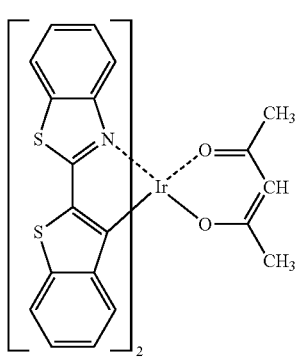
[Chem 40]
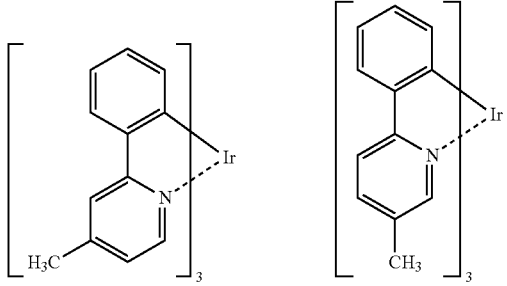
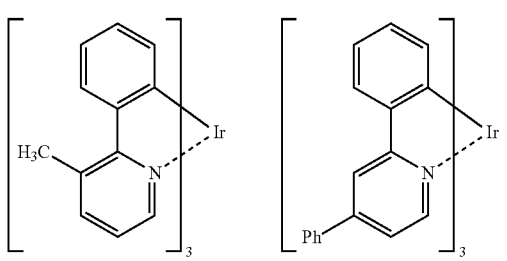
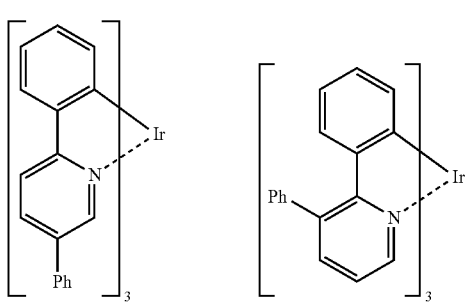
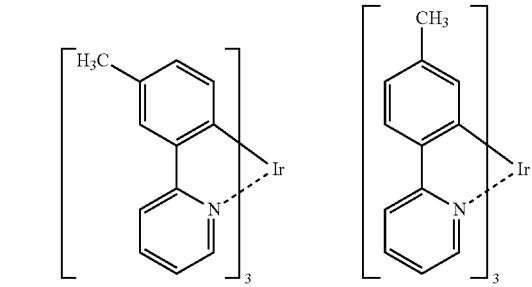
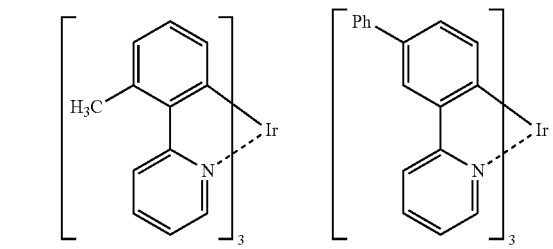
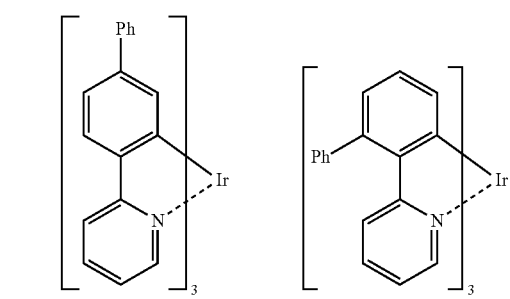
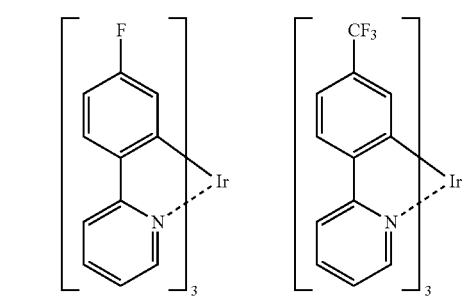
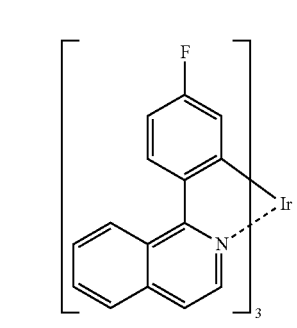
Furthermore, of the organometallic complexes represented by the above formulae (9), (9a), (9b) and (9c), particularly, as ligand L and/or L', those compounds are preferred which have a 2-arylpyridine-based ligand, i.e., 2-arylpyridine, this having an arbitrary substituent bonded thereto, and this having an arbitrary group condensed thereto.

The following will describe the compound represented by the formula (10).

In the formula (10), $M^d$ represents a metal, and specific examples include metals described above as the metals selected from Groups 7 to 11 of the periodic table. Of these, preferable examples include ruthenium, rhodium, palladium, silver, rhenium, osmium, iridium, platinum and gold, and divalent metals such as platinum and palladium are particularly preferred.

Moreover, in the formula (10), $R^{92}$ and $R^{93}$ each independently represents a hydrogen atom, a halogen atom, an alkyl group, an aralkyl group, an alkenyl group, a cyano group, an amino group, an acyl group, an alkoxycarbonyl group, a carboxyl group, an alkoxy group, an alkylamino group, an aralkylamino group, a haloalkyl group, a hydroxyl group, an aryloxy group, an aromatic hydrocarbon group or aromatic heterocycle group.

Furthermore, when T represents carbon, $R^{94}$ and $R^{95}$ each independently represents the substituents represented by the exemplified compounds the same as $R^{92}$ and $R^{93}$. Moreover, when T represents nitrogen, $R^{94}$ and $R^{95}$ are absent.

Moreover, $R^{92}$ to $R^{95}$ may further have a substituent. Furthermore, the substituent which is optionally had is not limited and an arbitrary group can be used as the substituent.

Additionally, $R^{92}$ to $R^{95}$ may be connected to each other to form a ring.

Specific examples of the organometallic complex represented by the formula (10) (T-1, T-10 to T-15) are shown below. However, a dopant is not limited to the following exemplified compounds. Moreover, Me represents a methyl group and Et represents an ethyl group.

[Chem 41]

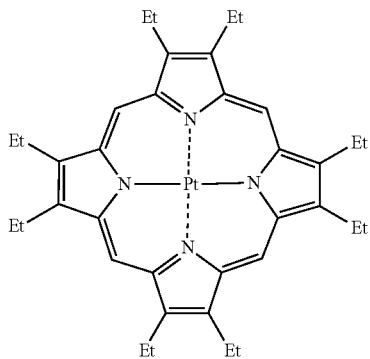
(T-1)

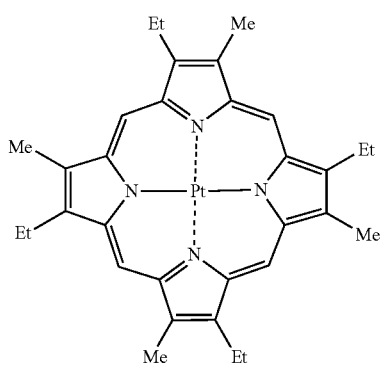
(T-10)

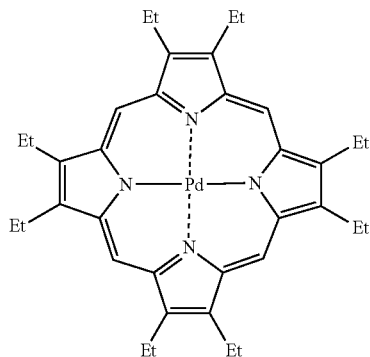
(T-11)

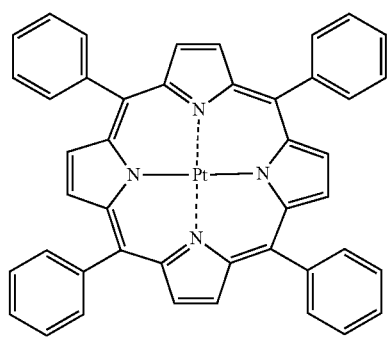
(T-12)

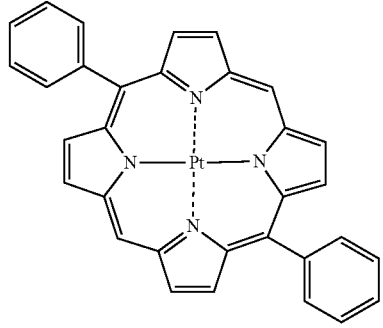
(T-13)

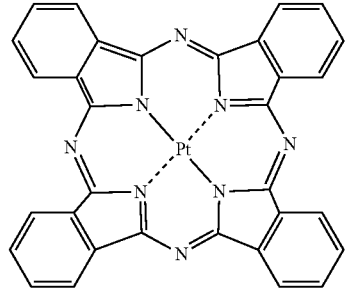
(T-14)

(T-15)

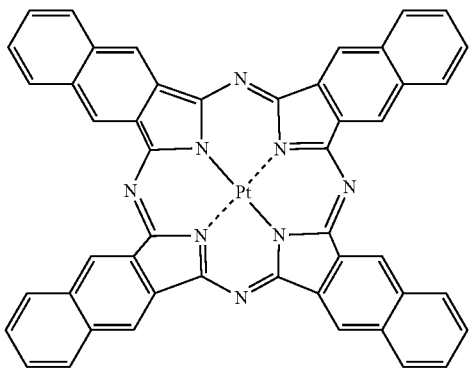

The thickness of the light-emitting layer 5 is usually 3 nm or more, preferably 5 nm or more, and is usually 200 nm or less, preferably 100 nm or less.

The light-emitting layer 5 can be also formed in the same manner as the case of the hole transport layer 4.
(Cathode)

The cathode 8 functions to inject an electron into the light-emitting layer 5. As the material to be used as the cathode 8, those materials which are used for the anode 2 may be employed but, in order to inject an electron with a high efficiency, a metal having a low work function is preferred. Thus, suitable metals such as tin, magnesium, indium, calcium, cesium, aluminum and silver, or the alloys thereof, are used. Specific examples thereof include an electrode of alloys having a low work function, such as magnesium-silver alloy, magnesium-indium alloy and aluminum-lithium alloy.

The thickness of the cathode 8 is usually the same as the thickness of the anode 2.

For the purpose of protecting the cathode 8 comprising the metal having a low work function, to further laminate thereon a metal layer which has a high work function and is stable in the atmosphere serves to enhance stability of the device. For this purpose, metals such as aluminum, silver, copper, nickel, chromium, gold and platinum are used.

Furthermore, it is also an effective technique for improving efficiency of the device to insert an extremely thin insulating film (0.1 to 5 nm), such as LiF, $MgF_2$ or $Li_2O$, into the interface between the cathode 8 and the light-emitting layer 5 or the electron transport layer 7 to be described below (Appl. Phys. Lett., vol. 70, p. 152, 1997; JP-A-10-74586; and IEEE Trans. Electron. Devices, vol. 44, p. 1245, 1997).
(Electron Transport Layer)

Figure 2:
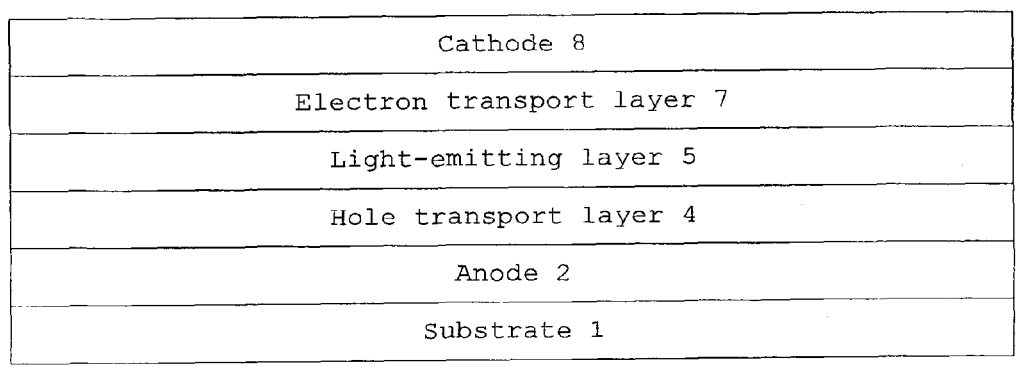
FIG. 2 is a schematic cross-sectional view showing one example of the organic electroluminescent device of the invention.

For the purpose of further improving light emission efficiency of the device, an electron transport layer 7 may be preferably provided between the light-emitting layer 5 and the cathode 8 as shown in FIG. 2. The electron transport layer 7 is formed from a compound which can transport, with a good efficiency, an electron injected from the cathode 8 toward the light-emitting layer 5 between the energized electrodes.

Examples of the material satisfying such requirements include metal complexes such as aluminum complex of 8-hydroxyquinoline (JP-A-59-194393); a metal complex of 10-hydroxybenzo[h]quinoline; an oxadiazole derivative; a distyrylbiphenyl derivative; a silole derivative; a metal complex of 3- or 5-hydroxyflavone; a metal complex of benzoxazole; a metal complex of benzothiazole; trisbenzimidazolylbenzene (U.S. Pat. No. 5,645,948), a quinoxaline compound (JP-A-6-207169); a phenanthroline derivative (JP-A-5-331459); 2-t-butyl-9,10-N,N'-dicyanoanthraquinonediimine; an n-type hydrogenated amorphous silicon carbide; an n-type zinc sulfide; an n-type zinc selenide; and the like.

It is preferred to dope the electron transporting material described above with an alkali metal (described in JP-A-10-270171, JP-A-2002-100482, JP-A-2002-100478, and the like) since it serves to improve the electron transporting property.

The thickness of the electron transport layer 6 is usually 5 nm or more, preferably 10 nm or more and is usually 200 nm or less, preferably 100 nm or less.

The electron transport layer 7 is formed on the light-emitting layer 5 by the coating method or the vacuum deposition method to laminate in the same manner as with the hole transport layer 4. Usually, the vacuum deposition method is employed.
(Hole Blocking Layer)

Figure 3:
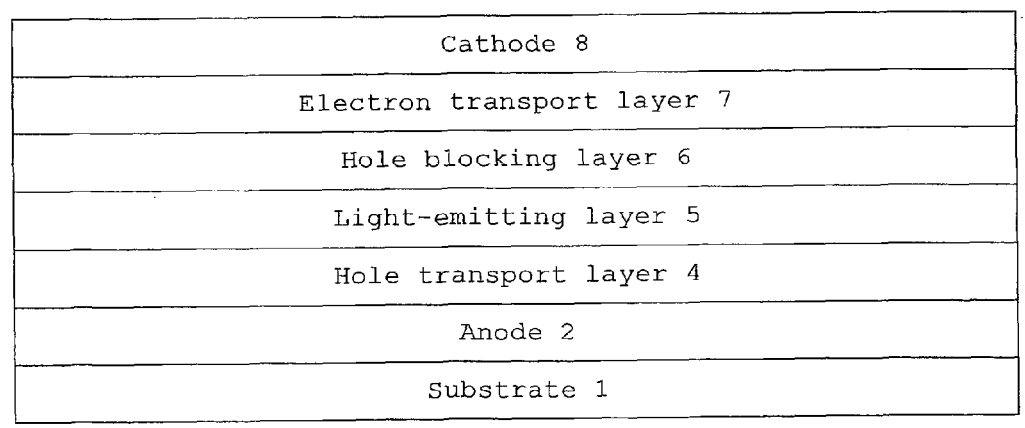
FIG. 3 is a schematic cross-sectional view showing one example of the organic electroluminescent device of the invention.

In the device shown in FIG. 3, a hole blocking layer 6 is laminated on the light-emitting layer 5 in contact with the interface between the light-emitting layer 5 and the electron transport layer 7.

The hole blocking layer 6 is preferably formed by a compound which can prevent a hole migrating from the hole transport layer 4 from passing through the light-emitting layer and which can effectively transport an electron injected from the cathode 8 toward the light-emitting layer 5. Therefore, physical properties required for a material constituting the hole blocking layer 6 include a high electron mobility and a low hole mobility. The hole blocking layer 6 has the function of confining a hole and an electron within the light-emitting layer 5 to thereby improve light emission efficiency.

As the hole blocking material satisfying such requirement, a known material can be employed.
(Hole Injection Layer)

Figure 4:
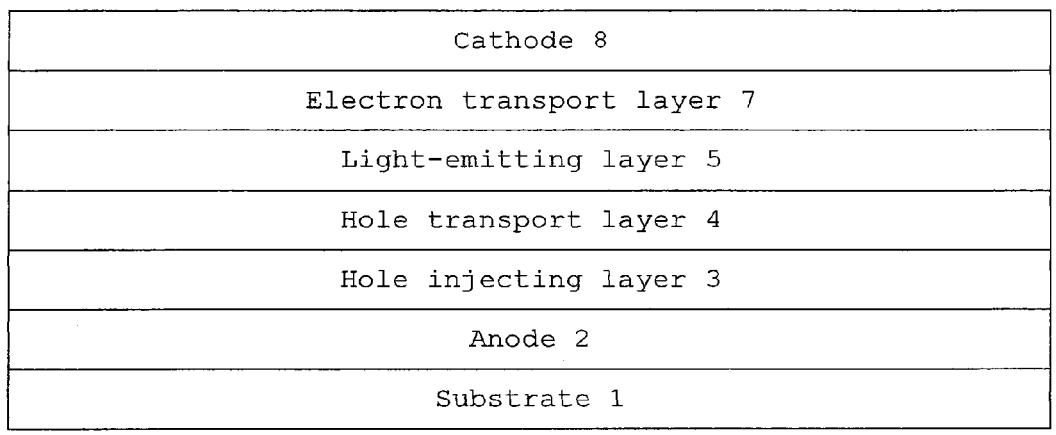
FIG. 4 is a schematic cross-sectional view showing one example of the organic electroluminescent device of the invention.

For the purpose of more improving efficiency of injecting a hole and improving adhesion of the whole organic layers onto the anode 2, it is also conducted to insert a hole injection layer 3 between the hole transport layer 4 and the anode 2 as shown in FIG. 4. Insertion of the hole injection layer 3 serves to provide the effect of reducing the initial driving voltage of the device and, at the same time, depressing an increase in voltage upon continuously driving the device at a constant current.

As to requirements for a material to be used in the hole injection layer 3, the material is required to have a good contact with the anode 2, form a uniform thin film, and be thermally stable, that is, it has a high melting point and a high glass transition temperature, with the melting point being preferably 300° C. or more, and the glass transition temperature being 100° C. or more. Further, the material is required to have an enough low ionization potential to easily facilitate injection of a hole from the anode 2 and have a large hole mobility.

For this purpose, there have been reported, as the material for the hole injection layer 3, an organic compound such as a porphyrin derivative or a phthalocyanine compound (JP-A-63-295695), a hydrazone compound, an alkoxy-substituted aromatic diamine derivative, p-(9-anthryl)-N,N'-di-p-tolylaniline, polythienylenevinylene, poly-p-phenylenevinylene, polyaniline (Appl. Phys. Lett., vol. 64, p. 1245, 1994), polythiophene (Optical Materials, vol. 9, p. 125, 1998) and starburst type aromatic triamine (JP-A-4-308688); a sputtered carbon film (Synth. Met., vol. 91, p. 73, 1997); and metal oxides such as a vanadium oxide, a ruthenium oxide and a molybdenum oxide (J. Phys. D, vol. 29, p. 2750, 1996).

As a material for the above hole injection layer 3, either of a low-molecular compound and a high-molecular compound may be used.

In the case of the hole injection layer 3, too, the thin film can be formed similarly with the hole transport layer 4 and, in the case of using an inorganic material, a sputtering method, an electron beam deposition method or a plasma CVD method may further be employed.

As to the thickness of the thus-formed hole injection layer 3, the lower limit is usually 3 nm, preferably about 10 nm, and the upper limit is usually 100 nm, preferably about 50 nm in the case where the layer is formed using the low-molecular compound.

When the polymer compound is used as a material for the hole injection layer 3, for example, the aforesaid polymer compound, the electron-accepting compound and, as needed, a binder resin or an additive such as a coating property-improving agent (e.g., a leveling agent) which does not function as a trap of a hole, are added and dissolved to prepare a coating solution, and the solution is coated on the anode 2 according to a common coating method such as a spray coating method, a printing method, a spin coating method, a dip coating method or a die coating method or an ink jet method, followed by drying to form the hole injection layer 3 as a thin film. Examples of the binder resin include polycarbonate, polyarylate, polyester, and the like. When the binder resin is in a large amount in the layer, it might reduce the hole mobility, and hence the amount is desirably smaller, with 50% by weight or less in the content in the hole injection layer 3 being preferred.

It is also possible to form a thin film by previously forming a thin film on a medium such as a film, a supporting substrate or a roll according to the aforementioned thin film-forming method, and transferring the thin film on the medium onto the anode 2 through thermal transfer or pressure transfer.

The lower limit of the film thickness of the hole injection layer 3 formed as described hereinbefore using the polymer compound is usually 5 nm, preferably about 10 nm, and the upper limit is usually 1,000 nm, preferably about 500 nm.

(Layer Constitution)

As to the organic electroluminescent device of the invention, a reverse structure to that shown in FIG. 1, i.e., a structure wherein the cathode 8, the light-emitting layer 5, the hole transport layer 4 and the anode 2 are laminated in this order on the substrate 1 may also be employed. As has been already described, it is possible to provide the organic electroluminescent device of the invention between two substrates at least one of which has a high transparency. Likewise, it is possible to laminate in the reverse order to each of the layer constitution shown in any of FIG. 2 to FIG. 4. Also, in any of the layer constitution shown in FIG. 1 to FIG. 4, an arbitrary layer other than the above-described layers may be provided within the range of not departing from the spirit of the invention, or a proper variation such as a variation of providing a layer having the above functions of a plurality of the layers to thereby simplify the layer constitution is possible.

Alternatively, it is also possible to employ a top emission structure or to use a transparent electrode as both of the cathode and the anode to prepare a transparent element or, further, to employ a structure wherein a plurality of the layer constitution shown in FIG. 1 are stacked (a structure wherein a plurality of the light-emitting units are stacked). On such occasion, use of, for example, $V_2O_5$ or the like as a charge generating layer (CGL) in place of the interface layers (in the case where ITO and Al are used as the anode and the cathode, respectively, the two layers) between the layer constitutions (light-emitting units) serves to reduce barrier between the structures, and thus the case is more preferred in view of light emission efficiency and driving voltage.

The invention can be applied to any of a structure wherein the organic electroluminescent device comprises a single device, a device which comprises a structure provided in an array form, and a structure wherein the anode and the cathode are disposed in an X-Y matrix pattern.

EXAMPLES

The invention is more specifically described with reference to Examples, but the invention is not limited to the description of the following Examples unless the gist of the invention is exceeded.

Synthetic Example 1

Synthesis of Objective Compounds 1 to 3

[Chem 42]

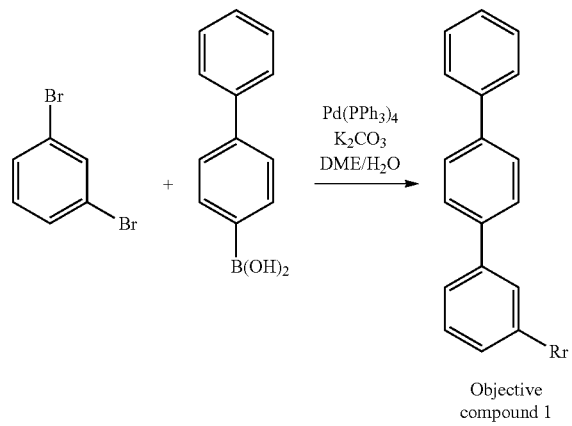

Objective compound 1

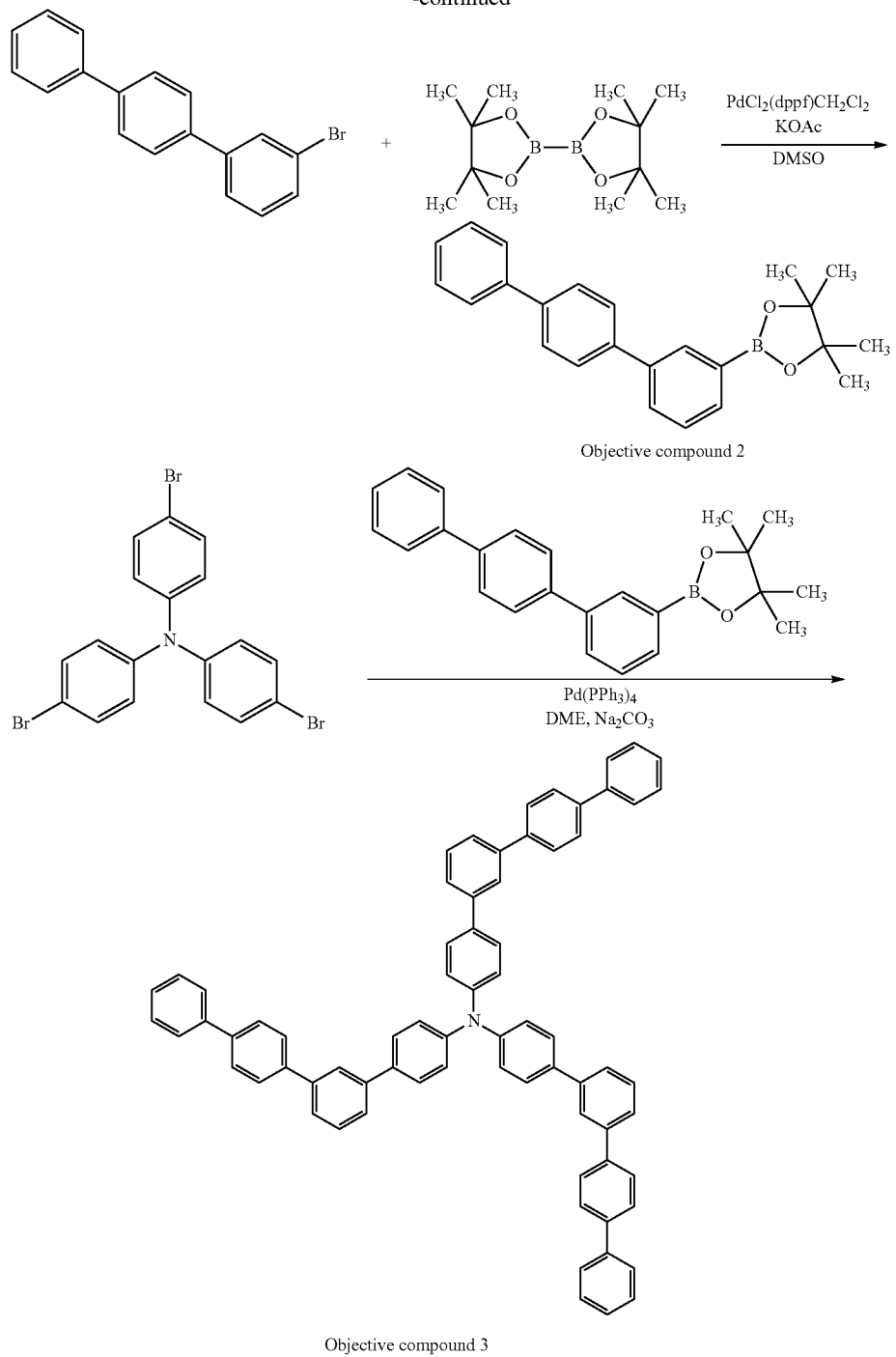

Under a nitrogen atmosphere, a mixture of 1,3-dibromobenzene (23 g), 4-biphenylboric acid (21 g), potassium carbonate (40.6 g), tetrakis(triphenylphosphine)palladium (2.0 g), dimethoxyethane (294 ml) and water (147 ml) was stirred for 6 hours while heating under reflux. The resultant reaction mixture was filtrated and subjected to sprinkling washing with ethanol and water to obtain 37 g of a crude product containing the objective compound 1. The objective compound 1 is purified by extraction with chloroform and recrystallization from the crude product.

In a nitrogen stream, the objective product 1 (7 g), bis(pinacolatodiborone) (6.90 g), potassium acetate (7.55 g) and DMSO (200 ml) were stirred under heating to 60° C. for 15 minutes and [1,1'-bis(diphenylphosphino)ferrocene]dichloropalladium(II)dichloromethane complex (0.555 g) was added thereto, followed by stirring under heating at 80° C. for 8 hours. After cooling to room temperature, water (250 ml) and toluene (500 ml) were added to the reaction solution, followed by stirring. After the aqueous layer was re-extracted with toluene, the organic layer was combined and washed with a saturated sodium chloride solution five times and then magnesium sulfate and activated clay were added thereto. The magnesium sulfate and activated clay were separated by filtration and toluene was removed under reduced pressure. The precipitated solid content was purified by silica gel column chromatography to obtain an objective compound 2 (6.6 g).

In a nitrogen stream, tetrakis(triphenylphosphine)palladium (0.718 g) and a 2M of potassium carbonate aqueous solution (60 ml) were successively added to a mixture of the objective compound (7.32 g), tris(4-bromophenyl)amine (3 g), and dimethoxyethane (120 ml), followed by stirring for 4 hours while heating under reflux. After cooling to room temperature, the separated precipitate was separated by filtration and was subjected to sprinkling washing twice with a sodium hydrogen carbonate solution and once with methanol. The residue was subjected to suspension washing once in N,N-dimethylformamide solvent and once in methanol solvent while heating under reflux and then dried to obtain 3.43 g of a crude product of the objective compound 3. In a nitrogen stream, tetrakis(triphenylphosphine)palladium (0.337 g) and a 2M of sodium carbonate aqueous solution (60 ml) were successively added to a mixture of the crude product of the objective compound 3 (3.43 g), the objective compound (2.08 g), and dimethoxyethane (120 ml), followed by stirring for 9.5 hours while heating under reflux. After cooling to room temperature, the separated precipitate was separated by filtration and was subjected to sprinkling washing with water. After activated clay was added to the obtained residue, the whole was extracted with anisole (600 ml) under heating and refluxing conditions, the extract was filtrated, and the filtrate was poured into methanol to precipitate a crystal. The resultant crystal was purified by recrystallization from anisole and sublimation purification under reduced pressure to obtain the objective compound 3 (0.614 g).

The product was identified as the objective compound 3 through DEI-MS (m/Z=929 (M+)).

This had a gasification temperature of 567° C., a melting point of 290° C., and a glass transition temperature of 127° C.

Synthetic Example 2

Synthesis of Objective Compounds 4 to 6

[Chem 43]

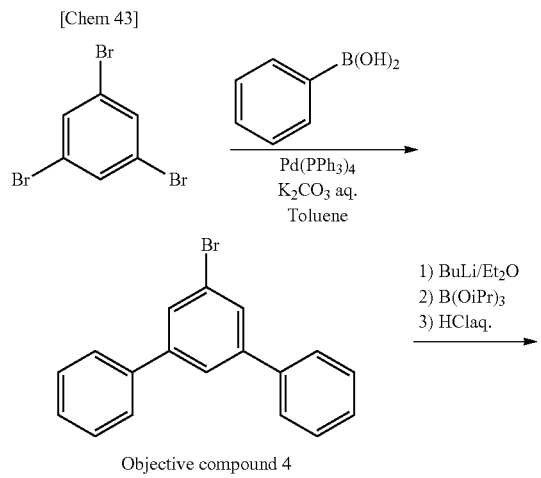

Objective compound 4

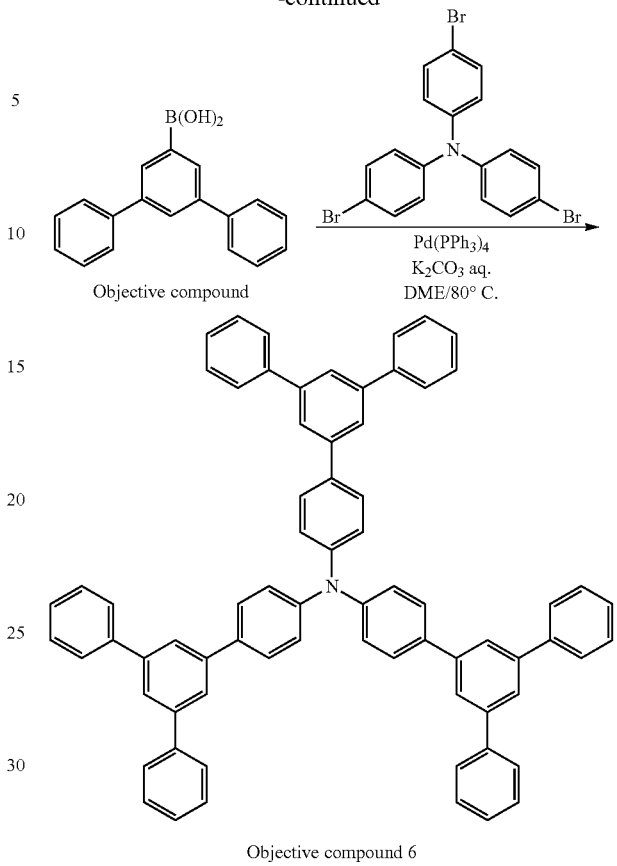

Objective compound 6

In a nitrogen stream, tetrakis(triphenylphosphine)palladium (2.773 g) and an aqueous solution of potassium carbonate (33.17 g) dissolved in water (100 g) were successively added to a mixture of 1,3,5-tribromobenzene (25.18 g), phenylboric acid (21.46 g) and toluene (310 ml), followed by stirring for 9.5 hours while heating under reflux. An organic layer was separated from the resultant solution. After the organic layer was washed with a sodium chloride solution, anhydrous magnesium sulfate and activated clay were added and, after stirring, filtration and concentration were performed. The obtained residue was purified by silica gel column chromatography to obtain an objective compound 4 (14.28 g).

In a nitrogen stream, a 1.6M of n-butyllithium in n-hexane solution was added dropwise to a mixed solution of the objective compound 4 (9.28 g), anhydrous diethyl ether (75 ml) and anhydrous toluene (50 ml) under a condition of −40 to −20° C. over a period of 10 minutes. After stirring for 1 hour as it is, the whole was cooled to −70° C., and then triisopropyl borate (20.8 ml) was dropwise added over a period of 30 minutes, followed by stirring for 40 minutes as it is. After the whole was brought back to room temperature over a period of 2 hours, 1N of hydrochloric acid aqueous solution (65 ml) was added thereto, followed by stirring for 1 hour. Toluene and a saturated sodium chloride solution were added to the resultant solution and a liquid layer was separated. After the organic layer was washed with a sodium chloride aqueous solution, it was dried with anhydrous magnesium sulfate and concentrated. Thereafter, the concentrate was purified by recrystallization from hexane-toluene to obtain an objective compound 5 (6.14 g).

In a nitrogen stream, tetrakis(triphenylphosphine)palladium (0.52 g) and 2M of potassium carbonate aqueous solution (30 g) were successively added to a mixture of tris(4-bromophenyl)amine (2.41 g), the objective compound 5 (4.94 g) and dimethoxyethane (150 ml), followed by stirring for 6.2 hours while heating under reflux. Ethanol and water were added to the resultant solution and a separated precipitate was filtrated and washed with ethanol. The resultant solid component was subjected to extraction treatment with chloroform (250 ml, twice) and the solid component obtained by concentrating the extract liquid was subjected to suspension washing in toluene while heating under reflux.

Furthermore, the solid component was subjected to suspension washing in N,N-dimethylformamide (200 ml) while heating under reflux and then sublimation purification under reduced pressure to obtain an objective compound 6 (0.83 g).

DEI-MS m/Z=929 (M$^+$)

This did not have a detectable glass transition temperature and had a melting point of 346° C. and a gasification temperature of 557° C.

Synthetic Example 3

Objective Compounds 7 to 9

[Chem 44]

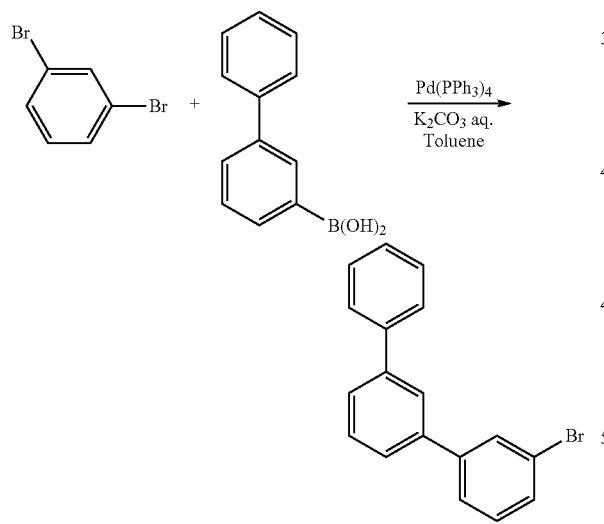

Objective compound 7

Under a nitrogen atmosphere, a mixture of 1,3-dibromobenzene (14.45 g), 3-biphenylboric acid (10 g), potassium carbonate (19.0 g), tetrakis(triphenylphosphine)palladium (0.9 g), toluene (120 ml) and water (60 ml) was stirred for 6 hours while heating under reflux. The organic layer and the aqueous layer of the resultant reaction mixture were separated and the organic layer was washed and concentrated. Thereafter, the concentrate was purified by silica gel column chromatography to obtain an objective compound 7 (8.73 g) as a transparent and colorless liquid.

[Chem 45]

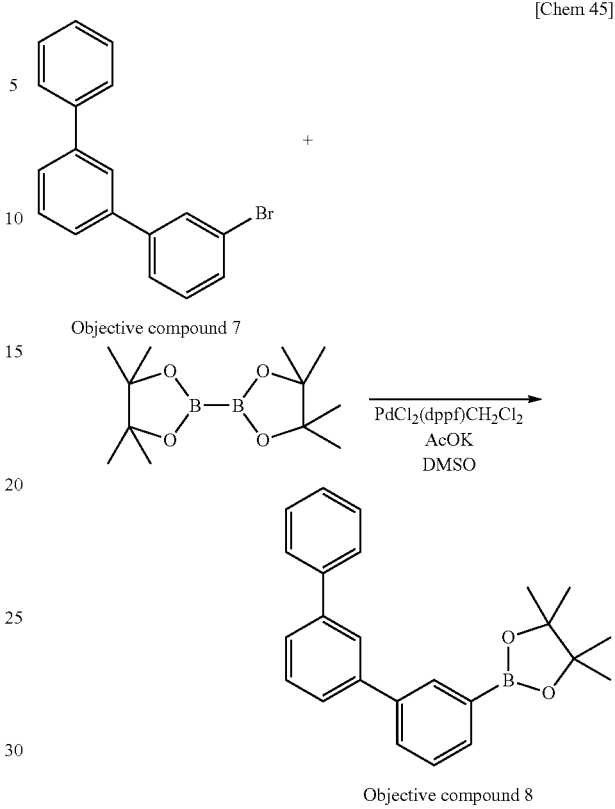

Objective compound 8

In a nitrogen stream, the objective product 7 (6.24 g), bis(pinacolatodiborone) (5.65 g), potassium acetate (6.75 g) and DMSO (140 ml) were heated to 60° C., and [1,1'-bis(diphenylphosphino)ferrocene]dichloropalladium(II)dichloromethane complex (0.49 g) was added thereto, followed by stirring under heating at 80° C. for 8 hours. After cooling to room temperature, water (100 ml) and toluene (200 ml) were added to the reaction solution, followed by stirring. After an aqueous layer was re-extracted with toluene, an organic layer was combined and washed with a saturated sodium chloride solution twice and then magnesium sulfate and activated clay were added thereto. They were separated by filtration and toluene was concentrated. To the residue in a concentrated oil state were added 5 ml of methylene chloride and 20 ml of methanol to crystallize, thereby the product was precipitated as a white crystal. The crystal was washed with methanol (100 ml) under heating to obtain an objective compound 8 (4.3 g).

[Chem 46]

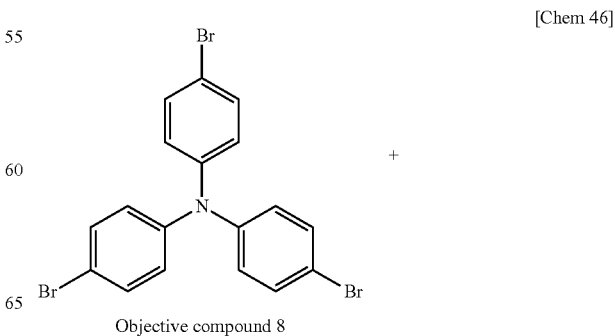

Objective compound 8

Synthetic Example 4

Objective Compounds 10 to 12

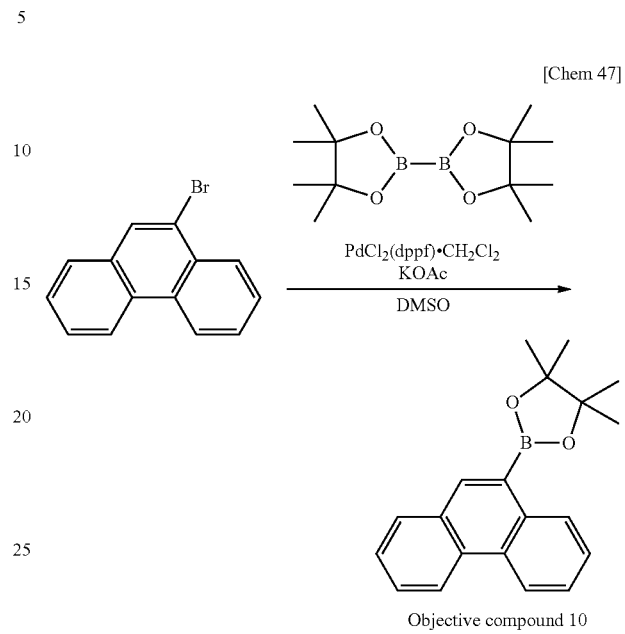

[Chem 47]

Objective compound 10

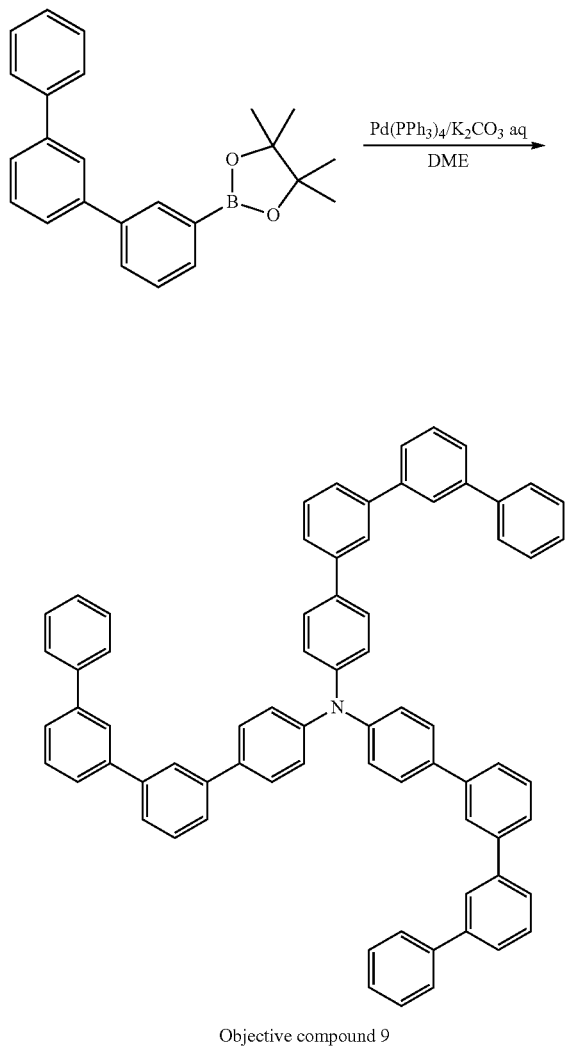

Objective compound 9

In a nitrogen stream, the objective compound 8 (4 g) obtained in the above and tris(4-bromophenyl)amine (1.35 g) were dissolved in ethylene glycol dimethyl ether (84 ml) and tetrakis(triphenylphosphine)palladium(0) (0.3 g) and a solution of potassium carbonate (3.48 g) dissolved in water (13 ml) were successively added to the system, followed by stirring under heating. After 4 hours of reaction while heating under reflux and cooling to room temperature, an organic layer was concentrated. Water and chloroform were added and the organic layer was extracted. After dried with magnesium sulfate, the whole was concentrated and further purified by column chromatography, followed by addition of methanol and suspension washing. The resultant crystal was dried and then purified by sublimation purification under reduced pressure to obtain an objective compound 9 (1 g).

The product was identified as the objective compound 9 through DEI-MS (m/Z=929 (M+)).

This had a gasification temperature of 562° C., a melting point of 225° C., and a glass transition temperature of 95° C.

In a nitrogen stream, 9-Bromophenanthrene (11.7 g), bis(pinacolatodiborone) (15.0 g), potassium acetate (17.9 g) and DMSO (200 ml) were heated to 60° C. and [1,1'-bis(diphenylphosphino)ferrocene]dichloropalladium(II) dichloromethane complex (1.32 g) was added thereto, followed by stirring under heating at 80° C. for 5.5 hours. After cooling to room temperature, water (300 ml) and toluene (200 ml) were added to the reaction solution, followed by stirring. After an aqueous layer was re-extracted with toluene (200 ml×2), an organic layer was combined and washed with a saturated sodium chloride solution twice and then magnesium sulfate and activated clay were added thereto. They were separated by filtration and toluene was removed under reduced pressure. To the residue were added 5 ml of methylene chloride and 20 ml of methanol, and a precipitated white crystal was collected by filtration to obtain an objective compound 10 (11.9 g).

[Chem 48]

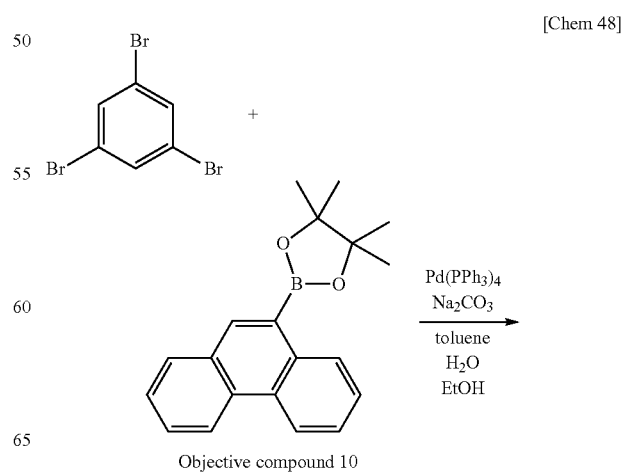

Objective compound 10

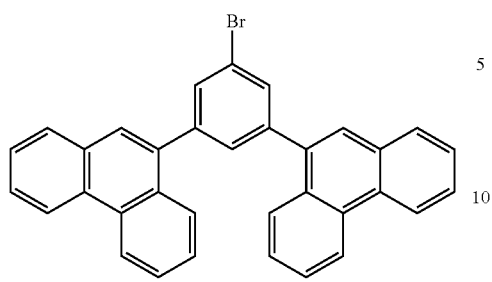

Objective compound 11

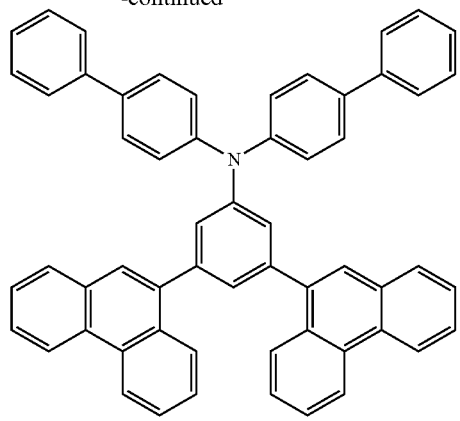

Objective compound 12

In a nitrogen stream, the objective compound 10 obtained in the above (6.00 g) and 1,3,5-tribromobenzene (2.86 g) dissolved in toluene (120 ml), an aqueous solution of sodium carbonate (4.81 g) dissolved in 50 ml of water, ethanol (10 ml), and tetrakis(triphenylphosphine)palladium(0) (0.210 g) were successively added to the system, followed by stirring for 8.5 hours while heating under reflux. After cooling to room temperature, an aqueous layer was extracted with toluene (100 ml×2), an organic layer was combined, and then magnesium sulfate and an activated clay were added thereto. They were separated by filtration and toluene was removed under reduced pressure. Then, a crystal was obtained by reprecipitation with chloroform/ethanol. Further, the crystals were purified by column chromatography and subjected to suspension washing with ethanol to obtain an objective compound 11 (1.56 g) as a white crystal.

In a nitrogen stream, to a solution of the objective compound 11 (1.50 g), bis(4-biphenyl)amine (0.945 g), tert-butoxy sodium (0.678 g) and toluene (30 ml) was added a solution prepared by stirring tris(dibenzylideneacetone)dipalladium(0)chloroform complex (0.030 g), tri-tert-butylphosphine (0.048 g), and toluene (3 ml) under a nitrogen atmosphere at 60° C. for 15 minutes, followed by stirring for 8 hours while heating under reflux. After cooling, chloroform (100 ml) activated clay and chloroform (100 ml) were added and stirred for 15 minutes. Insoluble matter was removed by filtration, the filtrate was concentrated, and reprecipitation with methylene chloride/methanol was performed to obtain a crystal. Furthermore, after purification by column chromatography, reprecipitation with methylene chloride/methanol and sublimation purification under reduced pressure were performed to obtain an objective compound 12 (1.50 g).

The product was identified as the objective compound 12 through DEI-MS (m/z=749 (M+)).

This had a gasification temperature of 523° C., no detectable melting point, and a glass transition temperature of 138° C.

[Chem 49]

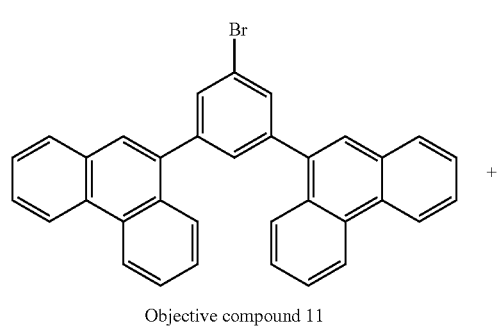

Objective compound 11

+

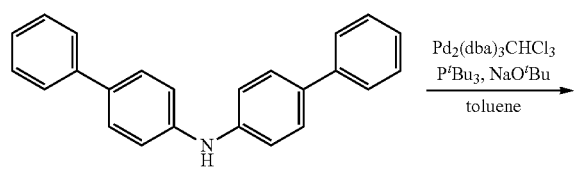

Pd$_2$(dba)$_3$CHCl$_3$
P$^t$Bu$_3$, NaO$^t$Bu
toluene

Example 1

Figure 5:
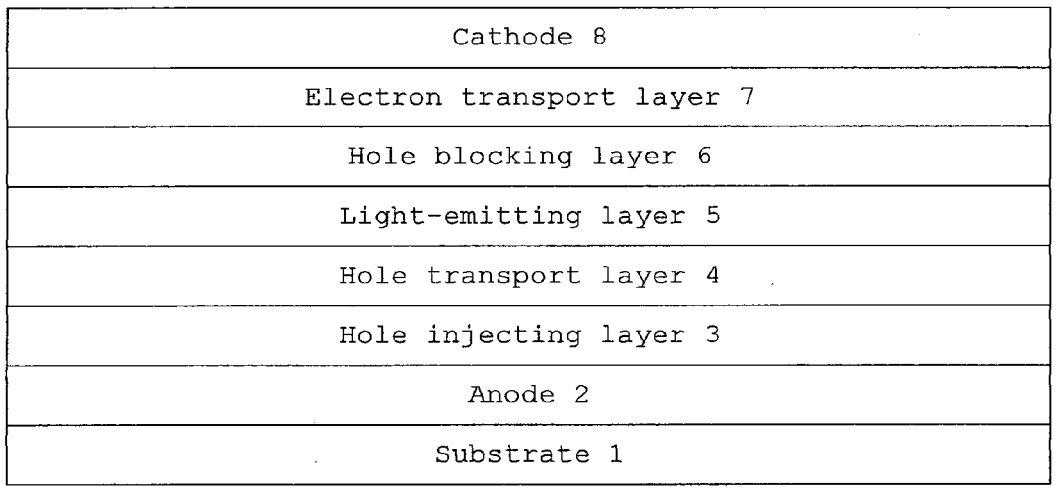
FIG. 5 is a schematic cross-sectional view showing one example of the organic electroluminescent device of the invention.

An organic electroluminescent device having a structure shown in FIG. 5 was prepared according to the following method.

An indium-tin oxide (ITO) transparent conductive film 2 accumulated in a thickness of 150 nm on a glass substrate 1 (sputtered film formation product; sheet resistance: 15Ω) was patterned in a 2-mm width stripe pattern using a common photolithography technique and a hydrochloric acid etching to form an anode. The thus patterned ITO substrate was washed by applying ultrasonic waves with acetone, washed with pure water, and then washed by applying ultrasonic waves with isopropyl alcohol in this order, followed by drying using a nitrogen blow, and finally washing by UV rays and ozone.

As a material for the hole injection layer 3, non-conjugation type polymer compound (PB-1) having an aromatic amino group of the following structural formula:

[Chem 50]

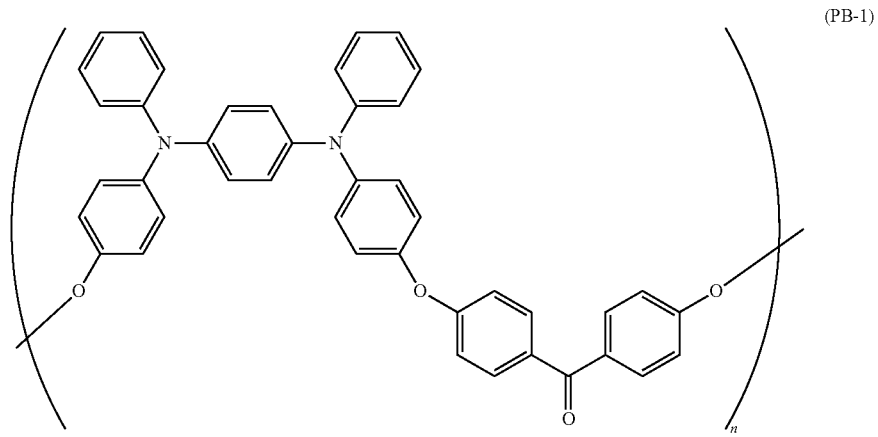

(PB-1)

weight-average molecular weight: 29,400
number-average molecular weight: 12,600
was spin-coated together with an electron acceptive compound (A-2):

[Chem 51]

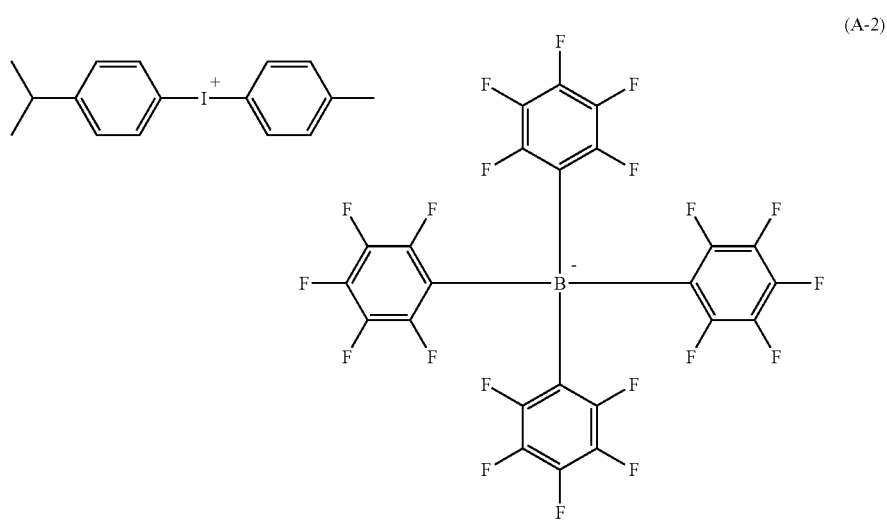

(A-2)

under the following conditions.
Spin-Coating Conditions:
Solvent: ethyl benzoate;
Concentration of coating solution: 2 [wt %];
PB-1:A-2=10:2;
Rotation number of spinner: 1,500 [rpm];
Rotation time of spinner: 30 [sec]; and
Drying conditions: 230 [° C.], 15 [min].

A uniform thin film having a film thickness of 30 nm was formed by the above-described spin coating.

Next, the substrate having formed thereon the hole injection layer was placed in a vacuum deposition apparatus. After roughly evacuating the apparatus by means of an oil rotary pump, the inside of the apparatus was evacuated till a vacuum degree became about $2.0 \times 10^{-5}$ Pa or less by employing an oil diffusion pump. A monoamine compound (arylamine compound) (H-1) shown below and placed in a ceramic crucible placed within the apparatus:

[Chem 52]

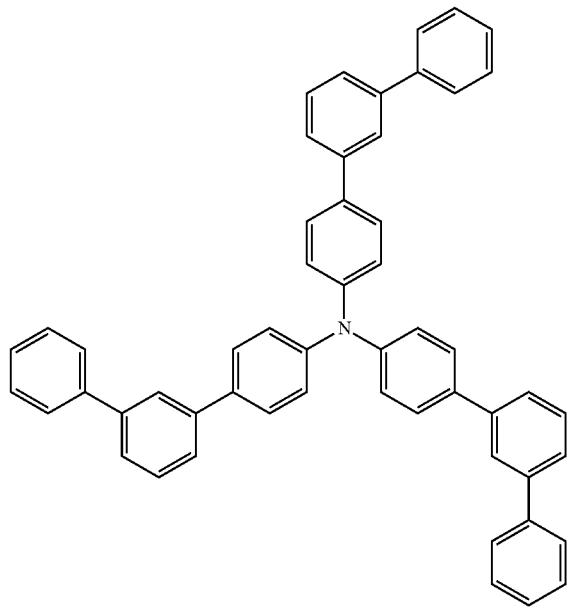
(H-1)

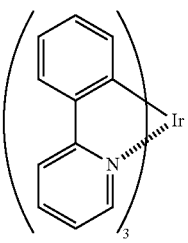
(D-1)

The crucible temperature for the compound (E-1) was controlled to be 327 to 328° C., and deposition rate was controlled to be 0.09 nm/sec, while the crucible temperature for the compound (D-1) was controlled to be 250 to 250° C. Thus, the light-emitting layer 5 having a film thickness of 30 nm and containing 6% by weight of the compound (D-1) was laminated on the hole transport layer 4. The vacuum degree during deposition was $2.7 \times 10^{-5}$ Pa.

Furthermore, as a hole blocking layer 6, the compound (HB-1) shown below:

[Chem 54]

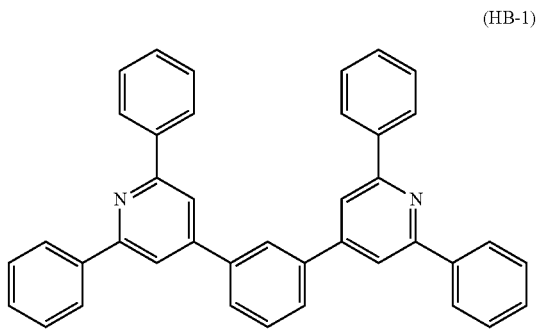
(HB-1)

was laminated in a thickness of 5 nm with controlling the temperature of the crucible to be 239 to 243° C. at the deposition rate of 0.1 nm/sec. The vacuum degree during deposition was $2.6 \times 10^{-5}$ Pa.

On the hole blocking layer 6, as an electron transport layer 7, the following aluminum 8-hydroxyquinoline complex (ET-1):

was heated through a tantalum wire heater disposed around the crucible to conduct vacuum deposition. The vacuum degree during deposition was $2.0 \times 10^{-5}$ Pa, and deposition rate was 0.12 nm/sec. Thus, there was obtained a hole transport layer 4 having a film thickness of 40 nm.

Subsequently, a compound (E-1) shown below to be used as a major component (host material) of the light-emitting layer 5 and an organic iridium complex (D-1) to be used as a sub-component (dopant) were placed in different ceramic crucibles, and a film was formed by the simultaneous binary vacuum deposition method.

[Chem 53]

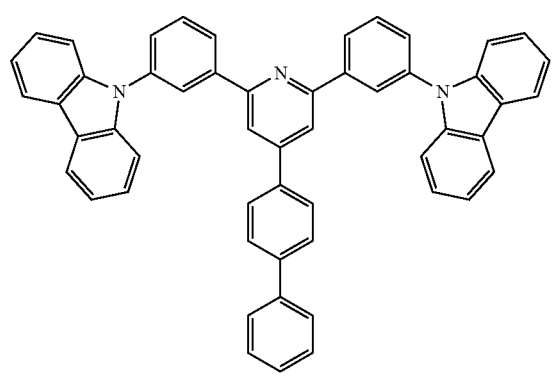
(E-1)

[Chem 55]

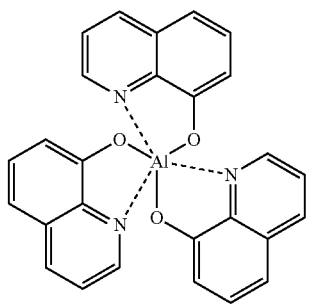
(ET-1)

was deposited in the same manner. The temperature of the crucible for the aluminum 8-hydroxyquinoline complex on this occasion was controlled within the range of 307 to 309°

C. The vacuum degree during deposition was $2.7 \times 10^{-5}$ Pa, the deposition rate was 0.1 nm/sec, and the film thickness was 30 nm.

The substrate temperature during vacuum deposition of the above hole transport layer, light-emitting layer and electron transport layer was kept at room temperature.

Here, the device which had been subjected to deposition up to the electron transport layer 7 was once taken out of the above vacuum deposition apparatus into the atmosphere. A 2-mm width striped shadow mask was brought into close contact with the device so as to cross at right angles to the ITO stripe of the anode 2, and it was placed in a different vacuum deposition apparatus. The apparatus was evacuated within the apparatus to a vacuum degree of $2.0 \times 10^{-4}$ Pa or less in the same manner as the case of the organic layer. As the cathode 8, first, lithium fluoride (LiF) was formed a film in a thickness of 0.5 nm on the electron transport layer 7 at a deposition rate of 0.01 nm/sec and a vacuum degree of $2.2 \times 10^{-4}$ Pa using a molybdenum boat. Subsequently, aluminum was heated in a molybdenum boat in the same manner to form an aluminum layer having a film thickness of 80 nm at a deposition rate of 0.4 nm/sec and a vacuum degree of $7.4 \times 10^{-6}$ Pa, thus the cathode 8 was completed. The substrate temperature during deposition of the above two-layer type cathode 8 was kept at room temperature.

Thus, there was obtained an organic electroluminescent device having a light-emitting area part in the size of 2 mm times 2 mm. Light-emitting characteristics of this device are shown in Table 1. In Table 1, the maximum light emission luminance is a value at a current density of 0.25 A/cm$^2$, and luminance/current and voltage are values at a luminance of 2500 cd/m$^2$, respectively. The maximum wavelength of emission spectrum of the device was 514 nm, and it was identified to be from the organic iridium complex (D-1). A chromaticity was CIE(x, y)=(0.31, 0.62). The driving time is a current-applying time at the time when the light emission luminance reaches 2500 cd/m$^2$ in the case where a direct constant current is successively applied at a constant current value which affords light emission luminance of 5000 cd/m$^2$ at the start of the current application at room temperature. The results are shown in Table 1.

In the table, L/L0 represents relative luminance to the luminance (L0) at the initial stage of driving.

Example 2

An organic electroluminescent device having a structure shown in FIG. 4 was prepared. There was obtained an organic electroluminescent device having a light-emitting area part in the size of 2 mm times 2 mm in the same manner as in Example 1 except that a hole blocking layer 6 was not laminated. Light-emitting characteristics of this device are shown in Table 1. In Table 1, the maximum light emission luminance is a value at a current density of 0.25 A/cm$^2$, and luminance/current and voltage are values at a luminance of 2500 cd/m$^2$, respectively. The maximum wavelength of emission spectrum was 514 nm, and it was identified to be from the organic iridium complex (D-1). A chromaticity was CIE(x, y)=(0.31, 0.62). The driving time is a current-applying time at the time when the light emission luminance reaches 4000 cd/m$^2$ in the case where a direct constant current is successively applied at a constant current value which affords the light emission luminance of 5000 cd/m$^2$ at the start of the current application at room temperature. The results are shown in Table 1.

Example 3

An organic electroluminescent device having a structure shown in FIG. 5 was prepared. There was obtained an organic electroluminescent device having a light-emitting area part in the size of 2 mm times 2 mm in the same manner as in Example 1 except that the compound (H-2) shown below was used instead of the compound (H-1). Light-emitting characteristics of this device are shown in Table 1. In Table 1, the maximum light emission luminance is a value at a current density of 0.25 A/cm$^2$, and luminance/current and voltage are values at a luminance of 2500 cd/m$^2$, respectively. The maximum wavelength of emission spectrum was 514 nm, and it was identified to be from the organic iridium complex (D-1). A chromaticity was CIE(x, y)=(0.31, 0.62).

[Chem 56]

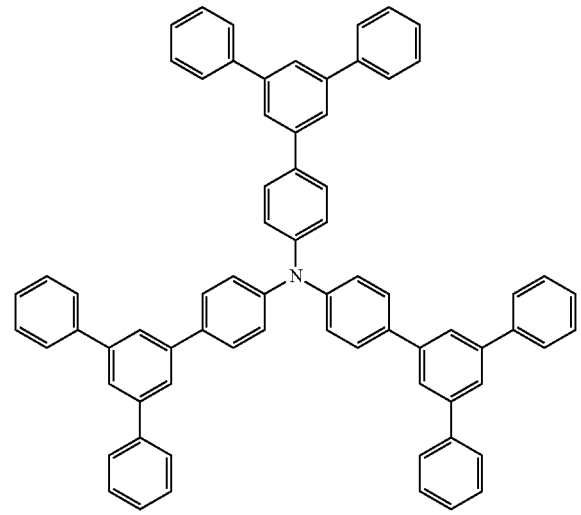

(H-2)

Example 4

An organic electroluminescent device having a structure shown in FIG. 4 was prepared. There was obtained an organic electroluminescent device having a light-emitting area part in the size of 2 mm times 2 mm in the same manner as in Example 3 except that a hole blocking layer 6 was not laminated. Light-emitting characteristics of this device are shown in Table 1. In Table 1, the maximum light emission luminance is a value at a current density of 0.25 A/cm$^2$, and luminance/current and voltage are values at a luminance of 2500 cd/m$^2$, respectively. The maximum wavelength of emission spectrum was 515 nm, and it was identified to be from the organic iridium complex (D-1). A chromaticity was CIE(x, y)=(0.31, 0.62).

Example 5

An organic electroluminescent device having a structure shown in FIG. 5 was prepared. There was obtained an organic electroluminescent device having a light-emitting area part in the size of 2 mm times 2 mm in the same manner as in Example 1 except that the compound (H-3) shown below was used instead of the compound (H-1). Light-emitting characteristics of this device are shown in Table 1. In Table 1, the maximum light emission luminance is a value at a current density of 0.25 A/cm$^2$, and luminance/current and voltage are values at a luminance of 2500 cd/m$^2$, respectively. The maximum wavelength of emission spectrum was 513 nm, and it was identified to be from the organic iridium complex (D-1). A chromaticity was CIE(x, y)=(0.31, 0.62).

[Chem 57]

(H-3)

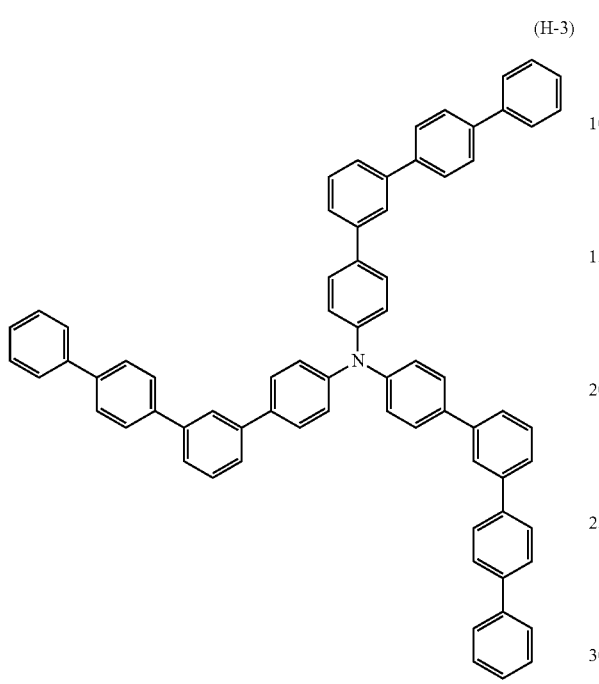

Example 6

An organic electroluminescent device having a structure shown in FIG. 4 was prepared. There was obtained an organic electroluminescent device having a light-emitting area part in the size of 2 mm times 2 mm in the same manner as in Example 5 except that a hole blocking layer 6 was not laminated. Light-emitting characteristics of this device are shown in Table 1. In Table 1, the maximum light emission luminance is a value at a current density of 0.25 A/cm², and luminance/current and voltage are values at a luminance of 2500 cd/m², respectively. The maximum wavelength of emission spectrum was 515 nm, and it was identified to be from the organic iridium complex (D-1). A chromaticity was CIE(x, y)=(0.31, 0.62).

Example 7

An organic electroluminescent device having a structure shown in FIG. 5 was prepared. There was obtained an organic electroluminescent device having a light-emitting area part in the size of 2 mm times 2 mm in the same manner as in Example 1 except that the compound (H-4) shown below was used instead of the compound (H-1) and the compound (E-2) shown below was used instead of the compound (E-1). Light-emitting characteristics of this device are shown in Table 1. In Table 1, the maximum light emission luminance is a value at a current density of 0.25 A/cm², and luminance/current and voltage are values at a luminance of 2500 cd/m², respectively. The maximum wavelength of emission spectrum was 513 nm, and was identified to be from the organic iridium complex (D-1). A chromaticity was CIE(x, y)=(0.31, 0.62).

[Chem 58]

(H-4)

(E-2)

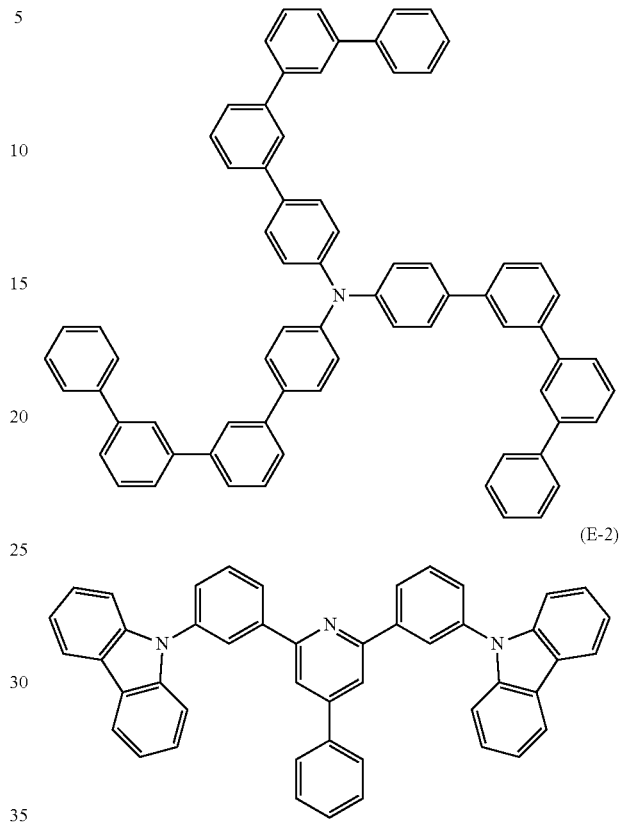

Example 8

An organic electroluminescent device having a structure shown in FIG. 4 was prepared. There was obtained an organic electroluminescent device having a light-emitting area part in the size of 2 mm times 2 mm in the same manner as in Example 7 except that a hole blocking layer 6 was not laminated. Light-emitting characteristics of this device are shown in Table 1. In Table 1, the maximum light emission luminance is a value at a current density of 0.25 A/cm², and luminance/current and voltage are values at a luminance of 2500 cd/m², respectively. The maximum wavelength of emission spectrum was 513 nm, and was identified to be from the organic iridium complex (D-1). Chromaticity was CIE(x, y)=(0.31, 0.62). The driving time is a current-applying time at the time when the light emission luminance reaches 2500 cd/m² in the case where a direct constant current is successively applied at a constant current value which affords the light emission luminance of 5000 cd/m² at the start of the current application at room temperature.

Comparative Example 1

An organic electroluminescent device having a structure shown in FIG. 5 was prepared. There was obtained an organic electroluminescent device having a light-emitting area part in the size of 2 mm times 2 mm in the same manner as in Example 1 except that the compound (PPD) shown below was used instead of the compound (H-1). Light-emitting characteristics of this device are shown in Table 1. In Table 1, the maximum light emission luminance is a value at a current density of 0.25 A/cm$^2$, and luminance/current and voltage are values at a luminance of 2500 cd/m$^2$, respectively. The maximum wavelength of emission spectrum was 514 nm, and it was identified to be from the organic iridium complex (D-1). A chromaticity was CIE(x, y)=(0.31, 0.62). The driving time is a current-applying time at the time when the light emission luminance reaches 2500 cd/m$^2$ in the case where a direct constant current is successively applied at a constant current value which affords the light emission luminance of 5000 cd/m$^2$ at the start of the current application at room temperature. The results are shown in Table 1.

[Chem 59]

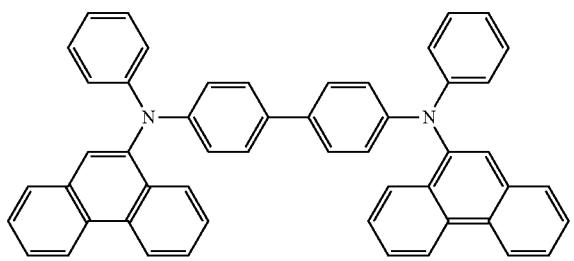

(PPD)

Comparative Example 2

An organic electroluminescent device having a structure shown in FIG. 4 was prepared. There was obtained an organic electroluminescent device having a light-emitting area part in the size of 2 mm times 2 mm in the same manner as in Example 2 except that the compound (PPD) shown above was used instead of the compound (H-1). Light-emitting characteristics of this device are shown in Table 1. In Table 1, the maximum light emission luminance is a value at a current density of 0.25 A/cm$^2$, and luminance/current and voltage are values at a luminance of 2500 cd/m$^2$, respectively. The maximum wavelength of emission spectrum was 514 nm, and it was identified to be from the organic iridium complex (D-1). A chromaticity was CIE(x, y)=(0.31, 0.62). The driving time is a current-applying time at the time when the light emission luminance reaches 4000 cd/m$^2$ in the case where a direct constant current is successively applied at a constant current value which affords the light emission luminance of 5000 cd/m$^2$ at the start of the current application at room temperature. The results are shown in Table 1.

Comparative Example 3

An organic electroluminescent device having a structure shown in FIG. 5 was prepared. There was obtained an organic electroluminescent device having a light-emitting area part in the size of 2 mm times 2 mm in the same manner as in Example 7 except that PPD shown above was used instead of (H-4). Light-emitting characteristics of this device are shown in Table 1. In Table 1, the maximum light emission luminance is a value at a current density of 0.25 A/cm$^2$, and luminance/current and voltage are values at a luminance of 2500 cd/m$^2$, respectively. The maximum wavelength of emission spectrum was 513 nm, and it was identified to be from the organic iridium complex (D-1). A chromaticity was CIE(x, y)=(0.31, 0.61).

Comparative Example 4

An organic electroluminescent device having a structure shown in FIG. 4 was prepared. There was obtained an organic electroluminescent device having a light-emitting area part in the size of 2 mm times 2 mm in the same manner as in Example 8 except that (PPD) shown above was used instead of (H-4). Light-emitting characteristics of this device are shown in Table 1. In Table 1, the maximum light emission luminance is a value at a current density of 0.25 A/cm$^2$, and luminance/current and voltage are values at a luminance of 2500 cd/m$^2$, respectively. The maximum wavelength of emission spectrum was 513 nm, and it was identified to be from the organic iridium complex (D-1). A chromaticity was CIE(x, y)=(0.30, 0.61). The driving time is a current-applying time at the time when the light emission luminance reaches 2500 cd/m$^2$ in the case where a direct constant current is successively applied at a constant current value which affords the light emission luminance of 5000 cd/m$^2$ at the start of the current application at room temperature.

As above, from the results of Examples 1 to 8 and Comparative Examples 1 to 4, it is revealed that the organic electroluminescent device of the invention is an organic electroluminescent device exhibiting a long life, a high luminance, and a high efficiency.

TABLE 1

| | Voltage at start of light emission [V] | Maximum light emission luminance [cd/m$^2$] | Luminance/current [cd/A] | Voltage [V] | Driving time [hour] | |
|---|---|---|---|---|---|---|
| | | | | | L/L0 = 0.5 | L/L0 = 0.8 |
| Example 1 | 3.1 | 81100 | 49.2 | 7.2 | 1764 | — |
| Example 2 | 3.0 | 83700 | 51.5 | 6.3 | — | 225 |
| Example 3 | 3.5 | 73932 | 51.4 | 8.3 | — | — |
| Example 4 | 3.3 | 72322 | 51.2 | 7.3 | — | — |
| Example 5 | 3.0 | 61104 | 42.8 | 7.2 | — | — |
| Example 6 | 3.0 | 55284 | 33.1 | 6.6 | — | — |
| Example 7 | 4.0 | 75634 | 50.0 | 8.4 | — | — |
| Example 8 | 4.0 | 84290 | 53.6 | 7.6 | 994 | — |
| Comparative Example 1 | 3.1 | 43580 | 28.9 | 7.0 | 423 | — |
| Comparative Example 2 | 3.0 | 41120 | 26.3 | 6.1 | — | 118 |
| Comparative Example 3 | 4.0 | 31440 | 21.7 | 8.2 | — | — |
| Comparative Example 4 | 4.0 | 26760 | 16.9 | 7.3 | 528 | — |

Although the invention has been described in detail with reference to specific embodiments thereof, it will be apparent to one skilled in the art that various changes and modifications can be made therein without departing from the spirit and scope of the invention. Incidentally, the present application is based on Japanese Patent Application No. 2005-143569 filed on May 17, 2005 and Japanese Patent Application No. 2006-124450 filed on Apr. 27, 2006, and the whole contents thereof are incorporated herein by reference.

INDUSTRIAL APPLICABILITY

According to the invention, an organic electroluminescent device exhibiting a long life, a high luminance, and a high efficiency can be provided. Moreover, since the monoamine compounds of the invention are excellent in electrical durability, they are useful for an organic electroluminescent device. Furthermore, they are also useful for an electrophotographic photoreceptor.

In addition, the monoamine compounds of the invention are useful not only for a charge transporting material but also for various light-emitting materials, for a solar cell, for a battery material, for a medical use, for a paint, for an organic semi-conductor material, for a toiletry material, for an antistatic material, for a thermoelectric element material, and the like.

The invention claimed is:

1. An organic electroluminescent device comprising on a substrate an anode, a hole transport layer, an organic light-emitting layer, and a cathode, wherein the organic light-emitting layer contains an organic compound having a pyridine ring, a pyrazine ring, or a triazine ring as a partial structure and the hole transport layer contains a monoamine compound represented by the following formula (I):

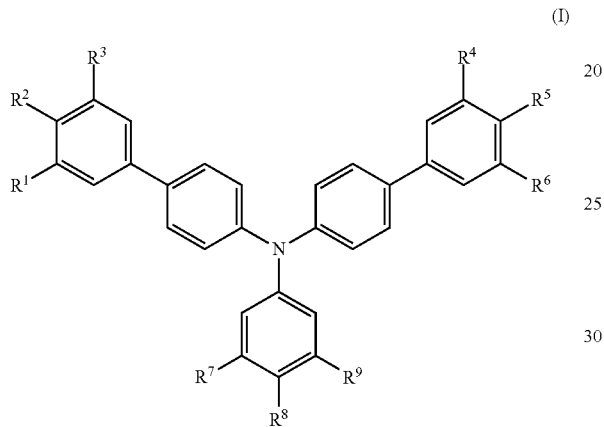

(I)

wherein $R^1$ to $R^9$ represent a hydrogen atom, an aryl group, or an alkyl group; $R^1$ to $R^9$ may be the same or different from each other; and $R^1$ to $R^9$ may further have an aryl group or an alkyl group as a substituent in the case where $R^1$ to $R^9$ are an aryl group or an alkyl group, wherein the monoamine compound has a molecular weight of 400 to 2500, the organic compound further has a N-phenylcarbazole ring as a partial structure, and the monoamine compound has a partial structure represented by the following formula (I-1) and has a glass transition temperature of 90° C. or higher:

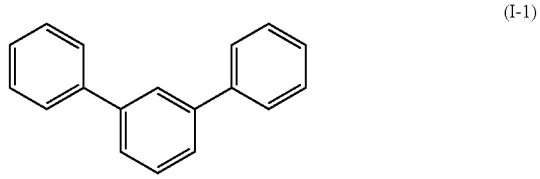 [SMILES: c1ccc(-c2cccc(-c3ccccc3)c2)cc1]

(I-1)

2. The organic electroluminescent device according to claim 1, wherein the organic light-emitting layer contains a light-emitting material and a host material, and the host material is an organic compound having a pyridine ring, a pyrazine ring, or a triazine ring as a partial structure.

3. The organic electroluminescent device according to claim 2, wherein the light-emitting material is an organometallic complex.

\* \* \* \* \*